United States Patent
Eiteman et al.

(10) Patent No.: US 9,212,346 B2
(45) Date of Patent: Dec. 15, 2015

(54) SUBSTRATE-SELECTIVE CO-FERMENTATION PROCESS

(75) Inventors: Mark Eiteman, Athens, GA (US); Elliot Altman, Watkinsville, GA (US)

(73) Assignee: University of Georgia Research Foundation, Inc., Athens, GA (US)

(*) Notice: Subject to any disclaimer, the term of this patent is extended or adjusted under 35 U.S.C. 154(b) by 728 days.

(21) Appl. No.: 13/500,580

(22) PCT Filed: Oct. 7, 2010

(86) PCT No.: PCT/US2010/051767
§ 371 (c)(1),
(2), (4) Date: Jun. 26, 2012

(87) PCT Pub. No.: WO2011/044326
PCT Pub. Date: Apr. 14, 2011

(65) Prior Publication Data
US 2012/0308991 A1    Dec. 6, 2012

Related U.S. Application Data

(63) Continuation-in-part of application No. 12/587,466, filed on Oct. 7, 2009, now Pat. No. 8,551,758, which is a continuation-in-part of application No. PCT/US2008/004577, filed on Apr. 9, 2008.

(60) Provisional application No. 61/004,356, filed on Nov. 27, 2007, provisional application No. 60/922,473, filed on Apr. 9, 2007.

(51) Int. Cl.
| | |
|---|---|
| *C12N 1/22* | (2006.01) |
| *C12P 7/46* | (2006.01) |
| *C12P 7/14* | (2006.01) |
| *C12N 1/36* | (2006.01) |
| *C12P 7/06* | (2006.01) |
| *C12P 7/10* | (2006.01) |
| *C12P 7/16* | (2006.01) |
| *C12P 7/28* | (2006.01) |
| *C12P 7/40* | (2006.01) |
| *C12P 7/52* | (2006.01) |
| *C12P 7/56* | (2006.01) |
| *C12P 39/00* | (2006.01) |

(52) U.S. Cl.
CPC .. *C12N 1/22* (2013.01); *C12N 1/36* (2013.01); *C12P 7/06* (2013.01); *C12P 7/065* (2013.01); *C12P 7/10* (2013.01); *C12P 7/14* (2013.01); *C12P 7/16* (2013.01); *C12P 7/28* (2013.01); *C12P 7/40* (2013.01); *C12P 7/46* (2013.01); *C12P 7/52* (2013.01); *C12P 7/56* (2013.01); *C12P 39/00* (2013.01); *Y02E 50/10* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 4,400,470 A | 8/1983 | Zeikus et al. | |
| 6,455,284 B1 | 9/2002 | Gokarn et al. | |
| 7,749,740 B2 | 7/2010 | Eiteman et al. | |
| 8,551,758 B2 | 10/2013 | Eiteman et al. | |
| 2007/0111294 A1* | 5/2007 | Burgard et al. | ............... 435/145 |
| 2009/0023182 A1 | 1/2009 | Schilling et al. | |
| 2010/0129883 A1 | 5/2010 | Eiteman et al. | |

FOREIGN PATENT DOCUMENTS

| | | |
|---|---|---|
| WO | WO 94/00589 A1 | 1/1994 |
| WO | WO 99/53035 A1 | 12/1999 |
| WO | WO 2005/054487 A1 | 6/2005 |
| WO | WO 2008/124162 A2 | 10/2008 |
| WO | WO 2008/124162 A3 | 4/2009 |
| WO | WO 2011/044326 A2 | 4/2011 |
| WO | WO 2011/044326 A3 | 11/2011 |

OTHER PUBLICATIONS

Xia et al. "Fermentation of Sugar Mixtures found in Lignocellulosic Hydrolysate using Substrate-Selective *Escherichia coli*," Poster Abstract P93 presented at the *SIM Annual Meeting and Exhibition—Industrial Microbiology and Biotechnology*. Sponsored by the Society for Industrial Microbiology. San Francisco, CA: Aug. 1-5, 2010. Available online at <sim.confex.com/sim/2010/webprogram/Paper16340.html>.

Xia et al. "Fermentation of sugar mixtures found in Lignocellulosic Hydrolysate using Substrate-Selective *Escherichia coli*," Poster Abstract P66 presented at the *SIM Annual Meeting and Exhibition—Industrial Microbiology and Biotechnology*. Sponsored by the Society for Industrial Microbiology. New Orleans, LA: Jul. 24-28, 2011. Available online at <sim.confex.com/sim/2011/webprogram/Paper19819.html>.

Atsumi et al., "Non-fermentative pathways for synthesis of branched-chain higher alcohols as biofuels," Jan. 3, 2008 *Nature* 451:86-89.

Barbosa et al., "Efficient fermentation of *Pinus* sp. acid hydrolysates by an ethanologenic strain of *Escherichia coli*," 1992, *Appl. Env. Micro.* 58:1382-1384.

Berson et al., "Detoxification of actual pretreated corn stover hydrolysate using activated carbon powder," Spring 2005, *Appl. Biochem. Biotechnol.* 124:923-934.

Bramley and Kornberg, "Sequence homologies between proteins of bacterial phosphoenolpyruvate-dependent sugar phosphotransferase systems: identification of possible phosphate-carrying histidine residues," Jul. 1987, *Proc. Nati. Acad. Sci. USA* 84:4777-4780.

Brandberg et al., "The fermentation performance of nine strains of *Saccharomyces cerevisiae* in batch and fed-batch cultures in dilute-acid wood hydrolysate," 2004, *J. Biosci. Bioeng.* 98:122-125.

(Continued)

*Primary Examiner* — Rebecca Prouty
(74) *Attorney, Agent, or Firm* — Mueting, Raasch & Gebhardt, P.A.

(57) ABSTRACT

Biological method for conversion of a sugar-containing organic material into a desired biochemical product. Use of a plurality of substrate-selective cells allows different sugars in a complex mixture to be consumed concurrently and independently. The method can be readily extended to remove inhibitory compounds from hydrolysate.

16 Claims, 25 Drawing Sheets

(56) References Cited

OTHER PUBLICATIONS

Casal et al., "Effects of ethanol and other alkanols on transport of acetic acid in *Saccharomyces cerevisiae*," Feb. 1998, *Appl. Environ. Microbiol.* 64(2):665-668.

Chaillou et al., "Molecular cloning and functional expression in lactobacillus plantarum 80 of xylT, encoding the D-xylose-H+ symporter of *Lactobacillus brevis*," Dec. 1998, *Appl. Environ. Microbiol.* 64:4720-4728.

Chaillou et al., "Transport of D-xylose in *Lactobacillus pentosus, Lactobacillus casei*, and *Lactobacillus plantarum*: evidence for a mechanism of facilitated diffusion via the phosphoenolpyruvate:mannose phosphotransferase system," Aug. 1999, *J. Bacteriol.* 181:4768-4773.

Challener, "Sugar never tasted so sweet," Jun. 2009 *Specialty Chemicals Magazine* 6:42-44.

Chandel et al., "Detoxification of sugarcane bagasse hydrolysate improves ethanol production by *Candida shehatae* NCIM 3501," Jul. 2007, *Bioresour. Technol.* 98:1947-1950. Available online on Oct. 2, 2006.

Chandrakant and Bisaria, "Simultaneous bioconversion of glucose and xylose to ethanol by *Saccharomyces cerevisiae* in the presence of xylose isomerase," Mar. 2000, *Appl. Micro. Biotechnol.* 53:301-309.

Cherepanov and Wackernagel, "Gene disruption in *Escherichia coli*: TcR and KmR cassettes with the option of Flp-catalyzed excision of the antibiotic-resistance determinant," May 26, 1995, *Gene* 158:9-14.

Cherrington et al., "Short-chain organic acids at ph 5.0 kill *Escherichia coli* and *Salmonella* spp. without causing membrane perturbation," Feb. 1991 *J. Appl. Bacteriol.* 70:161-165.

Chesson et al., "Substituent groups linked by alkali-labile bonds to arabinose and xylose residues of legume, grass and cereal straw cell walls and their fate during digestion by rumen microorganisms," Dec. 1983, *J. Sci. Food Agric.* 34:1330-1340.

Clark, "The fermentation pathways of *Escherichia coli*," Sep. 1989, *FEMS Microbiol. Rev.* 63:223-224.

Conway et al., "Promoter and nucleotide sequences of the *Zymomonas mobilis* pyruvate decarboxylase," Mar. 1999 *J. Bacteriol.* 169:949-954.

Conway et al., "Cloning and sequencing of the alcohol dehydrogenase II gene from *Zymomonas mobilis*," Mar. 1999 *J. Bacteriol.* 169:2591-2597.

Curtis and Epstein, "Phosphorylation of D-glucose in *Escherichia coli* mutants defective in glucosephosphotransferase, mannosephosphotransferase, and glucokinase," Jun. 1975, *J. Bacteriol.* 122:1189-1199.

Datsenko and Wanner, "One-step inactivation of chromosomal genes in *Escherichia coli* K-12 using PCR products," Jun. 6, 2000, *Proc. Natl. Acad. Sci. USA* 97:6640-6445.

David and Wiesmeyer, "Control of xylose metabolism in *Escherichia coli*," Mar. 24, 1970, *Biochim. Biophys. Acta.* 201:497-499.

De Graef et al., "The steady-state internal redox state (NADH/NAD) reflects the external redox state and is correlated with catabolic adaptation in *Escherichia coli*," Apr. 1999, *J. Bacteriol* 181:2351-2357.

Delgenes et al., "Biological production of industrial chemicals, i.e. xylitol and ethanol, from lignocelluloses by controlled mixed culture systems," Jan. 1998 *Ind. Crops Prod.* 7:101-111.

Dien et al., "Conversion of corn fiber to ethanol by recombinant *E. coli* strain FBR3," Jun. 1999 *J. Ind. Microbiol. Biotech.* 22:575-581.

Dien et al., "Fermentation of sugar mixtures using *Escherichia coli* catabolite repression mutants engineered for production of L-lactic acid," Nov. 2002, *J. Industr. Micro. Biotech.* 29:221-227.

Dills et al., "Regulation of hexitol catabolism in *Streptococcus mutans*," Feb. 1983 *J. Bacteriol.* 153:861-866.

Dittrich et al., "Redistribution of metabolic fluxes in the central aerobic metabolic pathway of *E. coli* mutant strains with deletion of the ackA-pta and poxB pathways for the synthesis of isoamyl acetate," Mar.-Apr. 2005 *Biotech. Prog.* 21:627-631.

Doelle et al., "*Zymomonas mobilis*—science and industrial application," 1993, *Crit. Rev. Biotechnol.* 13:57-98.

Does et al., "Isolation and Characterization of *Pichia heedii* Mutants Defective in Xylose Uptake," Nov. 1990 *Appl. Environ. Microbiol.* 56:3321-3328.

Dumsday et al., "Comparative stability of ethanol production by *Escherichia coli* KO11 in batch and chemostat culture," Jul. 1999, *J. Industr. Micro. Biotech.* 23:701-708.

"*E. coli* genotypes," [online]. OpenWetWare database entry [retrieved on Feb. 21, 2014]. Retrieved from the Internet: <openwetware.org/wiki/E._coli_genotypes>; 16 pgs.

Eiteman and Chastain, "Optimization of the ion-exchange analysis of organic acids from fermentation," Feb. 10, 1997, *Anal. Chim. Acta* 338:69-75.

Eiteman et al., "A co-fermentation strategy to consume sugar mixtures effectively," Feb. 27, 2008, *J. Biol. Engineering*, 2:3; 8 pages.

Eiteman et al., "Substrate Selective Uptake to Remove Acetate and Convert Sugar Mixtures," Oral Presentation Abstract 7-01 at the *30th Symposium on Biotechnology for Fuels and Chemicals*. Sponsored by the Society for Industrial Microbiology. New Orleans, LA: May 4-7, 2008. Cover page, schedule for May 6, 2008, and p. 53.

Eiteman et al., "S40: Conversion of Sugar Mixtures in the Presence of Acetic Acid," Oral Presentation Abstract S40 at the *Society for Industrial Microbiology Annual Conference*. Sponsored by the Society for Industrial Microbiology. San Diego, CA: Aug. 10-14, 2008. Cover page, schedule for Aug. 11, 2008, and p. 72.

Eiteman et al., "A substrate-selective co-fermentation strategy with *Escherichia coli* produces lactate by simultaneously consuming xylose and glucose," Feb. 15, 2009 *Biotechnol. Bioeng.* 201:822-827. Available online on Aug. 29, 2008.

Eiteman and Altman, "A novel fermentation strategy for removing the key inhibitor acetic acid and efficiently utilizing the mixed sugars from lignocellulosic hydrolysates," Grant Abstract, Grant No. FG02-07ER86331 [online]. USDOE Office of Biomass Program. Final Technical Report published on Feb. 11, 2009. Retrieved from the Internet: <http://www.osti.gov/bridge/product.biblio.jsp?query_id=1&page=0&osti_id=971996>; 29 pgs.

Eiteman and Altman, "Engineered Microbial Systems for Conversion of Biomass Hydrolysates," Grant Abstract, Grant No. 0929893 [online]. CBET Division of Chemical, Bioengineering, Environmental, and Transport Systems; National Science Foundation. Project dates Sep. 1, 2009 to Aug. 31, 2013 [retrieved on Jun. 15, 2012]. Retrieved from the Internet: <http://www.nsf.gov/awardsearch/showAward.do?AwardNumber=0929893>; 2 pgs.

El-Mansi et al., "Control of carbon flux through enzymes of central and intermediary metabolism during growth of *Escherichia coli* on acetate," Apr. 2006, *Curr. Opin. Microbiol.* 9:173-179. Available online on Mar. 10, 2006.

Erlandson et al., "Dissolution of xylose metabolism in *Lactococcus lactis*," Sep. 2000, *Appl. Environ. Microbiol.* 66:3974-3980.

Fengel and Wegener, *Wood: Chemistry, ultrastructure, reactions*. Walter de Gruyter Inc.: Berlin, Germany; 1989. Title page, publisher's page, and table of contents; 9 pages.

Garrigues et al., "Control of the shift from homolactic acid to mixed-acid fermentation in *Lactococcus lactis*: predominant role of the NADH/NAD$^+$ ratio," Sep. 1997, *J. Bacteriol.* 179:5282-5287.

Gokarn et al., "The physiological effects and metabolic alterations caused by the expression of *Rhizobium etli* pyruvate carboxylase in *Escherichia coli*," Jul. 2001 *Appl. Environ. Microbiol.* 56:188-195.

Guettler et al., "*Actinobacillus succinogenes* sp. nov., a novel succinic-acidproducing strain from the bovine rumen," Jan. 1999 *Int J Syst Bacteriol.* 49(Pt 1):207-216.

Hagedorn et al., "Isolation and characterization of xyl mutants in a xylose-utilizing yeast, *Pichia stipitis*," Jul. 1989 *Curr. Genetics*, 16:27-33.

Helle et al., "Effect of inhibitory compounds found in biomass hydrolysates on growth and xylose fermentation by a genetically engineered strain of *S. cerevisiae*," Nov. 5, 2003, *Enzyme Microbial. Technol.* 33:786-792. Available online on Sep. 4, 2003.

Ho et al., "Genetically engineered *Saccharomyces* yeast capable of effective cofermentation of glucose and xylose," May 1998, *Appl. Env. Micro.* 64:1852-1859.

(56) References Cited

OTHER PUBLICATIONS

Holms, "The central metabolic pathways of *Escherichia coli*: relationship between flux and control at a branch point, efficiency of conversion to biomass, and excretion of acetate," 1986, *Curr. Top. Cell Regul.* 28:69-105.
Horváth et al., "Selection of anion exchangers for detoxification of dilute-acid hydrolysates from spruce," Spring 2004, *Appl. Biochem. Biotechnol.* 114:525-538.
Huber and Erni, "Membrane topology of the mannose transporter of *Escherichia coli* K12," Aug. 1, 1996, *Eur. J. Biochem.* 239:810-817.
Imai et al., "The relationship between viability and intracellular pH in the yeast *Saccharomyces cerevisiae*," Oct. 1995 *Appl. Environ. Microbiol.* 61:3604-3608.
Ingram et al., "Genetic engineering of ethanol production in *Escherichia coli*," Oct. 1987, *Appl. Environ. Microbiol.* 53:2420-2425.
Ingram and Conway, "Expression of Different Levels of Ethanologenic Enzymes from *Zymomonas mobilis* in Recombinant Strains of *Escherichia coli*," Feb. 1988, *Appl. Environ. Microbiol.* 54:397-404.
Ingram et al., "Enteric bacterial catalysts for fuel ethanol production," Sep.-Oct. 1999, *Biotechnol. Prog.* 15:855-866.
Jensen, "*The Escherichia coli* K-12 'wild types' W3110 and MG1655 have an rph frameshift mutation that leads to pyrimidine starvation due to low pyrE expression levels," Jun. 1993, *J. Bacteriol.* 175:3401-3407.
Johansson et al., "Xylulokinase overexpression in two strains of *Saccharomyces cerevisiae* also expressing xylose reductase and xylitol dehydrogenase and its effect on fermentation of xylose and lignocellulosic hydrolysate," Sep. 2001, *Appl. Environ. Microbiol.* 67:4249-4255.
Kimata et al., "cAMP receptor protein-cAMP plays a crucial role in glucose-lactose diauxie by activating the major glucose transporter gene in *Escherichia coli*," Nov. 25, 1997, *Proc. Natl. Acad. Sci. USA.* 94:12914-12919.
Klinke et al., "Inhibition of ethanol-producing yeast and bacteria by degradation products produced during pre-treatment of biomass," Nov. 2004, *Appl. Microbiol. Biotechnol.* 66:10-26. Available online on Aug. 6, 2004.
Kornberg et al., "Genetic control of glucose uptake by *Escherichia coli*," Feb. 1972 *FEBS Lett.* 20:270-272.
Kuyper et al., "Evolutionary engineering of mixed-sugar utilization by a xylose-fermenting *Saccharomyces cerevisiae* strain," Jul. 2005, *FEMS Yeast Res.* 5:925-934. Available online on May 24, 2005.
Lakshmanaswamy et al., "Microbial removal of acetate selectively from sugar mixtures," Sep. 2011 *J. Ind. Microbiol. Biotech.* 38:1477-1484. Available online on Jan. 12, 2011.
Laplace et al., "Alcoholic glucose and xylose fermentations by the coculture process: compatibility and typing of associated strains," Jul. 1992 *Can. J. Microbiol.* 38:654-658.
Laplace et al., "Cofermentation of glucose and xylose to ethanol by a respiratory-deficient mutant of *Saccharomyces cerevisiae* co-cultivated with a xylose-fermenting yeast," Jan. 1, 1993 *J. Ferment. Bioeng.* 75:207-212.
Lasko et al., "Bacterial response to acetate challenge: a comparison of tolerance among species," Aug. 2000, *Appl. Microbiol. Biotechnol.* 54(2):243-247.
Lee et al., "Aerobic production of alanine by *Escherichia coli* aceF ldhA mutants expressing the *Bacillus sphaericus* alaD gene," Jul. 2004, *Appl. Microbiol. Biotechnol.* 65:56-60. Available online on Feb. 4, 2004.
Lin et al., "Ethanol fermentation from biomass resources: current state and prospects," Feb. 2006 *Appl. Microbiol. Biotech.* 69:627-642.
Lokman et al., "Organization and characterization of three genes involved in D-xylose catabolism in *Lactobacillus pentosus*," Nov. 1991, *Mol. Gen. Genet.* 230:161-169.

Lu et al., "pH and base counterion affect succinate production in dual-phase *Escherichia coli* fermentations," Aug. 2009 *J. Ind. Microbiol.* Biotech. 36:1101-1109. Available online on May 30, 2009.
Luesink et al., "Molecular characterization of the *Lactococcus lactis* ptsHI operon and analysis of the regulatory role of HPr," Feb. 1999, *J. Bacteriol.* 181:764-771.
Martinez et al., "Detoxification of Dilute Acid Hydrolysates of Lignocellulose with Lime," 2001 *Biotech. Prog.* 17:287-293.
Metcalf et al., "Conditionally replicative and conjugative plasmids carrying lacZa for cloning, mutagenesis, and allele replacement in bacteria," Jan. 1996, *Plasmid* 35:113.
Mohagheghi et al., "Cofermentation of glucose, xylose, and arabinose by genomic DNA-integrated xylose/arabinose fermenting strain of *Zymomonas mobilis* AX101," Spring 2002 *Appl. Biochem. Biotech.* 98-100:885-898.
Murray et al., "Ethanol fermentation of hexose and pentose wood sugars produced by hydrogen-fluoride solvolysis of aspen chips," May 1984 *Biotech. Lett.* 6:323-326.
Nichols et al., "Use of catabolite repression mutants for fermentation of sugar mixtures to ethanol," Jul. 2001, *Appl. Microbiol. Biotechnol.* 56:120-125.
Nichols et al., "Engineering lactic acid bacteria with pyruvate decarboxylase and alcohol dehydrogenase genes for ethanol production from *Zymomonas mobilis*," May 2003, *J. Indust. Microbiol. Biotechnol.* 30:315-321. Available online on May 15, 2003.
Paalme et al., "The growth rate control in *Escherichia coli* at near to maximum growth rates: the A-stat approach," Mar. 1997, *Antonie Van Leeuwen.* 71:217-230.
Pampulha et al., "Combined effect of acetic acid, pH and ethanol on intracellular pH of fermenting yeast," Oct. 1989 *Appl. Microbiol. Biotech.* 31:547-550.
Paster et al., "Industrial Bioproducts: Today and Tomorrow," Jul. 2003 (revised Mar. 2004). Prepared by Energetics Incorporated: Columbia, MD, for the United States Department of Energy Office of Energy Efficiency and Renewable Energy—Office of the Biomass Program. Available online. Retrieved on Jun. 6, 2012; retrieved from the Internet at: <http://www.energetics.com/resourcecenter/products/studies/Documents/bioproducts-pportunities.pdf>; 91 pages.
Phue and Shiloach, "Transcription levels of key metabolic genes are the cause for different glucose utilization pathways in *E. coli* B (BL21) and *E. coli* K (JM109)," Apr. 8, 1998, *J. Biotechnol.* 109:21-30.
Postma et al., "Phosphoenolpyruvate: carbohydrate phosphotransferase systems of bacteria," Sep. 1993 *Microbiol. Rev.* 57:543-594.
Presper et al., "Site-directed mutagenesis of the phosphocarrier protein. IIIGlc, a major signal-transducing protein in *Escherichia coli*," Jun. 1989 *Proc. Nati. Acad. Sci. USA* 86:4052-4055.
Prior and Kornberg, "Nucleotide sequence of fruA, the gene specifying enzyme Mu of the phosphoenolpyruvate-dependent sugar phosphotransferase system in *Escherichia coli* K12," Oct. 1988, *J. Gen. Microbiol.* 134:2757-2768.
Qian et al., "Ethanol production from dilute-Acid softwood hydrolysate by co-culture," Sep. 2006 *Appl. Biochem. Biotechnol.* 134:273-283.
Reidl and Boos, "The malX malY operon of *Escherichia coli* encodes a novel enzyme II of the phosphotransferase system recognizing glucose and maltose and an enzyme abolishing the endogenous induction of the maltose system," Aug. 1991, *J. Bacteriol.* 173:4862-4876.
Reifenberger et al., "Identification of novel HXT genes in *Saccharomyces cerevisiae* reveals the impact of individual hexose transporters on glycolytic flux," 1995 *Mol. Microbiol.* 16:157-167.
Roberto et al., "Utilization of sugar cane bagasse hemicellulosic hydrolysate by *Pichia stipitis* for the production of ethanol," Feb. 1991 *Process Biochem.* 26:15-21.
Saddler and Mackie, "Bioconversion of lignocellulosics," 1990, *Biomass* 22:293-305.
Saier and Roseman, "Sugar transport. The crr mutation: its effect on repression of enzyme synthesis," Nov. 10, 1976, *J. Biol. Chem.* 251:6598-6605.

(56) References Cited

OTHER PUBLICATIONS

Sakai et al., "Effect of lignocellulose-derived inhibitors on growth of and ethanol production by growth-arrested *Corynebacterium glutamicum* R," Apr. 2007 *Appl. Environ. Microbiol.* 73:2349-2353. Available online on Feb. 2, 2007.

Samuelov et al., "Whey fermentation by *Anaerobiospirillum succiniciproducens* for production of a succinate-based animal feed additive," May 1999 *Appl. Environ. Microbiol.* 65:2260-3.

Sambrook et al., *Molecular Cloning: A Laboratory Manual, Second Edition*. Cold Spring Harbor Laboratory Press: Cold Spring Harbor, NY; 1989. Title page, publisher's page, and table of contents; 30 pages.

Schmid et al., "Plasmid-mediated sucrose metabolism in *Escherichia coli* K12: mapping of the scr genes of pUR400," Jan. 1988 *Mol. Microbiol.* 2:1-8.

Schnetz et al., "Beta-glucoside (bgl) operon of *Escherichia coli* K-12: nucleotide sequence, genetic organization, and possible evolutionary relationship to regulatory components of two *Bacillus subtilis* genes," Jun. 1987, *J. Bacteriol.*169:2579-2590.

Sedlak et al., "DNA microarray analysis of the expression of the genes encoding major enzymes in ethanol production during glucose and xylose co-fermentation by metabolically engineered *Saccharomyces* yeast," Jul. 16, 2003, *Enzyme. Microbial. Technol.* 33:19-28.

Sedlak and Ho, "Production of Ethanol from Cellulosic Biomass Hydrolysates Using Genetically Engineered *Saccharomyces* Yeast Capable of Cofermenting Glucose and Xylose," Spring 2004 *Appl. Microbiol. Biotechnol.* 113-116:403-416.

Shi et al., "Characterization and complementation of a *Pichia stipitis* mutant unable to grow on D-xylose or L-arabinose," 2000 *Appl. Biochem. Biotechnol.* 84-86:201-216.

Smith et al., "Fed-batch two-phase production of alanine by a metabolically engineered *Escherichia coli*," Oct. 2006, *Appl. Microbiol. Biotechnol.* 28:1695-1700.

Stentz et al., "Molecular cloning and analysis of the ptsHI operon in *Lactobacillus sake*," Jun. 1997, *Appl. Environ. Microbiol.* 63:2111-2116.

Taherzadeh et al., "Continuous cultivation of dilute-acid hydrolysates to ethanol by immobilized *Saccharomyces cerevisiae*," Jul. 2001, *Appl. Biochem. Biotechnol.* 95:4557.

Takahashi et al., "Effects of acetate on the growth and fermentation performance of *Escherichia coli* KO11," Sep. 1999 *Appl. Biochem. Biotech.* 81:193-203.

Talarico et al., "Construction and expression of an ethanol production operon in Gram-positive bacteria," Dec. 2005 *Microbiol.* 151:4023-4031.

Taniguchi et al. "Production of L-lactic acid from a mixture of xylose and glucose by co-cultivation of lactic acid bacteria," Dec. 2004 *Appl. Microbiol. Biotechnol.* 66:160-165. Available online on Jul. 29, 2004.

Tao et al., "Engineering a homo-ethanol pathway in *Escherichia coli*: increased glycolytic flux and levels of expression of glycolytic genes during xylose fermentation," May 2001, *J. Bacteriol.* 183:2979-2988.

Timell, "Recent progress in the chemistry of wood hemicelluloses," Mar. 1967, *Wood Sci. Technol.* 1:45-70.

Tomar et al., "The effect of acetate pathway mutations on the production of pyruvate in *Escherichia coli*," Jul. 2003, *Appl. Microbiol. Biotechnol.* 62:76-82. Available online on Feb. 26, 2003.

Torssell, *Natural product chemistry: a mechanistic, biosynthetic and ecological approach, Second Edition*. Apotekarsocieteten, Swedish Pharmaceutical Society: Stockholm, Sweden; 1997. Title page, publisher's page, and table of contents; 6 pages.

Tran et al., "Ethanol fermentation of red oak acid prehydrolysate by the yeast *Pichia stipitis* CBS 5776," Jul. 1986 *Enzyme Microb. Tech.* 8:439-444.

Van De Walle and Shiloach, "Proposed mechanism of acetate accumulation in two recombinant *Escherichia coli* strains during high density fermentation," Jan. 1998, *Biotechnol. Bioeng.* 57:71-78.

Van Zyl et al., "Acetic acid inhibition of d-xylose fermentation by *Pichia stipitis*," Jan. 1991, *Enzyme Micro. Technol.* 13:82-86.

Vemuri et al., "Effects of growth mode and pyruvate carboxylase on succinic acid production by metabolically engineered strains of *Escherichia coli*," Apr. 2002 *Appl. Environ. Microbiol.* 68:1715-27.

Vemuri et al., "Succinate production in dual-phase *Escherichia coli* fermentations depends on the time of transition from aerobic to anaerobic conditions," Jun. 2002 *J. Ind. Microbiol. Biotechnol.* 28:325-332.

Vemuri et al., "Overflow metabolism in *Escherichia coli* during steady-state growth: transcriptional regulation and effect of the redox ratio," May 2006, *Appl. Environ. Microbiol.* 72(5):3653-3661.

Viana et al., "Enzyme I and HPr from *Lactobacillus casei*: their role in sugar transport, carbon catabolite repression and inducer exclusion," May 2000, *Mol. Microbiol.* 36:570-584.

Von Sivers et al., "Cost analysis of ethanol production from willow using recombinant *Escherichia coli*," Sep.-Oct. 1994, *Biotechnol. Prog.* 10:555-560.

Wallis, "Chapter 9. Solvolysis by acids and bases," in *Lignins: occurrence, formation, structure and reactions*, Sarkanen and Ludwig (Eds.) Wiley-Interscience: New York, NY; 1971. Title page, publisher's page, and pp. 345-372.

Walsh et al., "*Saccharomyces cerevisiae* null mutants in glucose phosphorylation: metabolism and invertase expression," Jul. 1991 *Genetics* 128:521-527.

Weierstall et al., "Cloning and characterization of three genes (SUT1-3) encoding glucose transporters of the yeast *Pichia stipitis*," Feb. 1999 *Mol. Microbiol.* 31:871883.

Wilson et al., "Comparative fermentability of enzymatic and acid hydrolysates of steam-pretreated aspenwood hemicellulose by *Pichia stipitis* CBS 5776," 1989, *Appl. Microbiol. Biotechnol.* 31:592-596.

Xia et al., "Simultaneous utilization of glucose, xylose and arabinose in the presence of acetate by a consortium of *Escherichia coli* strains," Jun. 12, 2012, *Microbial Cell Factories* 11:77. Available online ahead of print at <http://www.microbialcellfactories.com/content/pdf/1475-2859-11-77.pdf>; 20 pages.

Yu et al., "An efficient recombination system for chromosome engineering in *Escherichia coli*," May 23, 2000, *Proc. Natl. Acad. Sci. USA.* 97:5978-5983.

Zaldivar et al., "Effect of selected aldehydes on the growth and fermentation of ethanologenic *Escherichia coli*," Oct. 5, 1999, *Biotechnol. Bioeng.* 65:24-33.

Zaldivar and Ingram, "Effect of organic acids on the growth and fermentation of ethanologenic *Escherichia coli* LY01," 1999, *Biotechnol. Bioeng.* 66:203-210.

Zaldivar et al., "Effect of alcohol compounds found in hemicellulose hydrolysate on the growth and fermentation of ethanologenic *Escherichia coli*," Jun. 5, 2000, *Biotechnol. Bioeng.* 68:524-530. Available online on Apr. 19, 2000.

Zaldivar et al., "Fuel ethanol production from lignocellulose: a challenge for metabolic engineering and process integration," Jul. 2001, *Appl. Microbiol. Biotechnol.* 56:17-34.

Zaldivar et al., "Fermentation performance and intracellular metabolite patterns in laboratory and industrial xylose-fermenting *Saccharomyces cerevisiae*," Aug. 2002 *Appl. Microbiol. Biotech.* 59:436-442. Available online on Jul. 3, 2002.

Zhang et al., "Promising ethanologens for xylose fermentation," Sep. 1995, *Appl. Biochem. Biotechnol.* 51/52:527-536.

Zhang et al., "Metabolic Engineering of a Pentose Metabolism Pathway in Ethanologenic *Zymomonas mobilis*," Jan. 13, 1995, *Science* 267:240-243.

Zhu et al., "Homolactate fermentation by metabolically engineered *Escherichia coli* strains," Jan. 2007, *Appl. Environ. Microbiol.* 73:456-464. Available online on Nov. 22, 2006.

Zhu et al., "High glycolytic flux improves pyruvate production by a metabolically engineered *Escherichia coli* strain," Nov. 2008 *Appl. Environ. Microbiol.* 74:6649. Available online on Sep. 19, 2008.

International Search Report mailed Mar. 5, 2009, in connection with International Patent Application No. PCT/US2008/004577, filed Apr. 9, 2008; 8 pages.

Written Opinion mailed Mar. 5, 2009, in connection with International Patent Application No. PCT/US2008/004577, filed Apr. 9, 2008; 16 pages.

(56) References Cited

OTHER PUBLICATIONS

International Preliminary Report on Patentability issued Oct. 13, 2009, in connection with International Patent Application No. PCT/US2008/004577, filed Apr. 9, 2008; 17 pages.

International Search Report mailed Aug. 17, 2011, in connection with International Patent Application No. PCT/US2010/051767, filed Oct. 7, 2010; 4 pages.

Written Opinion mailed Aug. 17, 2011, in connection with International Patent Application No. PCT/US2010/051767, filed Oct. 7, 2010; 7 pages.

International Preliminary Report on Patentability issued Apr. 11, 2012, in connection with International Patent Application No. PCT/US2010/051767, filed Oct. 7, 2010; 8 pages.

Gerhardt et al. (eds.), *Methods for General and Molecular Bacteriology*, American Society for Microbiology: Washington, D.C.; 1994. Title Page, Table of Contents, and Chapters 13-14 and 16-18, 107 pages.

Hayashi et al., "Highly accurate genome sequences of *Escherichia coli* K-12 strains MG1655 and W3110" *Mol. Syst. Biol.* 2006; 2:2006.0007. 5 pages. Available online on Feb. 21, 2006.

Lengeler et al., "Phosphoenolpyruvate-dependent phosphotransferase system enzyme III and plasmid-encoded sucrose transport in *Escherichia coli* K-12" *J. Bacteriol.* 1982; 151(1):468-71.

Schellenberg et al., "Xylose isomerase from *Escherichia coli*. Characterization of the protein and the structural gene" *J. Biol. Chem.* 1984; 259(11):6826-32.

Singer et al., "DNA plasmid production in different host strains of *Escherichia coli*" *J. Ind. Microbiol. Biotechnol.* Apr. 2009; 36(4):521-30. Available online on Jan. 10, 2009.

\* cited by examiner

SUBSTRATE-SELECTIVE CO-FERMENTATION PROCESS

This application is the §371 U.S. National Stage of International Application No. PCT/US2010/051767, filed 7 Oct. 2010, published in the English language on Apr. 14, 2011 as International Publication No. WO 2011/044326, which is a continuation-in-part of U.S. Ser. No. 12/587,466, now U.S. Pat. No. 8,551,758, filed Oct. 7, 2009, which is a continuation-in-part of International Application No. PCT/US2008/004577, filed Apr. 9, 2008, which claims the benefit of U.S. Provisional Application Ser. No. 60/922,473, filed Apr. 9, 2007, and U.S. Provisional Application Ser. No. 61/004,356, filed Nov. 27, 2007, each of which is incorporated by reference herein.

BACKGROUND

Over the last ten years many reports have provided compelling evidence for a competitively priced bio-based products industry that will replace much of the petrochemical industry. In order to reduce U.S. reliance on foreign oil, there is an increasing interest in generating commodity and fine chemicals from widely available U.S. renewable resources through fermentation. In the last five years, billions of dollars have been invested in commercializing the microbial production of several chemicals, including lactic acid, 1,3-propanediol and 3-hydroxypropanoic acid. In concert with this increased interest in crop-derived biochemicals, molecular biology has become a standard tool which engineers and applied scientists use routinely to aid the rational and targeted alteration of metabolism.

The efficient use of agricultural biomass for the production of any biochemical, however, is problematic. Technical challenges to be overcome in order for bio-based industrial products to be cost-competitive include finding new technology and reducing the cost of technology for converting biomass into desired bio-based industrial products. Research resulting in cost-effective technology to overcome the recalcitrance of cellulosic biomass would allow biorefineries to produce fuels and bulk chemicals on a very large scale.

The untapped sources of biomass are largely lignocellulosic in nature. One promising use of lignocellulose for liquid fuel is in the microbial production of ethanol. Unfortunately, when broken down into constituents, a very complex mixture remains. This mixture contains sugars which individually but not collectively are suitable for fermentation, and the mixture also contains inhibitors.

Because the unit value of chemical products derived from biomass (e.g., ethanol) is generally low while the potential market is large, the economic viability of such processes depends on the yield and productivity. Yield is the quantity of product formed per mass of material input, while productivity is the rate at which the product is generated. Achieving high yield demands that all biomass components be converted, while high productivity requires that the complex conversions be accomplished quickly.

The conversion of lignocellulosic biomass to any useful fermentation product follows a series of general process operations which include identifying the biomass, harvesting it, various separation/extraction steps, pretreatments, conversion and subsequent purification steps. Although the particular substrate and chemical product determine the details of each operation, the complex structure of biomass invariably necessitates that its components be broken down by various depolymerization strategies.

Fermentation is the biological process in which sugar substrates, such as glucose and xylose, are converted into fermentation products, such as ethanol. While the term fermentation is usually reserved for anaerobic processes, analogous microbial processes similarly convert sugar substrates into products under a controlled aerobic environment or under conditions of partial oxygenation. One major limitation is that, regardless of a microorganism's ability to metabolize multiple substrates, a single substrate persistently remains the preferred substrate and the consumption of the sugars is asynchronous. Invariably, a multitude of substrates remains long after the preferred substrate has been metabolized. Numerous attempts to engineer microorganisms capable of equally metabolizing more than one substrate have been made (Dien et al., 2002, *J. Industr. Micro.* 29:221; Sedlak et al., 2003, *Enzyme Micro. Technol.* 33:19; Chandrakant and Bisaria, 2000, *Appl. Micro. Biotechnol.* 53:301; Kuyper et al., 2005, *FEMS Yeast Res.* 5:925; Zhang et al., 1995, *Science* 267:240). However, none has prevented the polyauxic behavior of linearly metabolizing one sugar at a time when metabolizing sugar mixtures (i.e., first glucose consumption, then xylose, etc.).

A single microorganism alone is unable to convert multiple sugars simultaneously. Instead, any given microorganism has a complex regulatory network which forces sugars to be metabolized sequentially. This sequential nature invariably reduces the overall rate of a fermentation process to generate the desired product.

Hydrolysis of the lignocellulosic biomass releases variety of sugars, including hexoses (e.g., glucose, mannose), pentoses (e.g., xylose, arabinose), and oligosaccharides, that are released by the hydrolysis of lignocellulosic biomass, and no single microorganism is capable of fermenting all these sugars. Many ethanologenic microbes, including yeast, prefer to use glucose as a substrate. Even when yeast cells are modified genetically to use xylose, they ferment all glucose before switching to the much slower xylose fermentation. Conversion rates can vary greatly depending on such factors as the type of sugar substrate being fermented, environmental conditions (e.g., pH, temperature), and the concentrations of certain products from other metabolic pathways.

The fraction of pentose sugars which compose biomass can significant; for example, 12% pentose sugars have been reported for *Pinus* spp. and 26% for *Populus* spp. (Saddler and Mackie, 1990, *Biomass* 22:293). Acid/enzymatic hydrolysis of agricultural materials also generates a significant fraction of pentoses. For example, hydrolysis of peanut hulls results in a mixture containing 44% pentoses (Chandrakant and Bisaria, 2000, *Appl. Micro. Biotechnol.* 53:301). In order to achieve high yields and productivities, both pentose and hexose fractions must be fully and efficiently utilized. Complicating the matter is the fact that hydrolysis also leads to the formation of acetic acid, which is a known inhibitor to any of the microorganisms that might be used to ferment these sugars into products such as ethanol.

The efficient conversion of both pentoses and hexoses is a significant hurdle to the economic utilization of biomass hydrolysates for the generation of any fermentation product. The central problem is that either the microorganism used to metabolize the sugars in the mixture consumes the sugar constituents sequentially (e.g., first glucose and then xylose) or the organism is unable to utilize the pentose at all (as is the case with the yeast, *Saccharomyces cerevisiae*). In a recent comprehensive review Zaldivar et al. succinctly conclude "the lack of a microorganism able to ferment efficiently all sugars released by hydrolysis from lignocellulosic materials has been one of the main factors preventing utilization of lignocellulose" (Zaldivar et al., 2001, *Appl. Microbiol. Biotechnol.* 56:17).

Current strategies have focused on the development of a single organism engineered to metabolize both hexoses and pentoses, a single organism that "can do it all." For example, the common yeast *Saccharomyces cerevisiae*, the most widely used organism for ethanol production from starch-based crops, has been genetically modified to metabolize xylose as well as its native substrate glucose. Genes encoding xylose reductase, xylitol dehydrogenase and xylulokinase fused to glycolytic promoters have been successfully integrated into the yeast chromosome (Ho et al., 1998, *Appl. Env. Micro.* 64:1852.; Sedlak et al., 2003, *Enzyme Micro. Technol.* 33:19.). In another study, *S. cerevisiae* genetically engineered to contain genes to metabolize xylose still consumed less than 25% of the xylose when glucose was depleted (Sedlak et al., 2003, *Enzyme Micro. Technol.* 33:19.). Even when xylose isomerase activity was added to *S. cerevisiae* to convert xylose to glucose extracellularly, 75% of the xylose still remained after the glucose was completely consumed (Chandrakant and Bisaria, 2000, *Appl. Micro. Biotechnol.* 53:301.).

Bacteria are also frequently used for fermentation processes, but are unable to efficiently metabolize sugar mixtures. In many bacteria, the metabolism of glucose prevents efficient xylose consumption and as a result many researchers have attempted to improve the efficiency of xylose consumption. Introducing a mutation into the ptsG gene of *Escherichia coli* can reduce glucose-mediated repression of xylose consumption (Dien et al., 2002, *J. Industr. Micro.* 29:221.). For example, in batch culture with the ethanologenic *E. coli* strain KO11 grown on hemicellulose hydrolysate, for example, only 11% of the xylose was consumed after 24 h, while 80% of the glucose was consumed (Barbosa et al., 1992, *Appl. Env. Micro.* 58:1382.). Removal of the ptsG improved xylose consumption in the presence of glucose, but still 40% of the xylose remained when the glucose is depleted (Dien et al., 2002, *J. Industr. Micro.* 29:221.).

Approaches using "evolutionary engineering" have also significantly improved the rate of xylose consumption (Kuyper et al., 2005, *FEMS Yeast Res.* 5:925), but have not prevented the diauxic behavior when using sugar mixtures (i.e., first glucose consumption, then xylose). Likewise, introduction of genes involved in the xylose metabolism pathway into *Zymomonas mobilis* does not prevent it from consuming xylose much more slowly than glucose (Zhang et al., 1995, *Science* 267:240). Because both sugars are not consumed effectively in any of these single-organism processes, the productivity of the process is suboptimal.

Strategies which require a single organism to convert xylose and glucose suffer from several limitations. First, as noted above, the consumption of the sugars is asynchronous. Despite the presence of the genetic apparatus to consume both sugars, glucose remains the preferred substrate, and xylose invariably remains when glucose has been consumed. This asynchronicity particularly influences a single microorganism's ability to cope well with a real hydrolysate having a temporally varying concentration of each sugar. Faced with a time-varying stream, yet using a single organism which has a limited ability to adjust its ratio of glucose and xylose consumption rates, the process will invariably lead to one of the sugars not being effectively consumed. It is not currently possible for one organism to "adjust" its rate of consumption to two substrates in order to match the concentrations encountered in a real process.

A second shortcoming is that a single microorganism strain, which has been engineered to consume both glucose and xylose, tends to be unstable. A study using a chemostat demonstrated that the presence of both sugars caused an increase over time in the by-product (and inhibitor) acetic acid, which ultimately led to a 20% decrease in ethanol yield (Dumsday et al., 1999, *J. Indust. Micro. Biotechnol.* 23:701).

This highlights another complication: hydrolysis of real biomass typically generates compounds which inhibit the subsequent conversion of sugars by fermentation. For example, xylose is acetylated in lignocellulose (Timmel, 1967, *Wood Sci. Technol.* 1:45; Chesson et al., 1993, *J. Sci. Food Agric.* 34:1330), and therefore acetic acid is an unavoidable product of hemicellulose depolymerization. Although the inhibitory effect of acetic acid depends on the strain and process, an acetic acid concentration of only 0.08% has been demonstrated to inhibit a subsequent fermentation to generate ethanol (van Zyl et al., 1991, *Enzyme Micro. Technol.* 13:82). Generally acetic acid inhibits xylose conversion more than it affects glucose conversion. In *S. cerevisiae* engineered to metabolize xylose, for example, acetic acid reduced ethanol yield from xylose by 50% (Helle et al., 2003, *Enzyme Microbial Technol.* 33:786). Acetic acid itself, and not merely the pH, causes the inhibition. Therefore, base neutralization traditionally applied to acid treated lignocellulosic hydrolysates does not eliminate the inhibitory affects of acetic acid. Previous approaches to convert this mixture of sugars and inhibitors have not been able to achieve the rate of conversion necessary to make the process economically viable. A novel approach that successfully overcomes the inability to convert a mixture of sugars and inhibitors and increases the yields of fermentation product per amount of biomass would represent a significant and long awaited advance in the field.

SUMMARY OF THE INVENTION

In one aspect, the invention provides a method for producing a biochemical that includes concurrently contacting an organic material, preferably an organic material that contains a mixture of sugars, such as a lignocellulosic hydrolysate, with a plurality of sugar-selective cells under conditions to allow the plurality of sugar-selective cells to produce the biochemical. The method optionally includes the additional steps of hydrolyzing a biomass, such as a lignocellulosic biomass, to produce the hydrolyzed biomass, such as a hydrolyzed lignocellusosic biomass, and/or purifying the resulting biochemical product. Exemplary biochemicals that can be produced using the method of the invention include ethanol, butanol, succinate, lactate, fumarate, pyruvate, butyric acid and acetone.

The plurality of sugar-selective cells may include at least one hexose-selective cell and at least one pentose-selective cell. Preferably, the plurality of sugar-selective cells includes first and second sugar-selective cells. The first sugar-selective cell metabolizes a first sugar that cannot be metabolized by the second sugar-selective cell. The second sugar-selective cell metabolizes a second sugar that cannot be metabolized by the first sugar-selective cell. These first and second sugars are different, and are preferably selected from the group consisting of glucose, xylose, arabinose, galactose, or mannose. More preferably, at least one of the sugar-selective cells cannot metabolize at least of those two sugars, more preferably at least three of those sugars. In an even more preferred embodiment, at least one of the sugar-selective cells can metabolize only one sugar that is independently selected from the group consisting of glucose, xylose, arabinose, galactose, and mannose.

The sugar selective cells are preferably single-celled microorganisms, such as yeast or bacteria. Cells suitable for use in the method include cells of *Escherichia coli, Zymomonas mobilis, Corynebacterium glutamicum*, Lactic Acid Bacteria, *Saccharomyces cerevisiae, Pichia stipitis* and *Ambrosiozyma monospora*. In a preferred embodiment, the plurality of cells includes a first *E. coli* cell wherein at least one gene involved in glucose metabolism has been modified or deleted so as to inhibit or prevent the first *E. coli* cell from consuming glucose; and a second *E. coli* cell wherein at least one gene involved in xylose metabolism has been modified or deleted so as to inhibit or prevent the second *E. coli* cell from consuming xylose.

Optionally, when the method of the invention is used to produce ethanol, the plurality of sugar-selective cells includes at least one cell that has been genetically engineered for enhanced ethanol production.

Production of the biochemical can also optionally be enhanced when at least one of plurality of sugar-selective cells has been genetically engineered to express or overexpress at least one enzyme selected from the group consisting of an alcohol dehydrogenase enzyme and a pyruvate decarboxylase enzyme.

Some embodiments of the method of the invention make use of an inhibitor-selective cell to metabolize one or more inhibitors, such as acetic acid, furfural and hydroxymethyl furfural (HMF), commonly found in lignocellulosic hydrolysates. The sugar-containing organic material or biomass, such as the lignocellulosic hydrolysate, is contacted with at least one inhibitor-selective cell under conditions to allow the inhibitor-selective cell to metabolize the inhibitor. Preferably, the inhibitor-selective cell converts the inhibitor into the desired biochemical. Contact of the inhibitor-selective cell with the sugar-containing organic material, such as the lignocellulosic hydrolysate, can occur prior to contacting the sugar-containing organic material, such as the hydrolysate, with the plurality of sugar-selective cells, as part of a two stage process, or concurrent with contacting the hydrolysate with the plurality of sugar-selective cells, as part of a single stage process.

The inhibitor-selective cell is preferably a bacteria or yeast, more preferably an *E. coli* cell, wherein at least one gene involved in glucose metabolism has been modified or deleted so as to inhibit or prevent the cell from consuming glucose, and at least one gene involved in xylose metabolism has been modified or deleted so as to inhibit or prevent the cell from consuming xylose. More preferably, the inhibitor-selective cell has been genetically engineered such that it cannot metabolize any sugar selected from the group consisting of glucose, xylose, arabinose, galactose and mannose.

More generally, the invention provides a method for producing a biochemical that includes concurrently contacting an organic material with a plurality of substrate-selective cells under conditions to allow the plurality of substrate-selective cells to produce the biochemical. The substrates for which the cells are selective can include any carbon substrate, including but not limited to sugars, inhibitors, hydrocarbons and the like. In an exemplary embodiment, the plurality of substrate-selective cells includes at least one sugar-selective cell and at least one inhibitor-selective cell.

In another aspect, the invention provides a method for removing acetate from a mixture, such as organic material, biomass, or a lignocellulosic hydrolysate, that includes acetate as well as one or more sugars, such as glucose and xylose. The mixture is contacted with an acetate-selective cell, preferably an *E. coli* cell, under conditions to allow the acetate-selective cell to consume acetate. Preferably, at least one gene involved in glucose metabolism, as well as at least one gene involved in xylose metabolism, have been modified or deleted from the acetate-selective cell so as to inhibit or prevent the cell from consuming glucose and xylose. More preferably, the acetate-selective cell has been genetically engineered such that it cannot metabolize any sugar selected from the group consisting of glucose, xylose, arabinose, galactose and mannose. The acetate-selective cell preferably produces a biochemical selected from the group consisting of ethanol, butanol, succinate, lactate, fumarate, pyruvate, butyric acid and acetone.

In another aspect, the invention provides a method for converting a sugar-containing organic material, such as a biomass, preferably a lignocellulosic hydrolysate, into a biochemical using a two stage process. In a first stage, an organic material, such as a biomiass, preferably a lignocellulosic hydrolysate, comprising at least one inhibitor and a plurality of sugars is contacted with at least one microorganism that can only consume an inhibitor, to yield a detoxified hydrolysate. In the second stage, the detoxified hydrolysate is contacted with a plurality of microorganisms, wherein each microorganism independently consumes only one sugar in the hydrolysate, under conditions to allow the plurality of microorganisms to produce the biochemical.

It should be understood that the invention encompasses not only the methods described herein, but also, without limitation, the substrate-selective cells, and compositions including such substrate-selective cells, as described herein for use in the methods of the invention. For example, the invention includes an acetate-selective cell, preferably an *E. coli* cell, in which at least one gene involved in glucose metabolism has been modified or deleted so as to inhibit or prevent the cell from consuming glucose, and a modification or deletion of at least one gene involved in xylose metabolism so as to inhibit or prevent the cell from consuming xylose. Preferably the acetate-selective cell has been genetically engineered such that it cannot metabolize any sugar selected from the group consisting of glucose, xylose, arabinose, galactose and mannose.

Other exemplary compounds include, but are not limited to, a genetically engineered microorganism that cannot utilize either glucose or xylose as a carbon source, wherein the corresponding wild-type microorganism utilizes both glucose and xylose as a carbon source. Also included is a genetically engineered microorganism that cannot utilize either glucose or arabinose as a carbon source, wherein the corresponding wild-type microorganism utilizes both glucose and arabinose as a carbon source. Preferably the microorganism is an *E. coli, Z. mobilis, C. glutamicum*, Lactic Acid Bacteria, *S. cerevisiae, P. stipitis* or *A. monospora*. The invention further includes a genetically engineered bacterium that cannot utilize either glucose or xylose as a carbon source. The invention further encompasses a genetically engineered bacterium that cannot utilize either glucose or arabinose as a carbon source. Also included is a genetically engineered bacterium that cannot utilize either glucose or galactose as a carbon source. Preferably the bacterium is an *E. coli, Z. mobilis, C. glutamicum*, or Lactic Acid Bacteria.

Yet other exemplary compounds included *Pichia stipitis* that cannot utilize either glucose or xylose as a carbon source; *Pichia stipitis* that cannot utilize either glucose or arabinose as a carbon source; *Ambrosiozyma monospora* that cannot utilize either glucose or xylose as a carbon source; and *Ambrosiozyma monospora* that cannot utilize either glucose or arabinose as a carbon source.

The invention further includes a composition comprising first and second sugar-selective cells, wherein the first sugar-selective cell metabolizes a first sugar that cannot be metabolized by the second sugar-selective cell, and the second sugar-selective cell metabolizes a second sugar that cannot be metabolized by the first sugar-selective cell, and wherein the first and second sugars are independently selected from the group consisting of glucose, xylose, arabinose, galactose, and mannose. Preferably, at least one of the sugar-selective cells can metabolize only one sugar independently selected from the group consisting of glucose, xylose, arabinose, galactose, and mannose. Optionally the composition further includes an inhibitor-selective cell, preferably an inhibitor-selective cell that has been genetically modified such that it cannot metabolize any sugar selected from the group consisting of glucose, xylose, arabinose, galactose and mannose. Preferred sugar-selective cells include *E. coli, Z. mobilis, C. glutamicum*, Lactic Acid Bacteria, *S. cerevisiae, P. stipitis* and *A. monospora*. Optionally, at least one of the sugar-selective cells has been genetically engineered for enhanced ethanol production. Also optionally, at least one of the sugar-selective cells has been genetically engineered to express or overexpress at least one enzyme selected from the group consisting of an alcohol dehydrogenase enzyme and a pyruvate decarboxylase enzyme. The composition optionally further includes a biomass component such as a lignocellulosic hydrolysate.

Also included in the invention is a composition that includes a plurality of microorganisms of the same species, wherein each microorganism independently utilizes only one sugar, such as glucose, xylose, arabinose, galactose, and mannose, that is present in a biomass such as a lignocellulosic hydrolysate. Preferred microorganisms include bacteria and yeast.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims. Unless otherwise specified, "a," "an," "the," and "at least one" are used interchangeably and mean one or more than one.

For any method disclosed herein that includes discrete steps, the steps may be conducted in any feasible order. And, as appropriate, any combination of two or more steps may be conducted concurrently.

It is to be understood that the terms used herein to describe acids (for example, the term acetate) are not meant to denote any particular ionization state of the acid, and are meant to include both protonated and unprotonated forms of the compound. Thus, the terms acetate and acetic acid refer to the same compound and are used interchangeably.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
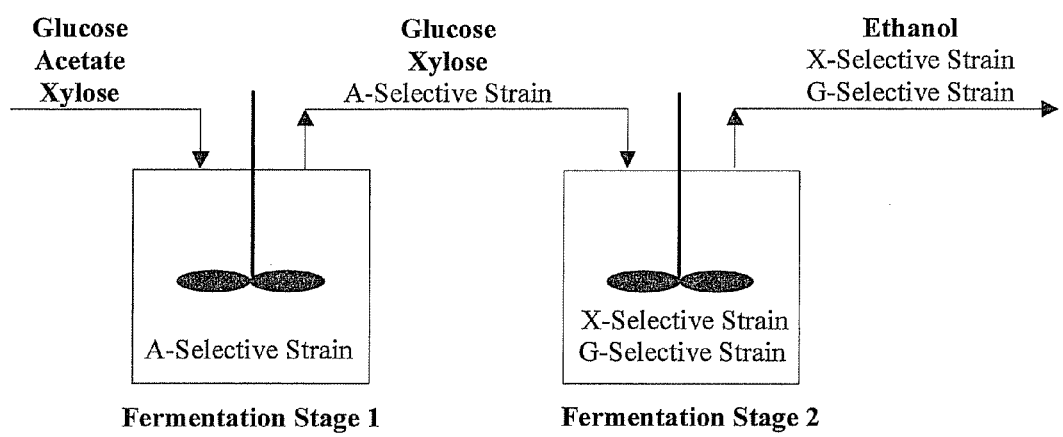
FIG. 1 shows a two-step process to a) consume inhibitor acetic acid and b) to convert xylose and glucose concurrently into a desired product.

The present invention provides a novel biological method that permits efficient conversion of a complex organic material to a desired biochemical product. The method of the invention allows multiple sugars in a complex mixture to be consumed concurrently and independently. Each sugar is converted into the desired product at relatively high yield, and the process can adapt to fluctuating sugar concentrations without leading to the accumulation of any one sugar. Moreover, as described further below, the method can readily be extended to remove inhibitory compounds from hydrolysates.

The complex organic material that serves as the "input" for the method of the invention is preferably a biomass, more preferably a lignocellulosic biomass. The term "biomass" can include any plant, vegetation, or waste product that can be used as a fuel or used as an energy source. Cellulosic or lignocellulosic biomass is typically a plant biomass composed of cellulose, hemicellulose and/or lignin, often with smaller amounts of proteins, lipids (fats, waxes and oils) and ash. It should be noted that the terms "cellulosic biomass" and "lignocellulosic biomass" are used interchangeably herein. In some cellulosic biomasses, roughly two-thirds of the dry mass of cellulosic materials are present as cellulose and hemicellulose. Lignin makes up the bulk of the remaining dry mass. Cellulosic biomass feedstocks include agricultural plant wastes (e.g., corn stover, leaves and stalks, cereal straws, sugarcane bagasse), plant wastes from industrial processes (e.g., wood residues, sawdust, paper pulp, wood chips, municipal paper waste) and energy crops grown specifically for fuel production, such as switchgrass. The method of the invention can also be practiced using crops and feedstocks such as corn, sugarcane, wheat or barley, and grasses such as switchgrass and hemp. Any organic material that contains a plurality of sugars, whether naturally occurring or synthesized, can serve as the "input" for the method of the invention. Preferably, the organic material, such as the biomass, is hydrolyzed. The principal monomeric sugars found in the lignocellulosic hydrolysate are glucose, xylose, mannose, galactose and arabinose. These sugars have been found up to the following percentages in various lignocellulosic hydrolysates: arabinose, 17%; galactose, 15%; glucose, 50%; mannose, 36%; xylose, 74%.

The organic material is converted into the desired biochemical product or products (the "outputs" of the method) by way of a biological process. Efficient conversion of inputs to desired outputs is accomplished by utilizing a plurality of genetically engineered "substrate-selective" cells, each of which has been independently metabolically engineered to result in enhanced consumption of one particular substrate in relation to another, as described in more detail below. Examples of biochemical products include, but are not limited to, ethanol, butanol, succinate, lactate, fumarate, pyruvate, butyric acid and acetone. Other biochemicals that can be produced using the biological method of the invention include lysine, gluconate, citrate, malate, and whole-cell yeast biomass. Preferably, the method of the invention produces ethanol.

Importantly, the invention does not rely on a single organism to accomplish all the process design goals required for biomass, e.g., lignocellulosic conversion; rather, multiple microbial strains are used to accomplish tasks efficiently and independently. Note that competition is minimized or preferably absent in the co-culture contemplated by the invention. Competition involves multiple species competing for the same substrate. In the present invention, the strains each "seek" only their specific substrate or substrates. Thus, the various shortcomings which result from competition found in a traditional "mixed-culture" bioprocess are reduced or avoided. The present invention can be viewed as an engineered microbial system. Additionally, our approach should not be confused with "classic consortium" strategies which involve using different organisms, such as using mixed cultures of *P. stipitis* and *S. cerevisiae*, to make ethanol. The problem with these classic consortium strategies is that the different microorganisms affect each other's growth, and the system cannot be controlled if one strain still consumes multiple sugars. Because the strains used in the substrate-selective consortium approach of the invention are substrate-selective and preferably isogenic, the problems associated with using different species or genera are reduced or avoided.

In one embodiment, the method of the invention encompasses concurrently contacting an organic material, preferably a hydrolyzed biomass, with a plurality of substrate-selective cells, under conditions to allow formation of a desired product. The organic material is preferably mixed with two or more different substrate-selective cells at the same time, in a co-culture, in a single bioreactor. The plurality of substrate-selective cells preferably includes at least one, preferably at least two, cells that are selective for sugars (sugar-selective cells). Preferably, the sugar-selective cells include at least one hexose-selective (HSC), at least one pentose-selective cell (PSC), or a combination thereof. In a particularly preferred embodiment, the method of the invention concurrently utilizes at least one hexose-selective cell and at least one pentose-selective cell.

Optionally, the method of the invention further includes the use of at least one substrate-selective cell that is an inhibitor-selective cell (ISC). The inhibitor-selective cell can be contacted with the hydrolyzed biomass either prior to, or concurrently with, contacting the biomass with the plurality of sugar-selective cells.

In another embodiment, the invention encompasses contacting a hydrolyzed biomass with at least one sugar-selective cell and at least one inhibitor-selective cell, under conditions to allow formation of a desired product. Contacting the hydrolyzed biomass with the different substrate-selective cells can occur concurrently or sequentially. If sequential, the hydrolyzed biomass is preferably first contacted with the inhibitor-selective cell.

A hexose-selective cell used in the method of the invention is preferably a glucose-selective cell, but can include any other hexose-selective cell such as cells that are selective for glucose, mannose, galactose, allose and fructose. A pentose-selective cell used in the method of the invention is preferably a xylose-selective cell, but can include any other pentose-selective cell such as cells that are selective for xylose, arabinose, ribose, and ribulose.

A preferred inhibitor-selective cell for use in the method of the invention is preferably an acetate-selective cell (ASC). Acetate consumption in *E. coli* is mediated by acetyl CoA synthase (acs), isocitrate lyase (aceA), malate synthase (aceB), acetate kinase (ackA) and isocitrate dehydrogenase (icdA). Many other organisms *Saccharomyces cerevisiae* and *Pseudomonas* spp., *Pichia stipitis, Bacillus cereus*, have at least some of these enzymes to degrade acetate however it should be noted that the names of the genes are usually different. For example, in *S. cerevisiae* the gene encoding for isocitrate lyase is named ICL1. A preferred acetate-selective bacterial cell has deletions in genes involved in the uptake of the all the competing substrates: glucose, mannose, galactose, xylose and arabinose. To that end, the genes manZ, ptsG, glk, xylA, galK, araA are preferably knocked out to yield an acetate-selective cell. Optionally, other genes involved in one or more bacterial phosphotransferase systems (PTS) are knocked out to yield the acetate-selective cell, for example malX from the maltose PTS, fruA andfruB from the fructose specific PTS, the bgl operon (including but not limited to bglF, bglC, bglS and bglB), and the crr gene. The crr (carbohydrate repression resistance) gene is also known as PTS enzyme IIAGlc. Crr is an important component in glucose uptake through the well-characterized phosphoenolpyruvate:carbohydrate phosphotransferase system, functions a phosphocarrier for glucose transport, and can regulate rpoS expression. A particularly preferred acetate-selective cell is one containing knockouts of at least manZ, ptsG, glk, xylA, and crr.

To our surprise, *Pseudomonas* was found to grow particularly well on acetate and thus is a preferred for use as an acetate-selective cell.

Optionally, an inhibitor selective cell can be engineered to consume two different inhibitors, such as both acetate and furfural. Alternatively, a plurality of inhibitor selective cells can be utilized in the method of the invention. For example, two different inhibitor selective cells, one that is selective for acetate, and another that is selective for furfural, can used in the method of the invention. The acetate-selective strain would consume acetate and not furfural (i.e., it is engineered such that it lacks one or more furfural degradation genes), and the furfural-selective strain would consume furfural and not acetate, for example by knocking out the acetate degradation genes acs and ackA.

As described in more detail below, the inhibitor-selective cell can be contacted with the hydrolyzed biomass either prior to, or concurrent with at least one, preferably at least two, sugar-selective cells.

It should be understood that the terms "substrate-selective cell," "sugar-selective cell," "hexose-selective cell," "pentose-selective cell," "inhibitor-selective cell," "glucose-selective cell," "xylose-selective cell," "acetate-selective cell," and the like are not intended to refer to just a single, physical cell, but include many such cells, as in a typical cell culture. Thus, a mixture according to the invention that contains, for example, one "xylose-selective cell" and one "glucose-selective cell" means a co-culture of xylose-selective cells and glucose-selective cells. Likewise, a mixture that contains two "hexose-selective cells" means a co-culture of first hexose-selective cells (e.g., glucose-selective cells) and second (different) hexose-selective cells (e.g., galactose-selective cells).

The invention includes not only a method of producing a desired product from a biomass using a plurality of substrate-selective cells, but also the various substrate-selective cells, alone or in combination, as described herein. More particularly, the invention includes a composition that includes a plurality of substrate-selective cells and, optionally, a biomass, such as a lignocellulosic biomass or hydrolysate.

Cells

Cells useful in the method of the invention include animal, plant, yeast, protozoan, and bacterial cells. Bacterial cells and yeast cells are in common use for large-scale industrial fermentations and are preferred. Examples of preferred bacterial cells for use in the method of the invention include *Escherichia coli, Zymomonas mobilis, Corynebacterium glutamicum*, Lactic Acid Bacteria such as *Lactobacillus* or *Lactococcus, Pseudomonas* spp. and *Bacillus* spp. such as *B. subtilis* and *B. cereus*. Lactic Acid Bacteria have several characteristics which make them well suited for the biological production of biochemical products. They are natively tolerant of the low pH levels, increased temperatures, and ethanol concentrations of hydrolysates, and are therefore less susceptible than other bacteria to fermentation inhibition. Preferred yeast cells include *Saccharomyces cerevisiae, Pichia stipitis* and *Ambrosiozyma monospora*. While cells of single cell microorganisms such as bacteria, yeast and protozoa are preferred, the method can also be practiced using animal or plant cell cultures derived from multicellular organisms.

Substrate Selectivity

Metabolic engineering involves the targeted and purposeful alteration (using genetic engineering techniques) of an organism's metabolic pathways to redesign them to utilize different proportions or combinations of substrates, or to produce different proportions or combinations of products. In broad terms, metabolic engineering encompasses genetically overexpressing particular enzymes at selected points in a metabolic pathway, and/or blocking the synthesis of other enzymes, to overcome or circumvent metabolic "bottlenecks." A goal of metabolic engineering is to optimize the rate and conversion of a substrate into a desired product.

The present invention employs a plurality of genetically engineered microorganisms which overcomes the numerous limitations currently encountered in the field when utilizing a single microorganism. Cells useful in the present invention have been metabolically engineered to result in enhanced consumption of one particular substrate in relation to another. At least one metabolic pathway of the cells has been disrupted or altered. In the context of the present invention, disruption or alteration of a metabolic pathway encompasses disruption in the cellular process for uptake of the substrate from the extracellular environment that reduces or eliminates the ability of the cell to internalize the substrate, as well as a disruption or alteration of an intracellular process involve in the utilization of the substrate. In short, the cells used in the invention are metabolically engineered to be "substrate-selective."

A cell is "substrate-selective" when it preferentially utilizes a single organic substrate as a carbon source. Carbohydrates (sugars) represent the most common carbon substrates utilized by bacteria and yeast, but many other organic substrates can be used as carbon sources including hydrocarbons, lipids, proteins, and small organic molecules such as acids, esters and the like. It should be understood that substrate-selective cells of the invention include cells that have been engineered to preferentially utilize a particular sugar, inhibitor molecule, hydrocarbon or any other carbon source, without limitation. Such cells are readily identified, designed and selected for use in the method of the invention by one of skill in the art based upon the composition of the organic material to be metabolized, and the nature of the desired product.

One way a cell can be made substrate-selective for a particular substrate is by modifying it, typically through genetically engineering, to reduce or eliminate the cell's ability to metabolize at least one competing substrate. For example, a cell that selectively metabolizes glucose can be made by reducing or eliminating the metabolism of any or all competing substrates such as xylose, galactose, and arabinose. More specifically, a cell that normally consumes both glucose and xylose can be made glucose-selective by reducing or eliminating the cell's ability to metabolize xylose, and xylose-selective by reducing or eliminating the cell's ability to metabolize glucose. Likewise, a cell that normally consumes glucose, xylose and arabinose can be made glucose-selective by reducing or eliminating xylose metabolism, arabinose metabolism, or, preferably, both; can be made xylose-selective by reducing or eliminating arabinose metabolism, glucose metabolism, or, preferably both; and can be made arabinose-selective by reducing or eliminating glucose metabolism, xylose metabolism, or, preferably, both. More generally, if a cell can metabolize n sugars (where n>1), the cell can be made selective for a particular sugar by reducing or eliminating the metabolism of at least 1 other sugar, up to n−1 other sugars in the most preferred embodiment. A plurality of sugar-selective cells useful in the method of the invention thus includes at least a first sugar-selective cell that metabolizes a first sugar that cannot be metabolized by a second sugar-selective cell, and a second sugar-selective cell that metabolizes a second sugar that cannot be metabolized by the first sugar-selective cell.

These genetic modifications preferably result in a strain that will only utilize a selected sugar (such as glucose, xylose, arabinose, galactose) or inhibitor (such as acetic acid or a furfural), a strain that can be considered to have "substrate-selective uptake" since it is selective in what compound it is able to consume. For example, by deleting a key gene in the xylose uptake pathway, a strain of bacteria is constructed which is unable to consume xylose, thereby allowing glucose to serve as the specified substrate. Placed in a fermenter containing xylose and glucose, such a strain would leave the xylose unutilized and be completely unaffected by the presence of xylose. Similarly, a strain can be constructed which is unable to consume glucose. Placed in a fermenter with xylose and glucose, such a strain would be unable to utilize the glucose, and thereby consume only xylose.

Example 16 shows a preferred substrate selective cell that has been engineered to selectively metabolize xylose and/or arabinose in the presence of glucose.

Advantageously, a substrate-selective cell functions independently of other (different) substrate-selective cells, as well as independently of other substrates present in the mixture. Placed together in co-fermentation in a fermenter containing glucose and xylose, each strain would be expected to act optimally on just one of these sugars and be unaffected by the presence of the other sugar or the other organism. For example, a glucose specific microorganism could be engineered by eliminating the pathways necessary for metabolism of arabinose, galactose and xylose.

Additionally, as discussed in more detail below, the metabolic pathways of each strain could be further engineered to optimize yield and productivity of a particular product, such as ethanol.

A reduction or elimination in the cell's ability to metabolize a particular substrate can be detected in any convenient manner. For example, if a gene has been physically disrupted, e.g., by mutagenesis, deletion, or the like, the disruption can be detected using DNA sequencing or other routine DNA detection procedures. Phenotypically, a reduction or elimination in the cell's ability to metabolize a particular substrate can be detected by comparing the cell's metabolic behavior relative to a mixture of sugars before and after the modification. If the metabolism of at least one sugar is essentially unchanged, but with respect to a second sugar if that sugar is metabolized slower or not at all, one can conclude that there has been a reduction or elimination of the cell's ability to metabolize the second sugar.

Preferably, the pathway(s) for metabolizing one or more competing substrates in the substrate-selective cell is/are completely disrupted (e.g., via a "knockout" of an essential gene), such that the competing substrate or substrates otherwise metabolized by the cell are not metabolized at a detectable level. A knockout of a competing metabolic pathway can be accomplished by modifying or deleting one or more genes involved in metabolizing the competing substrate, as necessary, so as to inhibit or prevent the cell from metabolizing the competing substrate.

Methods of disrupting or altering metabolic pathways in bacteria, plants, and animals to reduce or eliminate a cell's ability to metabolize at least one carbon substrate are routine and well known in the art. Once a molecular target involved in the substrate's metabolism has been identified, disruption of a metabolic pathway can be effected at any level of gene expression (e.g., DNA replication, transcription or translation), or post-translationally. For example, enzymatic function can be inhibited when the enzyme is targeted by a molecular inhibitor, such as an antibody or a small molecule inhibitor. Translation of an RNA message into an enzyme can be disrupted, for example, by introducing a small interfering RNA, a short-hairpin RNA, or a hybridization probe into the bacteria, plant, or animal cell. Transcription of a gene encoding an enzyme can be disrupted, for example, by targeting the gene with a molecular inhibitor or physically altering the gene to inhibit, prevent or confound gene replication or transcription. Cells can be metabolically engineered through the introduction of polynucleotides, as well as the directed mutagenesis of coding regions. Common gene disruption techniques include mutagenesis, gene deletion or knock-out, and heterologous gene transformation. Such methods are well known in the art; see, e.g., Sambrook et al, *Molecular Cloning: A Laboratory Manual.*, Cold Spring Harbor Laboratory Press (1989), and *Methods for General and Molecular Bacteriology*, (eds. Gerhardt et al.) American Society for Microbiology, chapters 13-14 and 16-18 (1994).

A particularly useful method for metabolically engineering a substrate-selective cell is to "knock out" an essential gene in the metabolic pathway of a competing substrate. A knock-out technique can be used to render a cell unable to utilize a selected sugar as a carbon source. A bacterial strain that is unable to use glucose as a carbon source can be constructed by knocking out the genes encoding for glucosephosphotransferase (ptsG), mannosephosphotransferase (manZ) and glucokinase (glk) (see Example 1). The resulting strain may still be able to metabolize xylose and other sugars, depending on what other functioning metabolic pathways it contains, but not glucose or mannose.

Molecular Targets for Generating Cells that Cannot Utilize One or More Sugars as a Carbon Source The molecular targets of metabolic engineering that will yield a substrate-selective cell for use in the method of the invention naturally depend on the nature of the organism, as well as the substrate whose metabolism is to be disrupted.

Particularly preferred targets for metabolically engineering cells useful in the method of the present invention are molecules involved in carbohydrate transport and metabolism. A metabolic pathway involved in the metabolism of a selected sugar, for example, can be disrupted by affecting the production or activity of one or more enzymes required, either directly or indirectly, to convert the substrate into the product. Alternatively, knocking out the production of a receptor molecule needed for uptake or transport of the substrate from the extracellular environment also reduces or eliminates a cell's ability to metabolize the substrate.

Constructing Bacterial Strains that are Incapable of Utilizing Specific Sugars

The phosphotransferase systems of bacteria can translocate a wide range of carbon sources into the cytoplasm of bacteria. The overall process can be represented as phosphoenolpyruvate+carbohydrate→pyruvate+carbohydrate-P where the carbohydrate is phosphorylated and translocated across the cytoplasmic membrane so it can be catabolized. There are many phosphotransferase systems which can translocate a wide variety of carbohydrates. While most carbohydrates are translocated by a specific phosphotransferase system (PTS), glucose is unusual in that it can be translocated by any of three different phosphotransferase systems: a glucose-specific glucose PTS that can only translocate glucose, a general glucose PTS that can translocate ribitol, sorbose and other carbohydrates in addition to glucose, and the mannose PTS which can translocate glucose in addition to mannose. Thus to inhibit or prevent a bacterium from being able to utilize glucose as a carbon source, the glucose-specific, the general glucose, and the mannose phosphotransferase systems must all be knocked out. Optionally, one or more additional genes involved in other PTSs can be knocked out to further reduce glucose consumption if desired, for example malX from the maltose PTS, fruA from the fructose specific PTS, the bgl operon, and the crr gene.

Some carbohydrates must enter the cell via a periplasmic binding protein-dependent (BPD) ABC transporter system where the carbohydrate is translocated across the cytoplasmic membrane and subsequently phosphorylated so it can be catabolyzed. The periplasmic BPD ABC transporter systems all utilize a periplasmic binding protein, an inner or cytoplasmic membrane protein and an ATPase protein to facilitate transport.

The sugars that comprise lignocellulosic hydrolysates include arabinose, galactose, glucose, mannose, and xylose. The great majority of bacteria can utilize these sugars as their primary carbon source. *Escherichia coli* as well as many of the Lactic Acid Bacteria can utilize all of these sugars. Bacterial strains that are unable to utilize arabinose, galactose, mannose, and xylose as carbon sources can be constructed by eliminating one gene from the respective sugar pathway as indicated in the following table. The exception is glucose: to construct a bacterial strain that is incapable of utilizing glucose, either the manX, manY or manZ gene must be eliminated in addition to the glk and ptsG genes.

Examples of Pathways for Sugar Utilization in Bacteria

| Enzyme | Gene | Reaction catalyzed | Pathway |
| --- | --- | --- | --- |
| Arabinose utilization | | | |
| Arabinose-Binding Protein | araF | Arabinose transport | Arabinose Uptake |
| Arabinose Transport Membrane Protein | araH | Arabinose transport | Arabinose Uptake |
| Arabinose ATPase Protein | araG | Arabinose transport | Arabinose Uptake |
| Arabinose Isomerase | araA | Arabinose → Ribulose | Arabinose Catabolism |
| Ribulokinase | araB | Ribulose → Ribulose-5-P | Arabinose Catabolism |
| Galactose utilization | | | |
| Galactose Binding Protein | mglB | Galactose transport | Galactose Uptake |
| Galactose Transport Membrane Protein | mglC | Galactose transport | Galactose Uptake |
| Galactose ATPase Protein | mglA | Galactose transport | Galactose Uptake |
| Galactokinase | galK | Galactose → Galactose-1-P | Galactose Catabolism |
| Glucose utilization | | | |
| Glucokinase | glk | Glucose → Glucose-6-P | Glucose Uptake |
| Glucose-phosphotransferase Enzyme II | ptsG | Glucose → Glucose-6-P | Glucose Uptake |
| Mannose PTS Protein IIA(III) | manX | Glucose → Glucose-6-P | Glucose Uptake |
| Mannose-phosphotransferase Enzyme IIB | manZ | Glucose → Glucose-6-P | Glucose Uptake |
| Mannose utilization | | | |
| Mannose PTS Protein IIA(III) | manX | Mannose → Mannose-6-P | Mannose Uptake |
| Pel Protein | manY | Mannose → Mannose-6-P | Mannose Uptake |
| Mannose-phosphotransferase Enzyme IIB | manZ | Mannose → Mannose-6-P | Mannose Uptake |
| Xylose utilization | | | |
| Xylose Proton Symport Protein | xylE | Xylose transport | Xylose Uptake |
| Xylose Isomerase | xylA | Xylose → Xylulose | Xylose Catabolism |
| Xylulokinase | xylB | Xylulose → Xylulose-5-P | Xylose Catabolism |

A cell that cannot utilize glucose as a carbon source can be created, for example, by disrupting the following three genes: ptsG; manZ, manY or manX; and glk. Such a strain will not be able to use mannose, either.

A cell that cannot use xylose as a carbon source can be created, for example, by disrupting one of the following genes: xylA, xylB, or xylE.

A cell that cannot utilize arabinose as a carbon source can be created, for example, by disrupting one of the following genes: araA, araB, araF, araH, or araG.

A cell that cannot use galactose as a carbon source can be created, for example, by disrupting one of the following genes: galK, mglB, mglC, or mglA.

A cell that cannot use mannose as a carbon source can be created, for example, by disrupting one of the following genes: manX, manY or manZ.

Examples of Substrate-Selective Strains Useful in the Method of the Invention Include:
a) glucose-selective strain: mutations in araA galK xylA manZ (rendering the cell unable to utilize arabinose, galactose, xylose or mannose as a carbon source)
b) xylose-selective strain: mutations in ptsG manZ glk araA galK (rendering the cell unable to utilize glucose, mannose, arabinose or galactose as a carbon source)
c) arabinose-selective strain: mutations in ptsG manZ glk xylA galK (rendering the cell unable to utilize glucose, mannose, xylose or galactose as a carbon source)
d) galactose-selective strain: mutations in ptsG manZ glk araA xylA (rendering the cell unable to utilize glucose, mannose, arabinose or xylose as a carbon source)
e) mannose-selective strain: mutations in araA galK xylA (rendering the cell unable to utilize arabinose, galactose, or xylose as a carbon source; this cell can still utilize glucose as a carbon source as well as mannose).

Optionally, substrate selective strains, including sugar-selective strains and inhibitor-selective strains, also include a mutation in the crr gene.

Metabolically engineered substrate-selective strains may be further engineered for accumulation of the desired biochemical. For example, a glucose-selective *E. coli* cell engineered to accumulate pyruvate may contain knockouts of the aceEF pps ldhA poxB pflB arcA atpFH genes, resulting in the accumulation of pyruvate when grown in glucose (Zhu et al., 2008, *Appl. Environ. Microbiol.* 74:6649). Mutations in the arcA and atpFH genes, however, may be omitted from the analogous pentose-selective strain, since pentoses do not provide the cell with as much ATP as glucose, and these two mutations reduce the biomass generation from glucose. A sugar-selective *E. coli* cell engineered to accumulate succinate, on the other hand, may contain knockouts in the pflB, ldhA and ptsG genes and preferably is engineered to express the pyc (pyruvate carboxylase) gene, which is not endogenous to *E. coli* (see Vemuri et al., 2002, *Appl Environ Microbiol.* 68(4):1715-27).

Constructing Yeast Strains that are Incapable of Utilizing Specific Sugars

While many yeasts can utilize all of the sugars found in lignocellulosic hydrolysates, the notable exception is *Saccharomyces cerevisiae* which is unable to use pentose sugars as a carbon source. *S. cerevisiae* lacks several of the key enzymes involved in arabinose and xylose utilization. Yeast strains that are unable to utilize arabinose, galactose, or xylose, can be constructed by eliminating one gene from the respective sugar pathway as indicated in the following table. To construct a yeast strain that is incapable of utilizing glucose, either the HXT1, HXT2, HXT3, HXT4, HXT6, HXT7, and SNF3 genes or the GLK1, HXK1, and HXK2 genes must be eliminated.

Examples of Pathways for Sugar Utilization in Yeast

| Enzyme | Gene | Reaction catalyzed | Pathway |
| --- | --- | --- | --- |
| Arabinose utilization | | | |
| Aldose Reductase | GRE | Arabinose → Arabinitol | Arabinose Catabolism |
| Arabinitol-4-Dehydrogenase | LAD1 | Arabinitol → Xylulose | Arabinose Catabolism |
| Xylulose Reductase | ALX1 | Xylulose → Xylitol | Arabinose Catabolism |
| Xylitol Dehydrogenase | XYL2 | Xylitol → Xylulose | Xylose Catabolism |
| Xylulokinase | XKS1 | Xylulose → Xylulose-5-P | Xylose Catabolism |
| Galactose utilization | | | |
| Galactose Permease | GAL2 | Galactose transport | Galactose Uptake |
| Galactokinase | GAL1 | Galactose → Galactose-1-P | Galactose Catabolism |
| Galactose-1-P Uridyl Transferase | GAL7 | Galactose-1-P → Glucose-1-P | Galactose Catabolism |
| UDP-Glucose-4-Epimerase | GAL10 | UDP-Glucose → UDP-Galactose | Galactose Catabolism |
| Glucose utilization | | | |
| Low-affinity glucose transporter | HXT1 | Glucose transport | Glucose Uptake |
| High-affinity glucose transporter | HXT2 | Glucose transport | Glucose Uptake |
| Low-affinity glucose transporter | HXT3 | Glucose transport | Glucose Uptake |
| High-affinity glucose transporter | HXT4 | Glucose transport | Glucose Uptake |
| High-affinity glucose transporter | HXT6 | Glucose transport | Glucose Uptake |
| High-affinity glucose transporter | HXT7 | Glucose transport | Glucose |

-continued

| Enzyme | Gene | Reaction catalyzed | Pathway |
|---|---|---|---|
| Plasma membrane glucose sensor | SNF3 | Glucose transport | Uptake Glucose |
| Glucokinase | GLK1 | Glucose → Glucose-6-P | Uptake Glucose |
| Hexokinase isoenzyme 1 | HXK1 | Glucose → Glucose-6-P | Uptake Glucose |
| Hexokinase isoenzyme 2 | HXK2 | Glucose → Glucose-6-P | Uptake Glucose |
| Xylose utilization | | | |
| Xylose Reductase | XYLI | Xylose → Xylitol | Xylose Catabolism |
| Xylitol Dehydrogenase | XYL2 | Xylitol → Xylulose | Xylose Catabolism |
| Xylulokinase | XKS1 | Xylulose → Xylulose-5-P | Xylose Catabolism |

A yeast cell that cannot utilize glucose as a carbon source can be created, for example, by disrupting the following three genes: GLK1, HXK1, and HXK2. A yeast cell that cannot utilize glucose as a carbon source can also be created by disrupting the following seven genes: HXT1, HXT2, HXT3, HXT4, HXT6, HXT7, and SNF3.

A yeast cell that cannot utilize arabinose as a carbon source can be created, for example, by disrupting one of the following genes: GRE, LAD1, or ALX1. It is preferable not to delete the XYL2 or XKS1 genes since these genes are also utilized in xylose catabolism.

A yeast cell that cannot utilize galactose as a carbon source can be created, for example, by disrupting one of the following genes: GAL2, GAL1, GAL7, or GAL10.

A yeast cell that cannot utilize xylose as a carbon source can be created, for example, by disrupting one of the following genes: XYL1, XYL2, or XKS1.

Optimization of Ethanol Production

The substrate-selective cell used in the method of the invention includes at least one metabolic pathway for the production of the desired product, for example ethanol. If the native, wild-type cell does not include an ethanol production pathway, genetic engineering can be used to introduce such a pathway so as to render the cell ethanologenic. If the native cell includes an ethanol pathway, the cell can optionally be further metabolically engineered to optimize the ethanol production pathway.

Optionally, the substrate-selective cell of the invention is engineered to overexpress an alcohol dehydrogenase enzyme and/or a pyruvate decarboxylase enzyme. Pyruvate is converted by pyruvate decarboxylase to acetaldehyde, which is subsequently converted to ethanol by alcohol dehydrogenase. In some endogenous bacterial systems, the conversion of pyruvate to ethanol is rate-limiting in the production of ethanol, and results in excess substrate being converted to other byproducts such as acetic acid and succinic acid. The presence of high activities of alcohol dehydrogenase enzyme and pyruvate decarboxylase enzyme effectively increase the organism's ability to produce ethanol in order to maintain high conversion efficiency and minimize the amount of byproduct. One option for introducing these two enzymes into a substrate-selective cell is to transform the cell with a plasmid, such as pLOI308 (Ingram et al., 1987, *Appl. Environ. Microbiol.* 53:2420; Ingram and Conway, 1988, *Appl. Environ. Microbiol.* 54:397), that elevates ethanol formation in *E. coli*. This plasmid uses the *Zymomonas mobilis* pyruvate decarboxylase and alcohol dehydrogenase B genes. Preferably, the cell is transformed with a "production of ethanol" (PET) operon in which the alcohol dehydrogenase gene and the pyruvate decarboxylase gene from *Z. mobilis* have been placed under control of the Lac promoter. When expressed together, alcohol dehydrogenase gene and pyruvate decarboxylase cause ethanol to be the major product of *E. coli* fermentations. Alternatively or additionally, the cell can be transformed with a plasmid, such as pTrc99A-pdc.adhB, which contains pyruvate decarboxylase (pdc) and alcohol dehydrogenase (adh) from *Z. mobilis*.

Alternatively or additionally, ethanol production can be optimized by knocking out by-product pathways in order to guide additional substrates, and force more carbon, into the ethanol production pathway. By-product pathways genes that can be knocked-out in order to enhance ethanol production include, but are not limited to, pyruvate formate lyase, fumarate reductase, and lactate dehydrogenase.

Biological Production of Ethanol and Other Biochemicals

Biological conversion of organic material, such as a biomass, to a desired product, such as ethanol, can involve one or more of the following steps, in any order: harvesting the biomass, performing separation or extraction steps on the biomass, pretreating the biomass, hydrolyzing the biomass, contacting the biomass with substrate-selective cells of the invention under conditions to convert a component of the hydrolysate into a desired product (i.e., fermentation), and subsequent isolation and/or purification of the product.

A biological approach to the production of ethanol typically involves four or five stages. A "pretreatment" phase can be used to make the biomass, including lignocellulosic material such as wood or straw, amenable to hydrolysis. Pretreatment assists in liberating the cellulose from the lignin and makes it more accessible to hydrolysis. Pretreatments are done through physical (mechanical) and/or chemical means. Pretreatment techniques include acid hydrolysis, steam explosion, ammonia fiber expansion, alkaline wet oxidation and ozone pretreatment.

Cellulose and hemicellulose molecules are long chains of sugar moieties. Hydrolysis is used to break down the long molecules in the cellulosic biomass into simple sugars, preferably monomeric sugars, prior to subjecting the mixture to biological conversion of the sugars into the desired products. Hydrolysis can be effected using chemical, physical or enzymatic means. The most commonly used method of chemical hydrolysis is acid hydrolysis. Dilute acid can be used under high heat and high pressure, or more concentrated acid can be used at lower temperatures and pressures. The products from this hydrolysis are neutralized, and microbial fermentation according to the present invention can then be used to produce the desired product, such as ethanol. It should be noted that acid hydrolysis produces several potent inhibitors including acetic acid, furfural and hydroxymethyl furfural (HMF). Advantageously, the mixture can be cleared of inhibitors by contacting it with a cell that is selective for the inhibitor, as a carbon substrate, in accordance with the method of the present invention.

Alternatively or additionally, an enzymatic hydrolysis process can be used. Cellulose chains can be broken into glucose molecules by cellulase enzymes. Biomass, including lignocellulosic biomass can be enzymatically hydrolyzed at a relatively mild condition (50 deg C. and pH5), thus enabling effective cellulose breakdown without the formation of byproducts that would otherwise inhibit enzyme activity.

Optionally, prior to biological fermentation of the mixture in accordance with the invention, the sugars in the hydrolysate are separated from residual materials, such as lignin. At this point the mixture is subjected to biological production of the product(s) using a plurality of substrate-selective cells in accordance with the invention. The resulting product, such as ethanol or lactate, may then be isolated and purified. In methods where ethanol is produced, isolation and purification can be accomplished by distillation.

Biological fermentation, which is sometimes termed "microbial fermentation" when microorganisms are used, yields the desired product, such as ethanol or lactate. It should be noted that the word "fermentation" as used herein is not limited to a strict biochemical meaning of an anaerobic process of converting carbon substrates into acids and alcohols; rather the word "fermentation" is used more broadly as in the art of industrial microbiology, such that it is meant to encompass any large-scale production of biochemicals using microorganisms. As such, a "fermentation" can be either aerobic or anaerobic. Contacting an organic, sugar-containing material, such as a biomass, preferably a lignocellulosic hydrolysate, with the plurality of substrate-selective cells of the invention under conditions to form a selected product is considered herein to be a "fermentation" regardless of whether the process is performed under aerobic or anaerobic conditions.

Biological fermentation, during which substrate-selective cells of the invention are contacted with the biomass hydrolysate under conditions to convert a component of the hydrolysate into a desired product, may take any form, without limitation. For example, it may be a batch fermentation, a fed-batch fermentation, a steady-state fermentation or a continuous fermentation. Fermentation may be done under either aerobic or anaerobic culture conditions, or both in a sequential manner.

Advantageously, use of a plurality of substrate-selective cells allows biological fermentations to be customized in response to the particular composition of the "inputs" or feed. Different feeds, such as crops, wheatgrass, lignocellulosics and other organic material, contain varying compositions of sugars. Volumetric consumption rates for each cell type can be measured and used to effect an "alignment" of consumption rates that permits the most efficient consumption of the available substrates. Optimized utilization of substrates (including sugars and inhibitor compounds) can be achieved by manipulating the timing of the inoculation of one or more of the substrate-selective cells and/or by manipulating the amount or activity (e.g., by upregulating or overexpressing a protein involved in the consumption of the selected substrate) of the inoculum. Use of a fed-batch fermentation system also allows consumption rates for each of the substrate-selective cells to be optimized in response to a particular feed.

In embodiments of the method which do not employ inhibitor-selective cells, biological processing of the hydrolyzed biomass is preferably carried out in a single bioreactor, in a co-fermentation that includes the plurality of sugar-selective cells and the hydrolyzed biomass. The plurality of sugar-selective cells operate independently and concurrently on the hydrolyzed biomass and, as noted elsewhere herein, can be responsive to changes in the relative proportions of the sugars in the fermenter. In embodiments that employ one or more inhibitor-selective cells in addition to sugar-selective cells, either a single stage process (all cells concurrently and independently operating on the biomass in a single bioreactor) or a dual stage process (inhibitor-selective cells operating on the biomass first, followed by contact with the sugar-selective cells) can be used, as set forth in more detail below.

The substrate-selective cells used in a particular stage of the fermentation process according to the invention are preferably either all bacterial cells, or all yeast cells. For example, in a dual stage process as described in more detail below, acetate-selective $E.\ coli$ cells could be used in Stage 1 in a first reactor, followed by a second reactor in Stage 2 containing a collection of yeasts having various sugar-selectivities.

The efficacy of fermentation reactions is further complicated because hydrolysis of organic material continually generates compounds which inhibit the subsequent conversion of organic substrates such as sugars by fermentation. As discussed above, xylose is acetylated in lignocellulose (Timmel, 1967, *Wood Sci. Technol.* 1:45; Chesson et al., 1993, *J. Sci. Food Agric.* 34:1330), and therefore acetic acid, a particularly potent inhibitor of fermentation, is an unavoidable product of lignocellulose hydrolysis. Production of some inhibitors can be reduced by alterations in the hydrolysis process or in the organic material itself (e.g., through genetic engineering). However, it has to date not been feasible to eliminate all inhibitors. Not only must an efficient fermentation system be able to handle a mixture of substrates, but it must also be able to proceed in the fluctuating presence of some inhibitors such as acetic acid without loss of either yield or productivity. Previous approaches to convert mixtures of sugars and inhibitors have not been able to achieve the rate of conversion necessary to make the process economically viable.

Thus, in embodiments of the method of invention that utilize an inhibitor-selective cell (ISC), preferably an acetate-selective cell (ASC), either a single stage or a dual stage (two step) fermentation can be employed.

In a single stage fermentation, the inhibitor-selective cell (e.g., an acetate-selective cell) and at least one, preferably at least two, sugar-selective cells are contacted with the hydrolysate concurrently.

In a dual stage fermentation (FIG. 1), the inhibitor-selective cell is first contacted with the hydrolysate in order to metabolize the acetic acid generated during hydrolysis (Stage 1). The hydrolysate is then contacted with the sugar-selective cells to metabolize the sugar monomers present in the mixture (Stage 2). Advantageously, the inhibitor-selective cells may lyse after the acetate is fully consumed, thereby providing additional nutrients for the sugar-selective cells.

In a process using acetate-selective cells in Stage 1, it is advantageous to maintain Stage 1 as a continuous (or fed-batch) process to maintain a zero acetate concentration as a result of substrate limitation. The process of this continuous process is then matched with Stage 2, which is preferably conducted batch fermentation, linear fed-batch fermentation, or exponential fed-batch fermentation (Example 8). In a preferred embodiment, the two stage process is operates in fed-batch or continuous mode under carbon (i.e., acetate) limitation.

Acetate consumption in Stage 1 is preferably performed under aerobic conditions. Stage 2 can be anaerobic or aerobic, depending on the cells used and the identity of the biochemical being produced. Optimal production of the fermentation product ethanol or lactate, for example, during Stage 2 is preferably accomplished under anaerobic conditions. Thus, when the method of the invention is used to produce ethanol or lactate, a dual stage fermentation may be preferable when an optional inhibitor-selective cell is used.

Optionally, the cultures can be supplemented with additional nutrients in Stage 1, Stage 2, or both; or in the single stage when a single stage process is used.

The utilization of a two stage process that first eliminates the presence of inhibitors, then converts metabolic substrates into the desired fermentation product, increases both the rate of conversion and product yield while leaving little residual biomass hydrolysate unused.

Thus, as summarized above, and as illustrated and described in more detail in the following Examples, the present invention provides a method of concurrent conversion of hexose and pentose sugars which are present in biomass such as lignocellulosic hydrolysates obtained from organic material. The problem is that a single microorganism is unable to metabolize multiple sugars concurrently. Instead, any given microorganism has a complex regulatory network which forces sugars to be metabolized sequentially. This sequential nature invariably reduces the overall rate of a fermentation process to generate the desired product.

Moreover, the fermentation of hexose and pentose sugars is further reduced by inhibitory compounds, such as acetate, which are unavoidable in the hydrolysate. Although the inability of microorganisms to utilize mixed sugars in the presence of acetate is most commonly associated with fuel ethanol production, the formation of other fermentation products (butanol, succinic acid, lactate, pyruvate, fumarate etc.) from biomass hydrolysates would similarly be greatly enhanced by a process that could eliminate acetate and effectively use a multitude of sugars.

Another significant disadvantage in current one-organism processes is that the metabolic pathways to convert glucose into a desired product at optimal yield and productivity do not generally correspond to the metabolic pathways to convert xylose into the same product. Ideally, a process converting xylose and glucose concurrently into a single product would permit these pathways to operate independently of one another, with glucose metabolism not influencing xylose metabolism and vice versa.

The invention thus addresses many of the limitations that have plagued previous attempts to convert lignocellulosic biomass into ethanol and other desired products. The method is able to simultaneously metabolize a variety of organic substrates, thereby eliminating the growth pattern demonstrated by a single microorganism in which it linearly consumes one substrate at a time. Additionally, while employing a number of metabolic alterations that, if made to a single organism, would result in an unstable cell that is prone to spontaneous mutations, these alterations are made in a plurality of different organisms, yielding a highly stable system. Furthermore, each cell within the plurality, by independently metabolizing a specific substrate, is able to fully utilize that substrate resulting in maximum yield of a single metabolic product, whereas a single cell attempting to metabolize a number of different substrates often yields a number of different products. By concurrently metabolizing multiple organic substrates, inhibitors are depleted, production efficiency is improved, and yields of fermentation products are enhanced. The process of the present invention is able to handle varying mixtures of sugars and is also able to contend with the fluctuating presence of some inhibitors such as acetic acid without loss of yield or productivity.

The present invention provides a plurality of cells capable of both eliminating inhibitors and concurrently converting hexose and pentose sugars into a desired fermentation product. The invention is to be broadly understood as including methods of making and using the various embodiments of the metabolically engineered cells of the invention described herein.

The present invention is illustrated by the following examples. It is to be understood that the particular examples, materials, amounts, and procedures are to be interpreted broadly in accordance with the scope and spirit of the invention as set forth herein.

EXAMPLES

Example 1

Co-Fermentation Strategy to Consume Sugar Mixtures Effectively

Introduction

We report a new approach for the simultaneous conversion of xylose and glucose sugar mixtures into products by fermentation (Eiteman et al., 2008, *J. Biol. Engineering*, 2:3). The process simultaneously uses two substrate-selective strains, one which is unable to consume glucose and one which is unable to consume xylose. The xylose-selective (glucose deficient) strain CGSC5457 (ZSC113) has mutations in the glk, ptsG and manZ genes while the glucose-selective (xylose deficient) strain ALS1008 has a mutation in the xylA gene. By combining these two strains in a single process, xylose and glucose are consumed more quickly than by a single-organism approach. Moreover, we demonstrate that the process is able to adapt to changing concentrations of these two sugars, and therefore holds promise for the conversion of variable sugar feed streams, such as biomass sources including lignocellulosic hydrolysates.

The goal of this study was to characterize xylose-selective and glucose-selective strains of *Escherichia coli*. Specifically, we set out to construct *E. coli* strains which independently will only consume xylose or glucose without any loss in consumption rate and which can be used together, acting in concert to consume sugar mixtures effectively.

Materials and Methods

Strains

*Escherichia coli* strains MG1655 (wild-type, F-, λ-) CGSC5457 (ZSC113, lacZ827(UGA) or lacZ82(Am) ptsG22 manZ12 glk-7 relA1 rpsL223(strR) rha-4), DY330 (ΔlacU169 gal490 λcI857 Δ(cro-bioA)), and ALS1008 (MG1655 xylA::Tet) were used in this study. CGSC5457 (ZSC113) was obtained from the *E. coli* Genetic Stock Culture (Yale University). DY330 contains a lambda cI857 lysogen and is used to induce the genes which constitute the lambda Red recombination system (Yu et al., 2000, *Proc Natl Acad Sci USA*. 97:5978).

Generating the xylA::Tet Knockout

The xylA gene which encodes D-xylose isomerase was knocked out using the lambda Red recombination system. Primers were designed which could amplify the tetA gene and promoter from pWM41 (Metcalf et al., 1996, *Plasmid*. 35:1.) bracketed by the first and last 50 bases of the xylA coding sequence. The tetA gene codes for the tetracycline resistance protein. The forward primer 5' ATGCAAGC-CTATTTTGACCAGCTCGATCGCGTTCGT-TATGAAGGCTCAA A<u>ACATCTCAATGGCTAAGGCG</u> 3'

(SEQ ID NO:1) contains the first 50 bases of the xylA coding sequence followed by bases 1349-1368 of TRN10TETR (Accession Number J01830) from pWM41 while the reverse primer 5'TTATTTGTCGAACAGATAATGGTTTAC-CAGATTTTCCAGTTGTTCCTGGC GGCTGGTTTATGCATATCGC(SEQ ID NO:2) 3' contains the last 50 bases of the xylA coding sequence followed by bases 3020-3039 of TRN10TETR from pWM41. The bases from pWM41 are underlined in the primers. The two primers were used to amplify a 1,791 bp fragment from pWM41 DNA using the polymerase chain reaction (PCR) with Pfu polymerase. The resulting DNA was gel-isolated and electroporated into DY330 electrocompetent cells which were prepared as described (Yu et al., 2000, *Proc. Natl. Acad. Sci. USA* 97:5978). Tet(R) colonies were then selected. The presence of the xylA::Tet knockout was confirmed by the inability of DY330 xylA::Tet to grow in minimal xylose media. ALS1008 (MG1655 xylA::Tet) was constructed by transducing xylA::Tet from DY330 xylA::Tet into MG1655 using P1 transduction.

Growth Conditions

For each bioreactor experiment, a single strain was first grown in a tube containing 10 mL BXG medium, then 5 mL transferred to 50 mL BXG medium in a 250 mL shake flask. All flasks were incubated at 37° C. and 250 rpm (19 mm pitch). For those fermentations in which a single strain was used, when the OD of the shake flask culture reached approximately 4, the contents of the shake flask were diluted with BXG medium so that 100 mL having an effective OD of 2.0 was used to inoculate the fermenter. For those experiments in which two strains were used in a single fermentation, the contents of two shake flasks were diluted with BXG medium to 100 mL so that each strain had an effective OD of 2.0 (i.e., in the 100 mL volume). Basal medium contained (per L): 13.3 g $KH_2PO_4$, 4.0 g $(NH_4)_2HPO_4$, 1.2 g $MgSO_4.7H_2O$, 13.0 mg $Zn(CH_3COO)_2.2H_2O$, 1.5 mg $CuCl_2.2H_2O$, 15.0 mg $MnCl_2.4H_2O$, 2.5 mg $CoCl_2.6H_2O$, 3.0 mg $H_3BO_3$, 2.5 mg $Na_2MoO_4.2H_2O$, 100 mg Fe(III)citrate, 8.4 mg $Na_2EDTA.2H_2O$, 1.7 g citric acid, and 0.0045 g thiamine.HCl. BXG medium comprised basal medium with 15 g/L glucose and 8 g/L xylose. Shake flask media were adjusted to a pH or 7.0 with 20% NaOH.

Fermentation

Batch experiments were carried out in a 2.5 L bioreactor (Bioflow 2000, New Brunswick Scientific Co. Edison, N.J., USA) containing 1.0 L BXG medium. Throughout aerobic fermentations, air was sparged into the fermenter at a flowrate of 1.0 L/min, and the agitation was 1000 rpm to ensure no oxygen limitation. In some experiments an anaerobic phase was initiated after aerobic growth. For these cases additional xylose and/or glucose was supplied as reported. To maintain anaerobic conditions, carbon dioxide was provided at a flowrate of 0.2 L/min, and the agitation was 150 rpm.

Fed-batch experiments were carried out in the same vessel initially containing 1.0 L basal medium (no xylose and glucose). Immediately after inoculation, a feed containing a mixture of xylose and glucose without additional medium components commenced as reported. This medium was fed at an exponentially increasing rate designed to achieve a growth rate of 0.1 $h^{-1}$ for a substrate concentration of 30 g/L.

For all fermentations, the pH was controlled at 6.7 using 15% (w/v) $NH_4OH$, and the temperature was controlled at 37° C.

Analyses

The optical density at 600 nm (OD) (UV-650 spectrophotometer, Beckman Instruments, San Jose, Calif.) was used to monitor cell growth, and this value was correlated to dry cell mass. Previously described liquid chromatography methods were used to quantify xylose and glucose (Eiteman et al., 1997, *Anal. Chem. Acta* 338:69) and other organic compounds (Chesson et al., 1993, *J. Sci. Food Agric.* 34:1330).

The fraction of the microbial population that constituted each strain was determined by plating serial dilutions of cultures onto both LB and LB-tetracycline plates.

Results

Aerobic Utilization of Xylose/Glucose Mixtures

*Escherichia coli* ZSC113 and *E. coli* ALS1008 are unable to consume glucose and xylose, respectively. The xylose-selective strain ZSC113 has mutations in the three genes involved in glucose uptake (Curtis and Epstein, 1975 *J Bacteriol.* 122:1189), rendering it unable to consume glucose: ptsG codes for the Enzyme $IICB^{Glc}$ of the phosphotransferase system (PTS) for carbohydrate transport (Postma et al., 1993 *Microbiol Rev.* 57:543), manZ codes for the $IID^{Man}$ domain of the mannose PTS permease (Huber and Erni, 1996, *Eur J Biochem.* 239:810), glk codes for glucokinase (Curtis and Epstein, 1975 *J Bacteria* 122:1189). We constructed strain ALS1008 which has a knockout in the xylA gene encoding for xylose isomerase, rendering ALS1008 unable to consume xylose. In a medium composed of a mixture of these two sugars, ZSC113 would be expected to consume the xylose selectively while ALS1008 should exclusively consume the glucose. We first sought to verify these expectations in three aerobic batch experiments.

Figure 2:
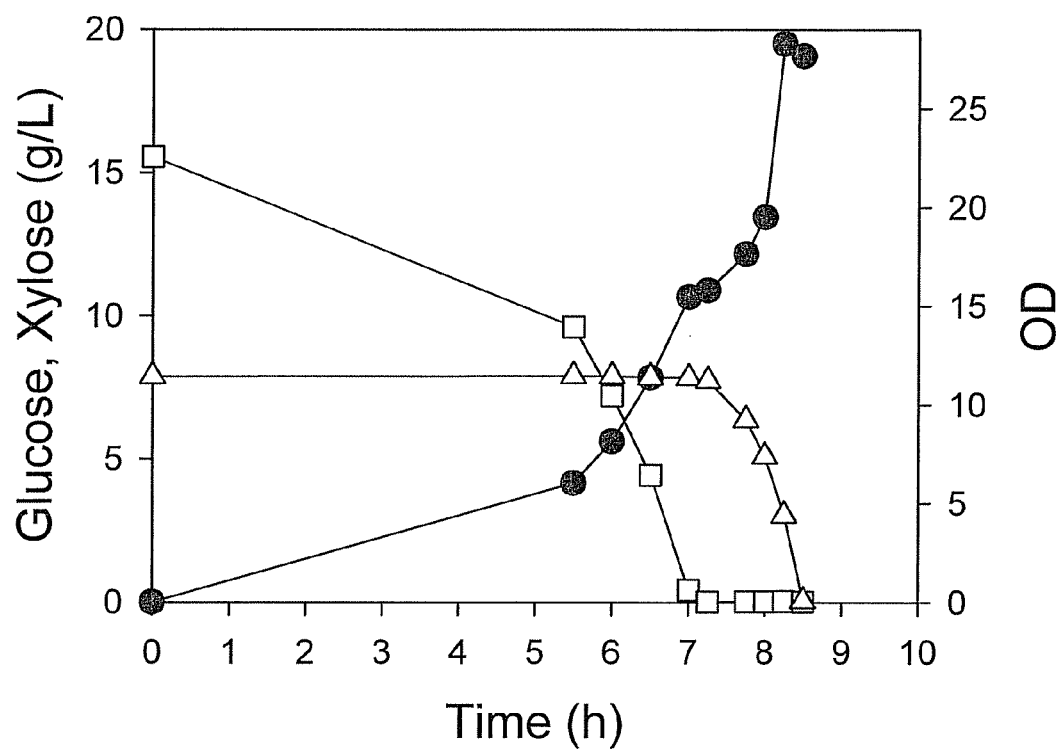
FIG. 2 shows batch aerobic fermentation of *Escherichia coli* MG1655 on a mixture of glucose (▽) and xylose (Δ). The OD (●) was measured over the course of fermentations.

In a first (control) experiment, a defined medium containing both 8 g/L xylose and 15 g/L glucose was inoculated with a single wild-type strain, MG1655, and grown aerobically (FIG. 2). The glucose/xylose mixture was chosen to reflect the concentrations of glucose and xylose that are found in typical lignocellulosic hydrolysates. As expected, we observed diauxic growth as reported by many other studies when a single strain is inoculated into a medium containing two or more carbon sources. The important observations were that glucose and xylose were consumed sequentially, and that the complete consumption of this mixture required about 8.5 hours.

Figure 3:
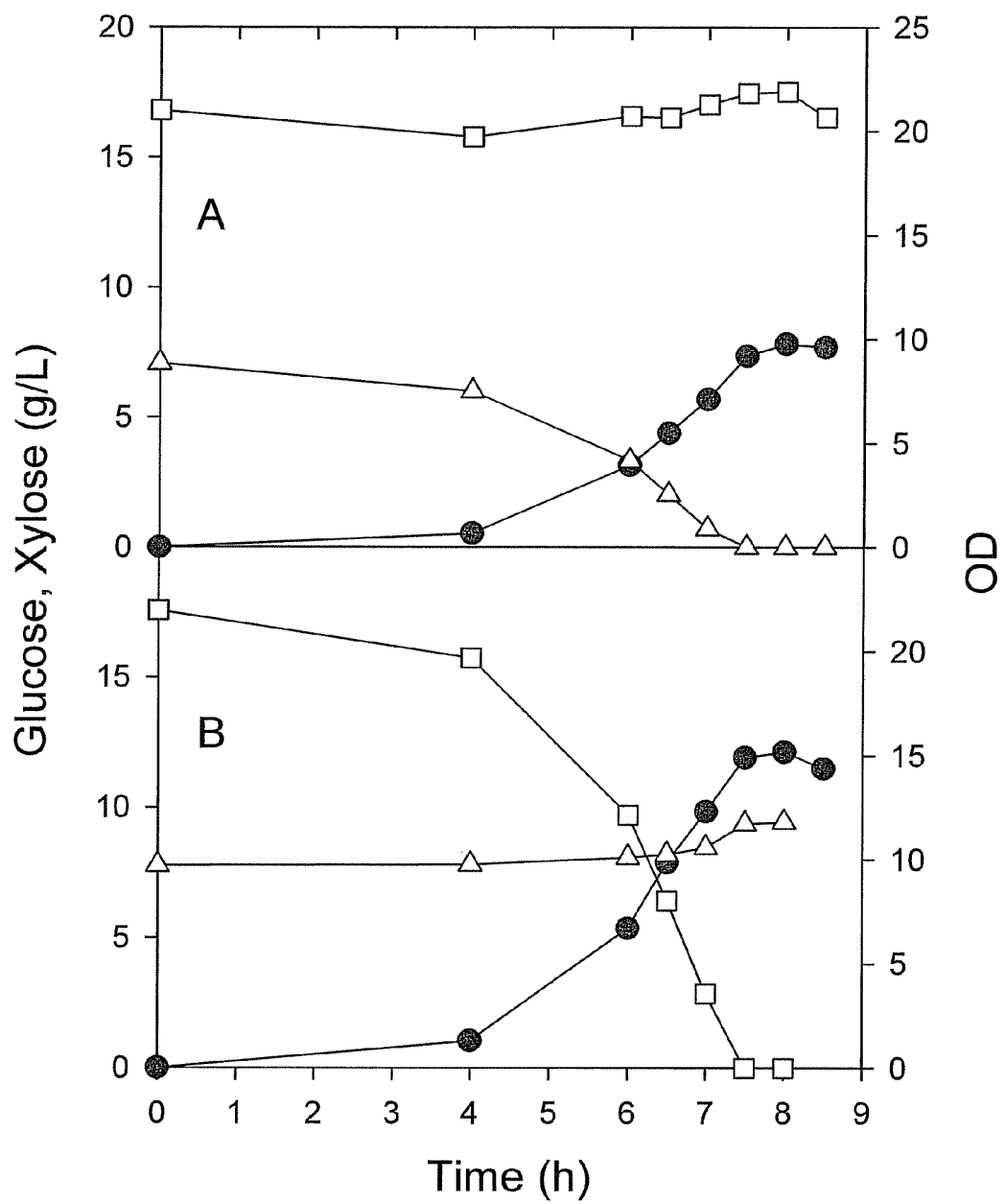
FIG. 3 shows batch aerobic fermentation of single *Escherichia coli* strains on a mixture of glucose (□) and xylose (Δ). The OD (●) was measured over the course of fermentations inoculated with A) ZSC113 only and B) ALS1008 only.

In a second set of aerobic experiments, the same defined medium containing two carbon sources was inoculated with one or the other of the two strains, ZSC113 or ALS1008. In the fermenter inoculated with only ZSC113 (FIG. 3a), 8 g/L xylose was completely consumed in 7 h and the OD reached 10, In this case, the concentration of glucose remained unchanged. In the fermenter containing only ALS1008 (FIG. 3b), we observed the complete consumption of 15 g/L glucose in 7.5 h with the OD reaching 15, while the concentration of xylose remained unchanged. As expected the two strains each consumed only one of the sugars, leaving the other carbohydrate unconsumed.

Figure 4:
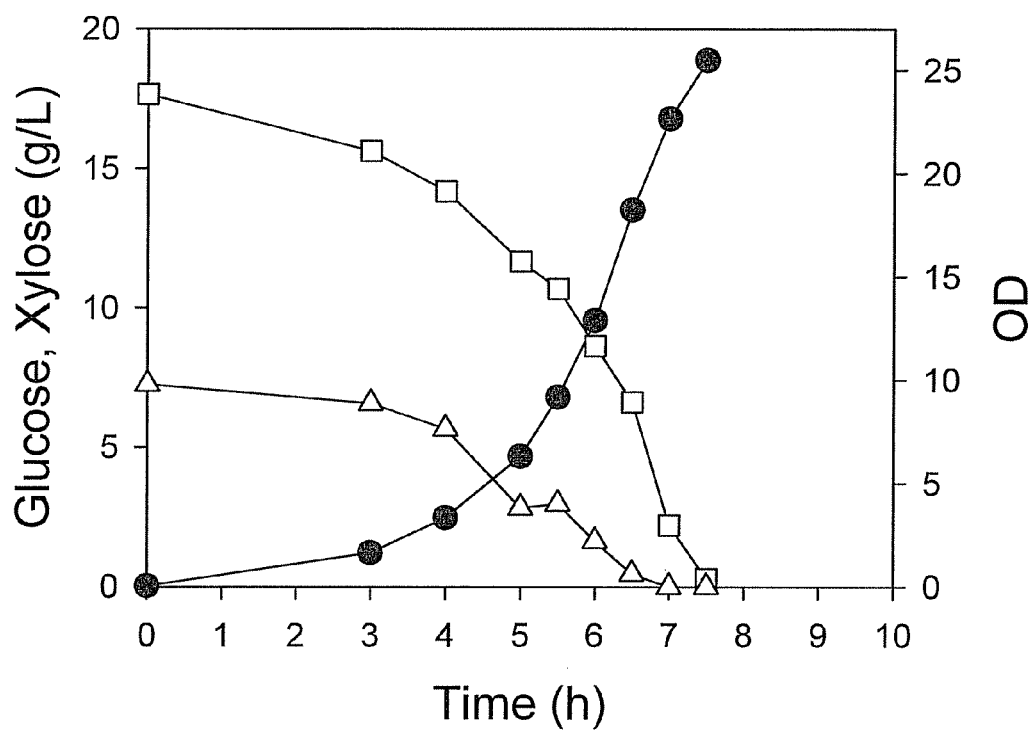
FIG. 4 shows batch aerobic co-fermentation of *Escherichia coli* strains ZSC113 and ALS1008 on a mixture of glucose (□) and xylose (Δ). The OD (●) was measured over the course of the fermentation.

In a third aerobic batch experiment, we inoculated both ZSC113 and ALS1008 into a single fermenter containing 8 g/L xylose and 15 g/L glucose. For this co-culture fermentation, glucose was consumed in 7.5 h, and xylose was simultaneously consumed in 7.0 h (FIG. 4). Moreover, the final OD of this mixed culture was about 25, identical to the sum of the ODs achieved in the fermentations in which one or the other carbohydrate was used. Thus, each strain appears to grow and consume its substrate independently. The combined process (i.e., consuming both sugars simultaneously) occurred at the same rate as the two individual processes so that each consumption rate was unaffected by the presence of the other carbohydrate. Compared to the wild-type (single organism) process, this process required about 15% less time to consume the same carbohydrate mixture aerobically, and moreover each substrate was consumed independently. The single-organism process (FIG. 2) was completely different than the dual-organism process (FIG. 4) in which both carbon sources were consumed simultaneously. No products were observed in these batch fermentations.

Aerobic Fed-Batch Utilization of Xylose/Glucose Mixtures

When a microorganism grows in a substrate-limited fashion (for example, in a fed-batch process), the growth rate is controlled by the rate that the limiting substrate is supplied. Moreover, the concentration of that substrate remains at zero. In a bioprocess with two substrate-selective organisms which are both under carbon-limiting conditions, each organism should independently be controlled by and adapt to the quantity of the carbon source present that it can consume. We wished to test this hypothesis using a fed-batch process in which the two-carbohydrate feed increased exponentially at a nominal rate of $0.1\ h^{-1}$, far below the maximum growth rate of either strain. Moreover, in addition to the flowrate exponentially increasing to maintain a fixed specific growth rate, the composition of the feed changed in discrete shifts in order to simulate a variable concentration that might be encountered in a real process. Specifically, for the first 20 h we maintained feed concentrations at 20 g xylose/L and 30 g glucose/L (20:30). At 20 h, this feed was replaced by feed concentrations of 30:30, at 30 h to 30:60, and then finally to 20:60 at 40 h. At 20 h, 30 h, 40 h and 50 h we determined the fraction of the population which was the glucose-consuming strain ALS1008 (and thus by difference the fraction which was the xylose-consuming strain ZSC113).

Figure 5:
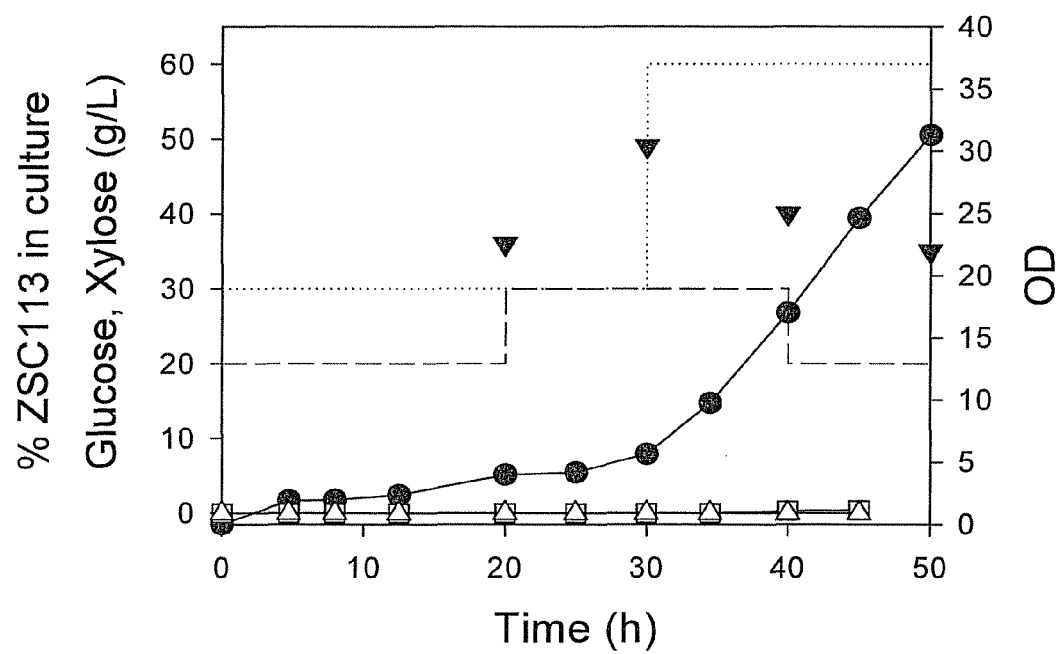
FIG. 5 shows fed-batch aerobic co-fermentation of *Escherichia coli* strains ZSC113 and ALS1008 using a feed containing a varying mixture of glucose (dotted lines) and xylose (dashed lines). The OD (●), the concentrations of glucose (□) and xylose (Δ), and the fraction of the total cell population which is ZSC113 (▼) were measured over the course of the fermentation.

During the entire fed-batch process, the xylose and glucose concentrations in the fermenter remained at zero (FIG. 5), demonstrating that each substrate individually limited the process. Moreover, the distribution of the microbial population responded in unison with the shift in substrate concentrations. At 20 h, after the process had acclimated to a 20:30 xylose:glucose composition (g/L), the population was 35% ZSC113 (i.e., the xylose-consuming strain). Ten hours after the feed composition shifted to 30:30, the population was 50% ZSC113. Similarly, ten hours after the feed composition shifted to 30:60, the population returned to 42% ZSC113, and then ten hours after the feed had become 20:60, the population decreased to 32% ZSC113. These results demonstrate that the process adjusts the distribution of strains to match the distribution of substrates.

Anaerobic Product Formation with Xylose/Glucose Mixtures

Wild-type *E. coli* is a mixed acid fermenter, and generates acetate, lactate, formate, ethanol and succinate under anaerobic conditions, with the yield of each depending on the strain and carbon source (Clark, 1989, *FEMS Microbiol. Rev.* 63:223). The strains used for this study of substrate-selective uptake did not generate an elevated concentration of any product during the aerobic studies (beyond the expectation for wild-type strains). ZSC113 and ALS1008 do not have any additional mutations which would cause the product distribution to be different from the wild-type parent MG1655. We thus wanted to examine how ZSC113 and ALS1008 behaved under anaerobic conditions in which products would accumulate. Three experiments were conducted under anaerobic conditions, analogous to those conducted under aerobic conditions previously.

Figure 6:
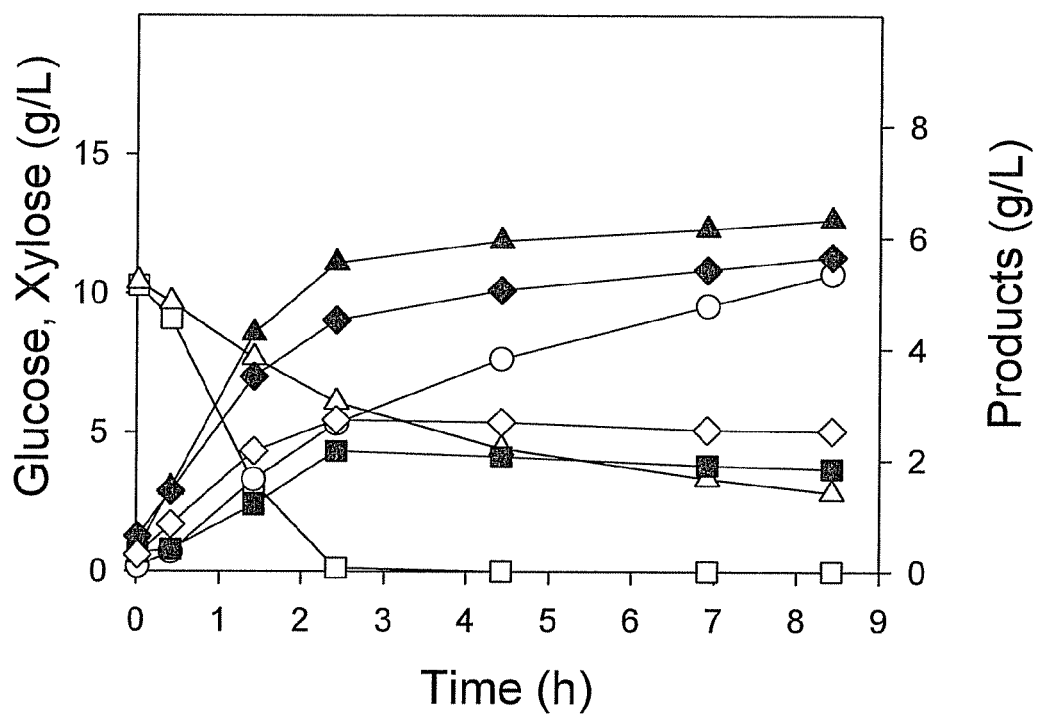
FIG. 6 shows batch anaerobic fermentation of *Escherichia coli* MG1655 on a mixture of glucose (□) and xylose (Δ). After 7 h (h, hours) of aerobic growth, additional xylose and glucose were added and anaerobic conditions commenced. The concentrations of formate (▲), lactate (■), succinate (○), acetate (♦) and ethanol (◇) were measured over the course of the anaerobic phase.

In a first experiment, wild-type MG1655 was grown under aerobic conditions as before to consume 15 g/L glucose and 8 g/L xylose. When both substrates were nearly consumed (after about 8.5 h as shown in FIG. 2), we added enough glucose and xylose into the fermenter approximately to return both concentrations to their initial levels. Anaerobic conditions were initiated under an atmosphere of 100% $CO_2$, and the products were measured during the anaerobic growth phase (FIG. 6). In this culture of a single strain (having an OD of 21) 10 g/L of glucose was consumed in about 2.5 h (4 g/Lh), equivalent to a specific glucose consumption rate of 630 mg/gh. Initially xylose was consumed at a rate of 310 mg/gh (2 g/Lh). However, after 4 h of anaerobic conditions, the xylose consumption rate decreased to less than 150 mg/gh (1 g/Lh), and continued to slow. Nearly 4 g xylose/L remained after 9 h of anaerobic conditions. It must be noted that the organism consumed glucose then xylose in the aerobic phase preceding these anaerobic conditions (as shown in FIG. 2), and therefore at the time of the switch to anaerobic conditions the xylose-consuming pathways were fully induced. One explanation for the substantial decrease in xylose consumption rate is the sensitivity of xylose-degradation to the presence of acetate as previously reported for yeast (Helle et al., 2003, *Enzyme Microbial Technol.* 33(6):786; van Zyl et al., 1991, *Enzyme Micro. Technol.* 13:82). This explanation is supported by the observation that xylose consumption continued to slow even after glucose was depleted under anaerobic conditions.

In a second experiment, the two substrate-selective strains ALS1008 and ZSC113 were grown individually on the mixed substrate medium, the one depleted substrate added back, and then anaerobic conditions commenced. For the case of the xylose-consuming strain ZSC113, xylose was consumed at a constant rate of 1.4 g/Lh during the anaerobic phase and glucose was not consumed (FIG. 7a). This single organism was present only at an OD of 9.5, so that on a specific basis the xylose consumption rate was 500 mg/gh, greater than the highest rate observed in the xylose portion of the fermentation using the wild-type MG1655. For the experiment in which the glucose-consuming strain ALS1008 was inoculated into the mixed substrate medium, glucose was exclusively consumed during the anaerobic phase at a constant rate of 3 g/Lh, and xylose was not consumed (FIG. 7b). In this case, the specific glucose consumption rate was about 770 mg/gh, greater than the rate we observed for the wild-type MG1655 during the anaerobic phase (i.e., FIG. 6). These two separate fermentations demonstrate that the strains will each consume only one substrate under anaerobic conditions, and that they will consume this substrate slightly faster on a specific basis than the wild-type strain would under identical conditions.

Figure 8:
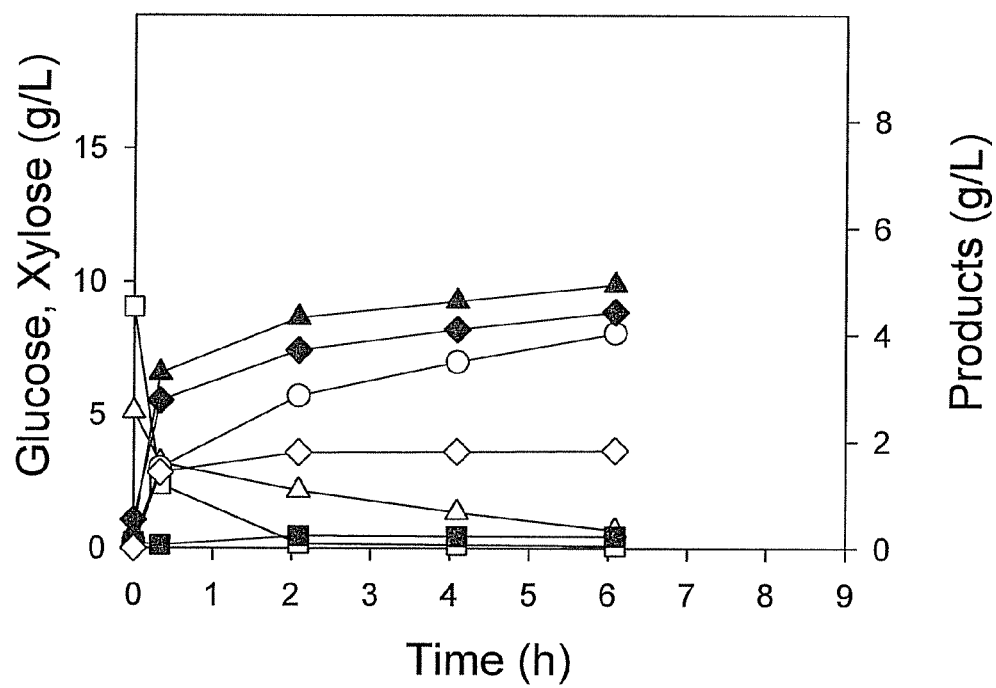
FIG. 8 shows batch anaerobic co-fermentation of *Escherichia coli* strains ZSC113 and ALS1008 on a mixture of glucose (□) and xylose (Δ). After 7 h of aerobic growth, xylose and glucose were added and anaerobic conditions commenced. The concentrations of formate (▲), lactate (■), succinate (○), acetate (♦) and ethanol (◇) were measured over the course of the anaerobic phase.

In a third experiment we first simultaneously grew both strains in the mixed substrate medium under aerobic conditions. At the end of the 7.0 h aerobic growth phase, we added enough of both carbohydrates to return them to their initial concentrations, and anaerobic conditions were initiated. In this process, both xylose and glucose were quickly consumed (FIG. 8). Although we did not measure the proportion of the two strains, from previous aerobic results using one substrate (i.e., FIG. 3), we estimate that the OD of ZSC113 was about 13 and the OD of ALS1008 was about 9. Over the first two hours of the anaerobic phase, the xylose consumption rate was therefore about 475 mg/gh, while the glucose consumption rate was about 1300 mg/gh. The key point in these results is that the two-strain process is much faster than an otherwise identical single-strain process.

The products formed from the two-sugar fermentation were the same as those generated during either one of the single-sugar fermentations, although the distribution of products changed slightly. For example, the succinate yield from xylose using ZSC113 was 0.48 mol/mol, while the succinate yield from glucose using ALS1008 was 0.30 mol/mol. From the sugar mixture, the observed succinate yield by two organisms was 0.41 mol/mol sugar consumed, a value between the yields of the individual strains on the two substrates. For all three cases, formate was generated with the highest yield (1.24 mol/mol glucose, 1.58 mol/mol xylose, and 1.46 mol/mol sugar mixture), and lactate was generated the least.

One limitation of this study was that high concentrations of acid products are known to inhibit growth and substrate consumption rates. This phenomenon would tend to affect the mixed culture more than either single-sugar culture, since for the former case both sugars would quickly be converted into more mixed acid products. This substrate-selective approach may perform significantly better for strains specifically designed to accumulate a single product such as ethanol which does not cause acid inhibition.

Discussion

The process described in this study offers a new approach for the simultaneous conversion of sugar mixtures into microbial products such as ethanol. The key characteristic of this approach is the use of multiple strains which are each selective in their consumption of a carbon source. Excluding substrate consumption in a strain by gene deletions represents an innovative shift from the long-studied approach of constructing a "do-it-all" organism for the conversion of multiple substrates into a desired product.

There are two significant advantages that the process has for the simultaneous conversion of sugar mixtures, as exemplified by xylose and glucose. Most importantly, as demonstrated by the fed-batch process (FIG. 5), the system adapts to fluctuations in the feed stream, i.e. cultures actually grow in concert with the feed composition. Since they are each specialists, the strains can not adversely compete with each other for the consumption of the substrates. Using a fed-batch process prevents sugar accumulation, and permits each strain to convert its target sugar at high yield and productivity. Operational robustness is the hallmark of this process strategy, and it constitutes a major advance toward the utilization of lignocellulosic biomass. Second, although not part of this study, additional metabolic engineering strategies can focus on improving the individual production strains independently. For example, work can now be devoted to improving the glucose-selective strain for ethanol production with minimal concern for how these changes would impact the conversion of xylose. We do not need to compromise one objective for another.

Gene knockouts affecting only one carbohydrate consumption pathway appeared not to have deleteriously impacted the consumption of the other carbohydrate. Indeed, previous results have demonstrated improved xylose utilization in sugar mixtures by the ptsG knockout alone (Kimata et al., 1997, Proc Natl Acad Sci USA. 94:12914; Nichols et al., 2001, Appl Microbiol Biotechnol. 56:120). In this study, catabolite repression due to the presence of glucose was made irrelevant by the use of two strains, since one cannot utilize glucose at all.

The results demonstrate that a population of substrate-selective strains, in which each individual strain only consumes a single sugar, is better able to metabolize a sugar mixture than a single strain consuming multiple sugars. Other than the mutations involving substrate consumption, the strains used for this study did not contain additional mutations which would cause them to generate a product preferentially. The next step would be to use this approach with microbial strains specifically modified to accumulate a desired product such as ethanol. This approach could potentially be extended to construct additional strains capable of the exclusive consumption of other sugars (e.g., arabinose) or inhibitors such as acetic acid and furfurals that are frequently found in lignocellulosic hydrolysates.

Example 2

Consumption of Acetate by *Escherichia Coli*

*E. coli* readily consumes acetic acid as a sole carbon/energy source (El-Mansi et al., 2006, *Curr. Opin. Microbiol.* 9:173), but it generally will not consume acetate in the presence of other substrates from which the cells can derive more energy. Of course, the presence of acetate diminishes the rates at which other substrates are consumed. However, *E. coli* can be forced to grow on acetate and prevented from consuming glucose or xylose (for example) by knocking out the genes which encode for glucose and xylose consumption. We refer to such a strain as "acetate-selective" because of the three substrates, acetate is its exclusive carbon nutrient. When exposed to a hydrolysate containing acetate, xylose and glucose, only the acetate will be consumed. This approach is merely an extension of the substrate-selective concept introduced above for xylose and glucose mixtures.

We tested whether acetate could be selectively removed from a mixture of xylose, glucose and acetate. We used *E. coli* MG1655 to generate ALS1060. MG1655 is a common wild-type strain (Jensen, 1993, *J. Bacteria* 175:3401), and we verified that it grows aerobically with acetate as the sole carbon source at a growth rate of approximately $0.24\ h^{-1}$. ALS1060 has four knockouts of genes coding for proteins involved in xylose and glucose utilization (these genes were described above): ptsG, manZ, glk, and xylA. These four mutations should prevent the consumption of either xylose or glucose by ALS1060, but have no known effect on acetate metabolism.

Figure 9:
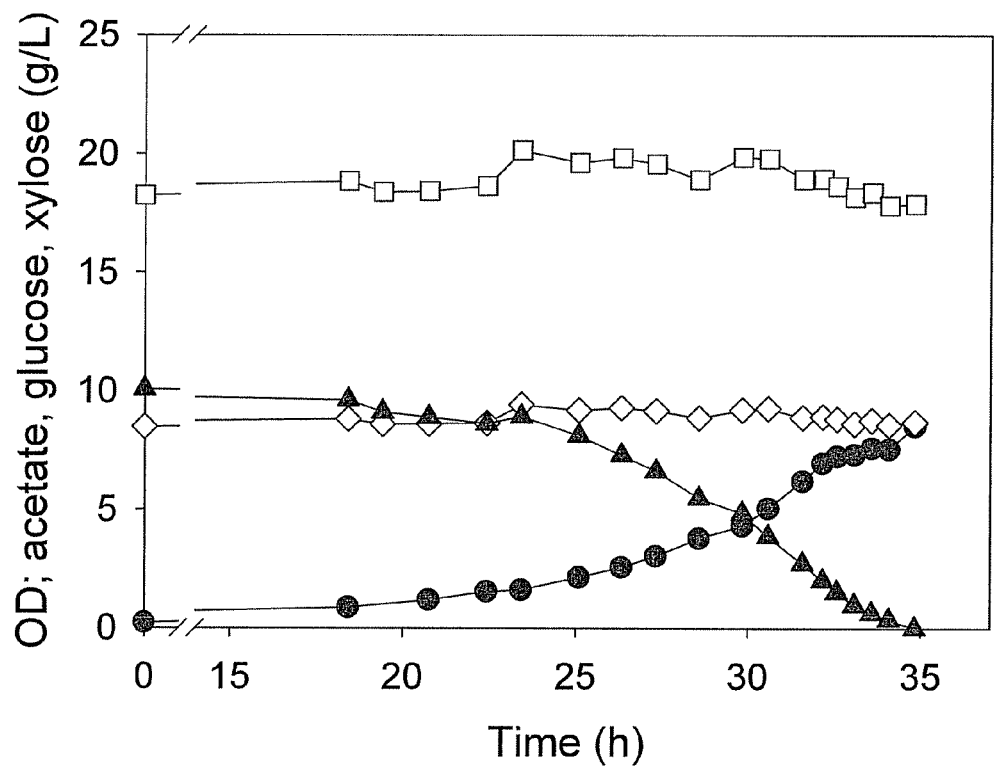
FIG. 9 shows batch aerobic fermentation of *Escherichia coli* ALS1060 (knockouts in ptsG manZ glk xylA) on a mixture of glucose (□), xylose (Δ) and acetate (▲). The OD (●) was measured over the course of the fermentation time.

We grew ALS1060 in a batch process using a medium containing an extremely high proportion of acetate: 10 g/L acetate, 10 g/L xylose and 20 g/L glucose. In this case, ALS1060 consumed 10 g/L acetate at a growth rate of $0.16\ h^{-1}$, but left xylose and glucose unconsumed even after 40 hours (FIG. 9). The significant lag phase observed in this experiment can be attributed to using the poor MG1655 strain and the sudden exposure to 10 g/L acetate. Acetate consumption depends on the cellular balance between the glyoxylate shunt and isocitrate dehydrogenase (Holms, 1986, *Curr Top Cell Regul* 28:69), and different *E. coli* strains would be expected to behave quite differently. Our selection of MG1655 was merely to provide evidence that the concept would work; this strain turned out not to be a good acetate-grower. We have recently found *E. coli* strains which consume acetate at a growth rate over $0.70\ h^{-1}$ with no lag, and will use these strains to develop the acetate-selective strain as described in the experimental approach.

In the preliminary experiments reported in Examples I and II we have been able to 1) remove acetate selectively from a mixture of xylose, glucose and acetate and 2) consume xylose and glucose simultaneously in a mixture of these two sugars. These steps can be linked together in a two-stage process to generate a product like ethanol, as conceptualized in FIG. 1 for an acetate/xylose/glucose mixture. After removal of acetate in Stage 1, the remaining mixture is subsequently fermented in a second process stage (Stage 2) to the desired product. Because knock-out strains are very stable, the strategy can readily be extended to any number of substrates. For example, an arabinose-selective strain will be unable to consume xylose and glucose, etc.

Example 3

Two Stage Fermentation

Rather than try to develop a single organism to accomplish all the process design goals required for lignocellulosic conversion, our novel approach uses multiple strains to do tasks efficiently and independently. Note that no competition exists in the envisioned co-culture (in Stage 2, FIG. 1). Competition involves multiple species competing for the same substrate. In this case, the strains each seek only their specific substrate and, being otherwise the same, do not interfere with each other. Thus, potential shortcoming from competition in a "mixed-culture" bioprocess is avoided.

There are several significant advantages that the envisioned continuous/fed-batch process has for the elimination of acetic acid and the simultaneous conversion of sugar mixtures, as exemplified by xylose and glucose. First, because the acetate-selective strain cannot grow in the absence of acetic acid, these cells will ultimately lyse in the second stage. By lysing, the cellular nutrients derived from acetate utilization are available to support growth of cells present in Stage 2. So, the inhibitor actually enhances product formation by enriching the hydrolysate with growth nutrients. It does not matter if the cells consume additional nutrients such as nitrogen, phosphorus, sulfur. These nutrients are conserved and become readily available to the organisms in the second stage. The goal of the first stage is only to consume acetate (quickly) and not consume any sugars.

Secondly, metabolic engineering strategies can focus on improving the individual production strains independently. For example, additional work can be devoted to improving the glucose-selective strain for ethanol production without concern for the impact of these changes on the conversion of xylose or on acetate tolerance/degradation. We do not need to compromise one objective for another.

Finally, the system adapts to fluctuations in the feed stream; that is, cultures actually grow in concert with the feed composition. For example, the system would respond to an increase in acetate concentration merely by increasing the cell density in Stage 1. Regardless of the perturbation of acetate in the feed (within a large range, as long as the cells remain carbon limited), this inhibitor will be completely removed in Stage 1. Similarly, as we have already observed, the system responds to an increase in the feed xylose concentration by increasing the cell density of the xylose-selective strain in Stage 2 (with no change in the cell density of any other strain). Using a fed-batch process would prevent sugar accumulation, and each strain would convert its target sugar at high yield and productivity. Operational robustness is the hallmark of this process strategy, and it constitutes a major advance toward the utilization of lignocellulosic biomass.

Example 4

Concurrent Use of Sugars by *Escherichia Coli*

In Example 1 we demonstrated that the concept of substrate-selective uptake works. Using *E. coli* we demonstrated that a xylose-selective strain will consume only xylose and a glucose-selective strain consumes only glucose in a mixture of these two sugars and without impacting each other. Moreover, in Example 2 we demonstrated that acetate can be selectively removed from a mixture of acetate, glucose and xylose.

The strains used in these studies were not isogenic, not derived from optimally-growing strains and did not generate any product such as ethanol. We will construct a series of substrate-selective strains and demonstrate the two-step process shown in FIG. 1 on simulated and actual hydrolysates. Strains are constructed based on gene deletion and/or heterologous gene transformation, then their behavior in controlled bioreactors is examined. After initial examination in bioreactors, additional molecular biology may be necessary to further improve or optimize the strain.

The following examples describe various aspects of the invention:

Example 4. Concurrent use of sugars by *Escherichia coli*
Example 5. Introduction of ethanol pathways into the strains
Example 6. Fermentation of simulated sugar mixture
Example 7. Consumption of acetate by *Escherichia coli* without sugar degradation
Example 8. Simulated and real hydrolysates
Example 9. Concurrent use of xylose and glucose by Lactic Acid Bacteria Like many sugars, glucose must first be phosphorylated before it can be further metabolized by *E. coli*. The principal route to phosphorylate glucose is by the phosphotransferase system (PTS). Because the PTS phosphorylates several sugars, some of the enzymes involved have broad specificities and can phosphorylate more than one sugar (Postma et al., 1993, *Microbiol Rev.* 57:543). Glucose can be phosphorylated by two different enzymes of the PTS, glucosephosphotransferase and mannosephosphotransferase encoded respectively by the ptsG and manZ genes (originally designated as gpt and mpt). Furthermore, glucose can be phosphorylated by the enzyme glucokinase which is encoded by the glk gene (Curtis and Epstein, 1975, *J. Bacteria* 122(3):1189). Strains that are unable to use glucose as a carbon source can be constructed by knocking out the genes encoding for glucose-phosphotransferase (ptsG), mannosephosphotransferase (manZ) and glucokinase (glk).

Xylose is transported into *E. coli* by the xylose transport system and once internalized must be isomerized to xylulose by xylose isomerase and phosphorylated to xylulose-phosphate by xylose kinase before it can be metabolized (David and Weismeyer, 1970, *Biochim. Biophys. Acta.* 201:497). Strains that are unable to utilize xylose as a carbon source can be constructed by knocking out the gene encoding for xylose isomerase (xylA).

Arabinose is another sugar found in biomass hydrolysates, accounting for about 5% of the total sugar. The consumption of arabinose into *E. coli* is essentially analogous to the xylose uptake process. Arabinose consumption can be eliminated by knocking out the araA gene.

The hexose galactose is a component in lignocellulosic hydrolysate, but is commonly found at concentrations of 1% or less (Lee, 1997, *Appl. Microbiol. Biotechnol.* 65:56). Galactose uptake is mediated by galactokinase encoded by the galK gene, and galactose uptake is eliminated in a galK mutant. Because the composition of galactose in hydrolysate is so low, eliminating galactose uptake may be unnecessary.

The presence of the hexose mannose in lignocellulosic hydrolysate varies widely between 0-12% depending on the biomass (Lee, 1997, *Appl. Microbiol. Biotechnol.* 65:56). Mannose is phosphorylated exclusively by the mannose-specific components of the PTS (e.g., mannosephosphotransferase) encoded by manX; manY and manZ. Preventing glucose uptake by the triple mutations as described above (manZ) also prevents mannose consumption. Similarly, knocking out xylA and araA (and galK) has no impact on mannose consumption. Using the strategy outlined so far, we cannot construct a strain which consumes mannose but not glucose.

In order to consume all the sugars present in lignocellulosic hydrolysates simultaneously, strains are constructed which are expected to consume each one of these sugars alone. Thus, the following strains will be constructed:

a) glucose-selective strain: mutations in araA galK xylA manZ
b) xylose-selective strain: mutations in ptsG manZ glk araA galK
c) arabinose-selective strain: mutations in ptsG manZ glk xylA galK
d) galactose-selective strain: mutations in ptsG manZ glk araA xylA
e) mannose-selective strain: mutations in araA galK xylA or araA galK xylA ptsG glk (these strains will also consume glucose)

Our preliminary experiments (Examples I and II) were conducted in *E. coli* K12 or its non-isogenic derivatives, and included xylose and glucose, not the two other uniquely consumed sugars galactose and arabinose. The construction of a completely substrate-selective strain requires knocking out all other uptake systems. So, for example, to construct a xylose-selective strain, we knock out the glk, ptsG, manZ, galK and araA genes in the *E. coli* B strain. The B strain has been chosen for this project because it is a widely used prototrophic derivative of wild-type *E. coli* that is well characterized and grows rapidly in both defined and complex media. Furthermore, our experience is that this strain grows very well on a variety of carbon sources (e.g., xylose, arabinose, etc.). Other research groups have also favored derivatives of the B strain (Ingram et al., 1999, *Biotechnol. Frog* 15:855; Tao et al., 2001, *J. Bacteriol.* 183(10):2979). The *E. coli* gene knockouts are constructed using the Keio collection of single-gene knockout mutants (Baba et al., 2006, *Mol. Syst. Biol.* 2:2006.0008). The lambda Red recombination system (Yu et al., 2000, *Proc Natl Acad Sci USA* 97:5978; Datsenko and Wanner, 2000, *Proc Natl Acad Sci USA.* 97:6640) may also be employed to construct the required gene knockouts. For, control purposes substrate-selective strains that we construct can be compared to similar publicly available strains (such as CGSC5457 from the *E. coli* Genetic Stock Center that contains mutations in the gik, ptsG, and manZ genes and thus also can not consume glucose). The 4 substrate-selective B strains (one for each of glucose, xylose, arabinose and galactose) are expected to be useful platforms for other researchers to develop processes for the formation of various products from the five sugars (including mannose).

Additionally, using the same approach we will construct 4 substrate-selective using the ethanologenic *E. coli* strain "KO11." The result is expected to be eight substrate-selective strains (four each derived from B and KO11).

Example 5

Introduction of Ethanol Production Pathways into Sugar-Selective *E. Coli* Cells Decades of research have led to great improvements in strains of *E. coli* that accumulate ethanol, and the approach described herein can be adapted to current or future *E. coli* ethanologenic strains. The approach can be adapted readily to strains of *E. coli* which generate any other compound.

The sugar-selective KO11 strain of Example 4 is expected to be ethanologenic, since KO11 is ethanologenic. To make the sugar-selective B strain of Example 4 ethanologenic, ethanol pathways will be introduced into those strains. The four sugar-selective B strains will be transformed with pLOI308 (Ingram et al., 1987, *Appl. Environ. Microbiol.* 53:2420; Ingram and Conway, 1988, *Appl. Environ. Microbiol.* 54:397), one of the better characterized plasmids that elevates ethanol formation in *E. coli*. This plasmid uses the *Zymomonas mobilis* pyruvate decarboxylase and alcohol dehydrogenase genes. In *Zymomonas mobilis*, pyruvate is converted by pyruvate decarboxylase to acetaldehyde, which is subsequently converted to ethanol by alcohol dehydrogenase. Together these enzymes comprise nearly 10% of the soluble protein of wild-type *Z. mobilis* cells grown with glucose as the substrate (Doelle et al., 1993, *Crit. Rev. Biotechnol.* 13:57), enabling this organism to maintain a high conversion efficiency to ethanol.

The result is expected to be two sets of ethanologenic, sugar-selective strains of *E. coli* (four each derived from B and KO11; 8 total).

Example 6

Fermentation of Simulated Sugar Mixtures

This example relates to the characterization of processes to metabolize sugar mixtures, ultimately in the presence of acetic acid (as described below in a subsequent section). Initial studies will be performed on synthetic mixtures of 2-5 sugars (selected from the list of mannose, galactose, glucose, xylose and arabinose), while subsequent studies will be conducted on real hydrolysates supplemented with additional nutrients as required (e.g., nitrogen and phosphate sources). These studies will use the 8 strains generated from Example 5, with 4 strains present in a co-culture at the same time when all 5 sugars are present.

We will first establish the operating ranges for the processes through a series of chemostat experiments. While not generally used in industry, chemostat experiments provide an extremely useful way of determining the parameters necessary to design a relevant process (for example, a fed-batch process which is commonly used.) Like all fermentation experiments, these studies will involve highly-instrumented bioreactors in which feed-rate, temperature, pH, nutrient levels, oxygenation, etc. can be controlled. By studying a range of controlled growth rates, we will determine for each strain the biomass yields, specific rates of consumption/production of dissolved and gaseous compounds, and the maintenance energy requirements resulting from the various genetic perturbations. Like any cells growing on different carbon-sources, these strains will have differing maximum growth rates. Note that in a chemostat the microbial growth rate is determined by the nutrient feed rate (dilution rate), but the biomass concentration is determined by the limiting nutrient concentration. These maximum growth rates will help establish the maximum feed-rate of an envisioned fed-batch process. Operating a biological process at the maximum growth rate does not in general result in the maximum practical product formation rate for a variety of reasons such as oxygen requirement (for an aerobic process), heat duty, reduced biomass yield, genetic regulation of cells, etc. We will study the strains individually on single-substrate media, then single strains on dual-substrate media, then multiple strains on dual-substrate media. Drug resistances introduced into some strains will serve as selective markers to permit us to quantify the fraction of each strain comprising the total population.

In addition to the principal carbohydrates, major and minor fermentation products including ethanol, acetate, lactate, formate, succinate will be analyzed. We anticipate that significant lactate and formate will be generated for the B-derived ethanologenic strains, and in this case they may be further modified by deleting the enzymes responsible for these products: deleting the ldh gene which encodes lactate dehydrogenase will eliminate lactate from being produced while deleting the pfl gene which encodes pyruvate formate lyase will eliminate formate. We have used this strategy to increase the fermentation yields of several products in E. coli (Tomar et al., 2003, Appl. Microbiol. Biotechnol. 62:76; Lee et al., 2004, Appl. Microbiol. Biotechnol. 65:56; Smith et al., 2006, Appl. Microbiol. Biotechnol. 28:1695; Zhu et al., 2007, Appl. Environ. Microbiol. 73:456).

The chemostat experiments will provide us with parameters to enable the study and implementation of a fed-batch process. We will feed in the mixed-sugar stream in a carbon-limited fashion (that is, each one of the four strains will be carbon limited for their sugar substrate). During an initial process "phase" cells will grow aerobically, while in a subsequent production phase, reduced oxygen availability will direct most of the carbon to the product ethanol. As long as the carbon-limited feed rate is lower than the capacity for carbohydrate uptake, the cells should respond to changes in the concentration of either substrate merely by increasing the biomass as we have observed in preliminary studies. We will confirm this expectation by introducing a temporally varying stream of mixed sugar into the fermenter, and monitoring how the composition of the culture changes (including the population of each strain). The result of this portion of the research will be a complete and quantitative description of the fermentation of sugar mixtures to ethanol by substrate-selective strains.

Example 7

Consumption of Acetate by Escherichia coli without Sugar Degradation

A strain of E. coli is constructed which consumes acetate but not any of the five principal sugars in biomass hydrolysate as described in Example 2. This process will require knockouts of all the sugar uptake systems. We have already demonstrated in Example 1 that this approach works for xylose and glucose, the two principal sugars in most lignocellulosic hydrolysates.

The strain(s) used to make these knockouts are those that exhibit high growth rate and high biomass yield on acetate. Tolerance of the organism to high acetate concentration is not important (within a range) because we envision the process operating in fed-batch or continuous mode under carbon (i.e., acetate) limitation. Under these circumstances the concentration of acetate in the fermenter will be maintained at zero and cell "tolerance" to the acetate will not be relevant. However, the rate at which acetate is consumed will directly affect the productivity of the entire process. Therefore, the cells should ideally be able to grow at a high growth rate which will enable the process to run at a high (dilution) rate without any negative consequences.

Although several research groups have studied growth of E. coli on acetate and completed detailed flux analyses, there has not been a comprehensive comparison of the growth rate of E. coli strains on acetate as the sole carbon source. We will examine 8-10 diverse wild-type and common strains of E. coli (e.g., MG1655, DH5α, MC4100, BL21, JM109, etc.) and grow them as accelerostats (Paalme et al., 1997, Ant. van Leeuwen. 71:217). B strains are preferred because these strains appear to have an elevated expression of enzymes in the glyoxylate shunt (van de Walle and Shiloach, 1998, Biotechnol. Bioeng. 57:71; Phue and Shiloach, 1998, J. Biotechnol. 109:21), which is an important pathway for acetate metabolism. A preliminary study in shake flasks has indicated some strains do indeed grow with a very high rate on acetate (0.70 h$^{-1}$, about 3 times faster than on MG1655 which was selected for preliminary studies). In this study we determined the growth rate of several publicly available bacterial strains. The table below shows observed growth rates.

| Strain | Specific Growth Rate (h-1) | biomass yield (g/g) |
|---|---|---|
| AG1 | 0.676 | 0.303 |
| MC1061 | 0.520 | 0.315 |
| MC4100 | 0.371 | 0.279 |
| 9637 | 0.368 | 0.327 |
| JM101 | 0.322 | 0.285 |
| BL21 | 0.305 | 0.232 |
| MG1655 | 0.253 | 0.309 |
| W3110 | 0.245 | 0.281 |

This approach can be readily used establish biomass yield and maximum growth rate. The two "best" strains, AG1 and MC1061, are selected to knockout the sugar-consuming abilities (described below). Note that the strain found to be the "best acetate consumer" will not necessarily be related to the strain ultimately found to be the "best sugar consumer/ethanol producer." A significant advantage of our process design is that these two strains can be selected independently.

In order to learn why certain strains grow more quickly on acetate, we will complete a genome-wide microarray study. For four of the strains (two "fast growers" and two "slow" growers), we will take samples from our accelerostat experiments (which occurs at a pseudo-steady state) at three different growth rates (approx. 0.1, 0.2, 0.3 h$^{-1}$). We will conduct microarrays comparing expression at these growth rates (i.e., 0.3 vs. 0.1 and 0.2 vs. 0.1) and at the highest growth rate between the strains (strain 2 vs. strain 1, strain 3 vs. strain 1, strain 4 vs. strain 1). With (independent) triplicate experiments, this will involve 15 microarrays. This approach is similar to our previous study at 6 steady-state growth rates to establish the regulatory importance of the arcAB regulatory network in acetate overflow metabolism (Vemuri et al., 2006, Appl. Environ. Microbiol. 72(5):3653).

Once suitable strains of E. coli are identified, they must be made acetate-selective, i.e., they will need deletions in genes involved in the uptake of glucose, mannose, galactose, xylose and arabinose. In the two strains selected for their "best" acetate metabolism, the six genes manZ, ptsG, glk, xylA, galK, araA will be knocked out as described in Example 4. None of these genes has any known relationship with acetate consumption, a process which is mediated by acetyl CoA synthase (acs), isocitrate lyase (aceA), malate synthase (aceB) and isocitrate dehydrogenase (icdA) (Holms, 1986, Curr Top Cell Regul 28:69).

Example 8

Use of Simulated and Real Hydrolysates

Two-stage fermentations of simulated mixed xylose, glucose, mannose, arabinose, galactose and acetate solutions as well as actual hydrolysates will be conducted using the constructed E. coli strains. A "simulated" solution is merely a synthetic (and reproducible) medium prepared with purified components in appropriate proportions to represent a real hydrolysate. In other words, we will prepare a defined medium containing these six compounds as potential carbon sources. Concentrations of these compounds in actual hydrolysates vary considerably (Barbosa et al., 1992, Appl. Environ. Microbiol. 58:1382; Johansson et al., 2001, Appl Environ Microbiol. 67:4249; Taherzadeh et al., 2001, Appl Biochem Biotechnol. 95:45; Brandberg et al., 2004, J. Biosci Bioeng. 98:122), and we will examine a range of concentrations: 20-40 g/L glucose, 5-20 g/L xylose, 1-5 g/L galactose/mannose/arabinose and 2-8 g/L acetic acid. Although we have the ability to generate biomass hydrolysates, we will primarily rely on real hydrolysates obtained from researchers at other Universities and Federal Labs. As necessary, the hydrolysate will be supplemented with other nutrients such as nitrogen, phosphorus and sulfur.

The initial studies will use simulated hydrolysates. The first stage in the process (the left bioreactor in FIG. 1) involves the removal of acetic acid by feeding an acetate-containing hydrolysate into the reactor so that the organisms grow continuously and the acetate-free stream with cells exits the vessel continuously. Using the growth rate data obtained previously, we will feed the acetate at a dilution rate below the maximum growth rate and scale the process accordingly. We will determine the ranges of acetate concentration in the hydrolysate that are acceptable, and the rates for which the process can be conducted. We will determine the long-term stability of the process. The acetate consumption rate determined from such data will be helpful in sizing a pilot/commercial process. When acetate is the limiting nutrient under aerobic conditions, we anticipate that the carbon in acetate will be converted either into cells or $CO_2$. We will nevertheless need to complete a detailed carbon balance to account for the utilization of carbon under various operating conditions. The formation of the potential metabolic products such as ethanol, lactate, formate, succinate, and fumarate in the detoxification step is not anticipated but will be determined in addition to the concentrations of the six substrates via chromatography (Eiteman and Chastain, 1997, Anal. Chim. Acta 338:69).

Additionally, we will demonstrate the robustness of the process by "ramping" the concentration of acetate in the feed and observing the response of the microbial system to changing acetate concentration. We anticipate that the cells will naturally adapt to changing concentrations of acetate in the feed stream by increasing the biomass concentration, as we have observed in preliminary studies for the two-substrate system. For simulated hydrolysate we anticipate that the stream exiting Stage 1 will contain exclusively 5 sugars (and biomass) as carbon sources.

Stage 2 will be fed the stream exiting Stage 1. It is advantageous to maintain Stage 1 as a continuous (or fed-batch) process to maintain a zero acetate concentration as a result of substrate limitation. The matching of this continuous process with Stage 2 will be a significant aspect of this part of the research project. Three different bioprocess modes will be examined for Stage 2, including: 1) batch, 2) linear fed-batch, and 3) exponential fed-batch. A batch process will be conducted by fermenting a discrete portion of the (continuous) effluent from Stage 1. Such a process will require storing some of the Stage 1 effluent in a tank. A linear fed-batch will be conducted by synchronizing the Stage 1 effluent rate with the feeding rate to Stage 2. In this case, because the biomass concentration in Stage 2 is small the feed initially into Stage 2 will exceed the rate of carbohydrate consumption, and the cells will grow at their maximum growth rate. Later after the biomass concentration increases, the maximum growth rate will exceed the carbohydrate feed rate and Stage 2 will become carbon limited. An exponential fed-batch, accomplished via a programmable pump, will involve holding a portion of the Stage 1 effluent initially and gradually increasing the rate of feeding to match a desired cell growth rate. We routinely perform exponential fed-batch processes (e.g., Smith et al., 2006, Appl. Microbiol. Biotechnol. 28:1695) as they are advantageous to control growth and product formation rates carefully. The focus of this portion of the research will be to study the kinetics of sugar consumption subsequent to acetate removal. Process stability, mode of operation, robustness to varying feed compositions and sensitivity to inoculation approaches will all be addressed in this portion of the project.

We will study ethanol production in this process, using a single organism process with E. coli KO11 (without additional substrate-selectivity) as an experimental control. Although a couple of different ethanol-production approaches are possible depending on the specific strain, we envision a two-step process for Stage 2 wherein the first step is an aerobic growth phase using the two strains and substrates. A second step involves a potential anaerobic production phase wherein all the carbon is directed to the product of interest, ethanol, and growth is low. Growth can be slowed by several means including limiting the feed in another nutrient such as nitrogen (i.e., ammonium ion).

We will also obtain lignocellulosic hydrolysates and determine the detoxification of that hydrolysate using the acetate-selective strain in the developed process. As noted, it is likely that the raw hydrolysate will require supplementation with additional nutrients in order to permit growth of the acetate-selective strain in Stage 1 and the growth of the 4 sugar-selective strains in Stage 2. Several commercial processes use nutrient supplementation which does not negatively impact the cost of production (ammonia, phosphate). We will readily be able to determine whether the hydrolysate is, for example, phosphate-limited rather than carbon-limited by determining the nutrient levels in the effluent stream. We anticipate that the feasible feed rates for both stages will be lower when lignocellulosic hydrolysate is used compared to simulated hydrolysate. The results from these studies will be critically compared with the results obtained using the simulated xylose, glucose and acetate solution.

Example 9

Concurrent Use of Xylose and Glucose by Lactic Acid Bacteria

So-called facultative homofermentative strains of Lactic Acid Bacteria are of great interest because they are able to consume either xylose or glucose (and other sugars), and many also have a high tolerance to low pH and temperatures exceeding 50° C. These qualities make these microorganisms particularly relevant for the production of lactic acid (currently manufactured commercially) and other products including ethanol. The substrate-selective approach of the invention can be advantageously utilized in this organism. Strains of *Lactobacillus* and *Lactococcus* which are able to consume selectively xylose and glucose will be constructed. Other researchers have explored ethanol production in *Lactobacillus* (Nichols et al., 2003, J. Indust. Microbiol. Biotechnol. 30:315). This study is expected to show that (1) inhibitor-removal and sugar-conversion steps are decoupled in the method of the invention, and (2) two different species can be used in the two separate stages without any disadvantages. Importantly, because of these advantages, researchers no longer have to pass over a strain for the production of a biochemical merely because it is intolerant of another chemical which could now be removed (using our approach) in a previous stage by another organism.

First, isogenic xylose-selective and glucose-selective strains of Lactic Acid Bacteria will be constructed. A Lactic Acid Bacteria strain that can consume both xylose and glucose is chosen as the starting strain for developing the isogenic xylose-selective and glucose-selective strains. Like *E. coli*, Lactic Acid Bacteria possess glucose-specific uptake pathways in addition to the general PTS which facilitates the import of a variety of sugars. The cytoplasmic phosphocarrier enzymes of the PTS have been identified in several Lactic Acid Bacteria species and are encoded by the ptsH and ptsI genes which reside in an operon, and as in *E. coli*, Lactic Acid Bacteria ptsHI deletion mutants are still able to metabolize glucose (Stentz et al., 1997, *Appl. Environ. Microbiol.* 63:2111; Luesink et al., 1999, *J. Bacteriol.* 181:764; Viana e al., 2000, *Mol. Microbiol.* 36:570). However, because the glucokinase homologue has not been identified in a Lactic Acid Bacteria species in which the ptsHI operon has also been characterized, we will start with a Lactic Acid Bacteria species in which ptsHI has been deleted in order to construct a xylose-selective Lactic Acid Bacteria strain.

*Lactobacillus casei*, *Lactobacillus sake*, and *Lactococcus lactis* are species of Lactic Acid Bacteria in which the ptsHI genes have been characterized and which also can utilize xylose as a sugar source (Zhang et al., 1995, *Appl. Biochem. Biotechnol.* 51/52:527; Erlandson et al., 2000, *Appl Environ Microbiol.* 66:3974). Similar to the *E. coli* studies in which we select a strain for acetate consumption (Example 7), we will first compare these three candidate Lactic Acid Bacteria to determine their growth rates in minimal xylose media to choose a preferred strain for these studies. ptsHI derivatives of each of these three strains are available (Stentz et al., 1997, *Appi. Environ. Microbiol.* 63:2111; Luesink et al., 1999, *J. Bacteriol.* 181:764; Viana e al., 2000, *Mol. Microbiol.* 36:570), and a ptsHI deletion derivative of the selected strain will be mutagenized in order to generate a Lactic Acid Bacteria that is incapable of growing on minimal glucose media. Both nitrosoguanidine and ethyl methanesulfonate will be employed as mutagens and if necessary antibiotic enrichment procedures and MacConkey Glucose selective plates will be used to identify a Lactic Acid Bacteria ptsHI mutant that is xylose-selective and incapable of metabolizing glucose.

An isogenic glucose-selective Lactic Acid Bacteria strain will then be generated. Like *E. coli*, Lactic Acid Bacteria strains which contain mutations in either the genes that encode for the xylose transporter or isomerase or xylulokinase enzymes cannot utilize xylose as a sole carbon source (Lokman et al., 1991, *Mol Gen Genet.* 230:161; Chaillou et al., 1998, *Appl. Environ. Microbiol.* 64:4720; Erlandson et al., 2000, *Appl Environ Microbiol.* 66:3974). Chemical mutagenesis will be employed to generate a Lactic Acid Bacteria xyl mutant using the same "optimal" strain as described above. The result will be two isogenic strains of a species of Lactic Acid Bacteria, one which is xylose-selective and a second which is glucose-selective.

Next, fermentations of sugar mixtures will be conducted. Analogous to the more comprehensive research completed for *E. coli* in the above Examples, as part of this experiment with Lactic Acid Bacteria, we will complete fermentations of a medium composed of xylose and glucose using the substrate-selective strains. A unique aspect of many Lactic Acid Bacteria is their tendency to switch between heterofermentative and homofermentative conditions as a function of growth rate and redox conditions (Garrigues et al., 1997, *J. Bacteria* 179:5282). We will study both low growth rates at which mixed-acid (and ethanol) production is expected and high growth rates at which lactic acid production dominates. Previous difficulties with ethanol production in Lactic Acid Bacteria (Nichols et al., 2003, *J. Indust. Microbiol. Biotechnol.* 30:315) may be attributed to the competition between lactic acid formation and ethanol formation under high growth, homofermentative conditions. Although the focus will be the simultaneous utilization of xylose and glucose and not on product formation, per se, an understanding of product formation and its relationship to operational parameters is important in the interpretation and analysis of the results.

We will conduct chemostat experiments to establish the operating ranges for the processes and the performance under both homofermentative and heterofermentative conditions. We will determine for each strain the biomass yields, specific rates of consumption/production of dissolved and gaseous compounds, and the maintenance energy requirements resulting from the various genetic perturbations. We will study the strains individually on single-substrate media, then single strains on dual-substrate media, then multiple strains on dual-substrate media. We will assess whether the presence of the unutilized sugar impacts the ability of the strain to consume its exclusive substrate, determine the operating optimal conditions and ranges for the conversion process, and examine how the distribution of end-products is affected by the co-culture. These experiments will facilitate the development of future processes to convert lignocellulosic hydrolysates efficiently into useful products with other organisms such as yeast.

Example 10

Substrate-Selective *Saccharomyces Cerevisiae*

Because yields and productivity are the two most important economic factors in the manufacture of fuel ethanol, the preferred microorganism of choice is *Saccharomyces cerevisiae*. This yeast ferments ethanol very efficiently and can tolerate the highest ethanol concentrations of any known microorganism. Unfortunately, the use of *S. cerevisiae* to produce fuel ethanol from lignocellulosic hydrolysates is problematic, because it cannot utilize the pentose sugars xylose and arabinose which are two of the most abundant sugars that are found in lignocellulosic hydrolysates. Researchers have attempted to solve this problem by constructing new *S. cerevisiae* derivatives that contain the genes required for xylose utilization. These new yeast derivatives can utilize xylose, however, when these yeasts are fed a mixed carbon source that contain glucose and xylose, the glucose must be consumed first, before any xylose can be utilized.

Our multiple cell approach can be readily applied to *S. cerevisiae*. *S. cerevisiae* strains that cannot utilize galactose can be constructed by deleting the GAL2, GAL1, GAL7, or GAL10 genes. These strains will be able to utilize glucose as a carbon source. *S. cerevisiae* strains that cannot utilize glucose can be constructed by deleting the GLK1, HXK1, and HXK2 genes or the HXT1, HXT2, HXT3, HXT4, HXT6, HXT7, and SNF3 genes. These strains will be able to utilize galactose as a carbon source. *S. cerevisiae* strains that can utilize xylose or arabinose can be constructed by importing these pathways from other yeasts such as *Pichia stipitis* or *Ambrosiozyma monospora* which are able to utilize these sugars. By knocking out the genes that are required for glucose and galactose utilization in *S. cerevisiae* strains that have been genetically modified to consume xylose and/or arabinose, new strains can be created which are only able to utilize xylose and/or arabinose. Concurrent use of a combination of these strains would be able to produce ethanol very efficiently.

Example 11

A Substrate-Selective Co-Fermentation Strategy with *Escherichia coli* Produces Lactate by Simultaneously Consuming Xylose and Glucose We report a new approach for the simultaneous conversion of xylose and glucose sugar mixtures which potentially could be used for lignocellulosic biomass hydrolysate (Eiteman et al., 2009 *Biotechnol. Bioeng.* 201:822-827). We used this approach to demonstrate the production of lactic acid. This process uses two substrate-selective strains of *Escherichia coli*, one which is unable to consume glucose and one which is unable to consume xylose. In addition to knockouts in pflB encoding for pyruvate formate lyase, the xylose-selective (glucose deficient) strain *E. coli* ALS1073 has deletions of the glk, ptsG and manZ genes while the glucose-selective (xylose deficient) strain *E. coli* ALS1074 has a xylA deletion. By combining these two strains in a single process the xylose and glucose in a mixed sugar solution are simultaneously converted to lactate. Furthermore, the biomass concentrations of each strain can readily be adjusted in order to optimize the overall product formation. This approach to the utilization of mixed sugars eliminates the problem of diauxic growth, and provides great operational flexibility.

Recently, we proposed a multi-organism approach to utilizing a sugar mixture (Eiteman et al., 2008, *J Biol Eng* 2:3). This approach involves introducing into a mixed substrate stream several strains which each are able to consume only one particular substrate. Each strain will therefore effectively ignore other substrates while it carries out the one target conversion. An advantage of such "substrate-selective uptake" is that the system can adapt to fluctuations in the feed stream; that is, cultures can grow in concert with a variable feed composition. Also, metabolic engineering strategies could ultimately focus on improving the individual production strains independently. For example, the glucose-selective strain could be improved for the generation of a particular product without having to compromise on how those changes might impact the conversion of xylose to that product.

In this example we use substrate-selective strains of *Escherichia coli* for the formation of a product of interest, such as lactic acid, in a mixed-sugar defined medium. Lactate has previously served as a convenient product to show conversion of xylose and glucose mixtures using a ptsG mutant of *E. coli* in complex medium (Dien et al., 2002, *J Industr Microbiol* 29:221-227). Over 1.5M lactate can be generated by this organism having several key mutations under carefully controlled conditions (Zhu et al., 2007, *Appl Environ Microbiol* 73:456-464). In the present study, we use metabolically engineered strains to study the feasibility of a two-strain strategy for the simultaneous conversion of xylose and glucose into lactate.

Methods

Strains

The *Escherichia coli* strains used in this study are listed in the following table. Deletion mutants from the Keio collection (Baba et al., 2006, *Mol Syst Biol.* 2:1-11) were moved into strains by P1 transduction, and Kan(R) was subsequently deleted using the curable pCP20 plasmid which overproduces Flp recombinase (Cherepanov and Wackernagel, 1995, *Gene* 158:9-14). The Δ(pflB::Cam) deletion was moved into strains by P1 transduction. Using aerobic shake flask cultures, we verified that ALS1073 would not consume glucose, while ALS1074 would not consume xylose.

| Strain | Genotype | Source |
|---|---|---|
| JW1087-2 | Δ(araD-araB)567 ΔlacZ4787(:::rrnB-3) Δ(rhaD-rhaB)568 hsdR514 rph-1 λ-ΔptsG763::(FRT)Kan | 1 |
| JW1808-1 | Δ(araD-araB)567 ΔlacZ4787(:::rrnB-3) Δ(rhaD-rhaB)568 hsdR514 rph-1 λ-ΔmanZ743::(FRT)Kan | 1 |
| JW2385-1 | Δ(araD-araB)567 ΔlacZ4787(:::rrnB-3) Δ(rhaD-rhaB)568 hsdR514 rph-1 λ-Δglk-726::(FRT)Kan | 1 |
| JW3537-1 | Δ(araD-araB)567 ΔlacZ4787(:::rrnB-3) Δ(rhaD-rhaB)568 hsdR514 rph-1 λ-ΔxylA748::(FRT)Kan | 1 |
| MG1655 | F- λ- | 2 |
| NZN111 | F+ λ-rpoS396(Am) rph-1 ldhA::Kan ΔpflB:Cam | 3 |
| ALS1038 | F- λ-ΔxylA748::FRT | 4 |
| ALS1048 | F- λ-ΔptsG763::FRT ΔmanZ743::FRT Δglk-726::FRT | 4 |
| ALS1073 | F- λ-ΔpflB::Cam ΔptsG763::FRT ΔmanZ743::FRT Δglk-726::FRT | 4 |
| ALS1074 | F- λ-ΔpflB::Cam ΔxylA748::FRT | 4 |

1) Baba et al., 2006, *Mol Syst Biol.* 2: 1-11.
2) Guyer et al., 1980, *Cold Spring Harbor Symp Quant Biol* 45: 135-140
3) Bunch et al., 1997, *Microbiology* 143: 187-195.
4) This example

Growth Conditions

Basal medium contained (per L): 13.3 g $KH_2PO_4$, 4.0 g $(NH_4)_2HPO_4$, 1.2 g $MgSO_4 \cdot 7H_2O$, 13.0 mg $Zn(CH_3COO)_2 \cdot 2H_2O$, 1.5 mg $CuCl_2 \cdot 2H_2O$, 15.0 mg $MnCl_2 \cdot 4H_2O$, 2.5 mg $CoCl_2 \cdot 6H_2O$, 3.0 mg $H_3BO_3$, 2.5 mg $Na_2MoO_4 \cdot 2H_2O$, 100 mg Fe(III)citrate, 8.4 mg $Na_2EDTA \cdot 2H_2O$, 1.7 g citric acid, and 4.5 mg thiamine·HCl. General "BXG" medium contained basal medium plus xylose plus glucose. Two different compositions of xylose and glucose were used in this study, "B2X3G" medium comprised basal medium with nominally 20 g/L xylose and 30 g/L glucose, while B3X2G contained 30 g/L xylose and 20 g/L glucose. For each bioreactor experiment, a single strain was first grown in a tube containing 10 mL BXG medium, then 5 mL transferred to 50 mL BXG medium in a 250 mL shake flask. All flasks were incubated at 37° C. and 250 rpm (19 mm pitch), and the pH was adjusted to 6.7 with 20% NaOH. For those fermentations in which a single strain was used, when the OD of the shake flask culture reached approximately 4, the flask contents were diluted with BXG medium so that 100 mL having an effective OD of 1.0 was used to inoculate the bioreactor. For those experiments in which two strains were used in a single process, the contents of two shake flasks were diluted with BXG medium to 100 mL so that each strain had an effective OD of 1.0 (i.e., in the 100 mL volume). Identical "BXG" media were used for a given experimental sequence consisting of tube culture, shake flask culture and bioreactor culture.

Fermentation

Batch experiments were carried out in a 2.5 L bioreactor (Bioflo 2000, New Brunswick Scientific Co. Edison, N.J., USA) containing 1.0 L BXG medium. Each experiment consisted of two process phases maintained at 37° C. During an initial aerobic growth phase with duration as reported in the results, air was sparged into the fermenter at a flowrate of 1.0 L/min, and the agitation was 1000 rpm to ensure no oxygen limitation. The pH was controlled at 6.7 using 28% (w/v) $NH_4OH$. During the second anaerobic phase, $N_2$ was supplied at 0.2 L/min, the agitation was reduced to 200 rpm, and the pH was controlled at 6.7 using 20% (w/v) NaOH. The product yields reported are the amount of product formed divided by the amount of sugar consumed during the second production phase.

Analyses

The optical density at 600 nm (OD) (DU-650 spectrophotometer, Beckman Instruments, San Jose, Calif.) was used to monitor cell growth, and this value was correlated to dry cell mass. Previously described liquid chromatography methods were used to quantify organic compounds (Eiteman and Chastain, 1997, *Anal Chem Acta* 338:69-75).

Results and Discussion

*Escherichia coli* ALS1074 has a knockout in the xylA gene encoding for xylose isomerase, rendering ALS1074 unable to consume xylose. The xylose-selective strain ALS1073 has mutations in the three genes involved in glucose uptake (Curtis and Epstein, 1975, *J Bacteriol* 122:1189-1199), rendering it unable to consume glucose: ptsG encodes the Enzyme IICB$^{Glc}$ of the phosphotransferase system (PTS) for carbohydrate transport (Postma et al., 1993, Microbiol Rev 57:543-594), manZ encodes the IID$^{Man}$ domain of the mannose PTS permease (Huber and Erni, 1996, *Eur J Biochem* 239:810-817), glk encodes glucokinase (Curtis and Epstein, 1975, *J Bacteriol* 122:1189-1199). Each strain also has a mutation in pflB encoding pyruvate formate lyase, which causes a severe metabolic bottleneck at pyruvate under anaerobic conditions, curtailing growth in the absence of acetate and diverting most carbon to lactate (de Graef et al., 1999, *J Bacteriol* 181:2351-2357).

Figure 10:
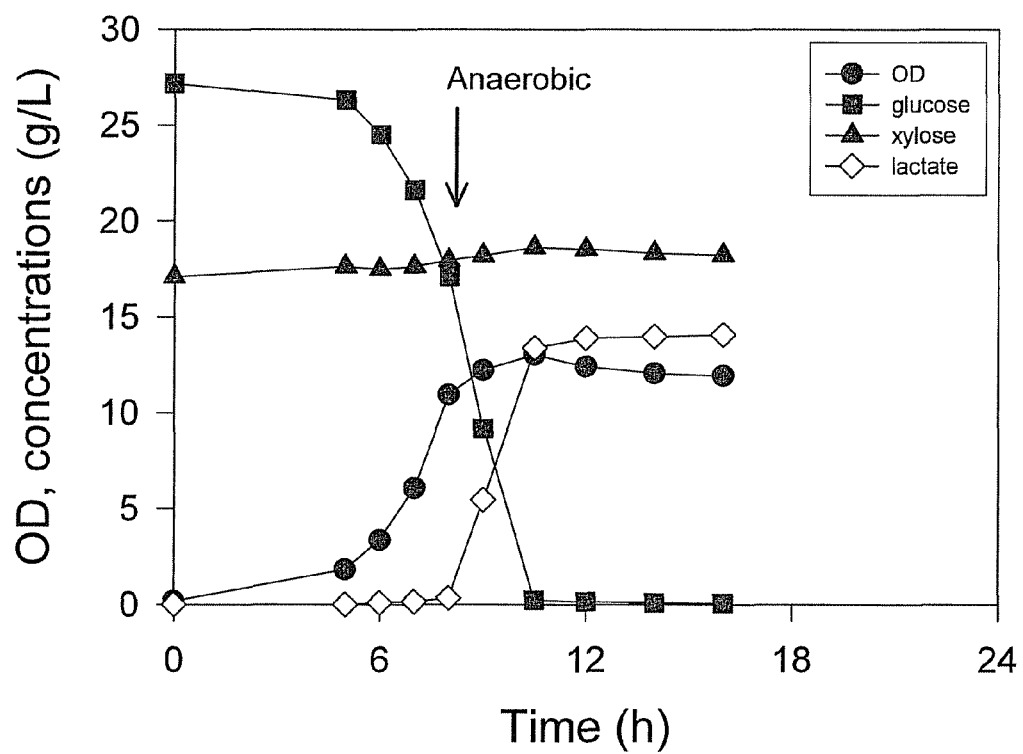
FIG. 10 shows batch aerobic-anaerobic process of *Escherichia coli* ALS1074 on a mixture of glucose (■) and xylose (▲). After 8 h of aerobic growth, the culture was switched to anaerobic conditions as indicated. The OD (●) and lactate concentration (◇) were measured over the course of the fermentation.

In our first experiment, we grew ALS1073 or ALS1074 (i.e., each strain alone) under aerobic conditions in B2X3G medium, and after 8 h switched to anaerobic conditions. Sugar concentrations were used which represented the levels found in most lignocellulosic hydrolysates. ALS1074 consumed approximately 10 g/L glucose during the 8 h of growth to an OD of 11.5 (FIG. 10). After initiating anaerobic conditions, growth stopped and the remaining 17 g/L glucose was converted into about 14 g/L lactate within 3 h for a yield of 0.83 g/g (based on substrate consumed during the anaerobic production phase only). About 1.5 g/L succinate and less than 0.5 g/L acetate and ethanol as by-products were also generated during the anaerobic phase (yields: 0.095 g succinate/g glucose, 0.004 g acetate/g glucose, 0.028 g ethanol/g glucose). Lactate was formed at a constant specific rate of 1.2 g/g·h during the anaerobic phase, and throughout the process the xylose concentration remained unchanged.

Figure 11:
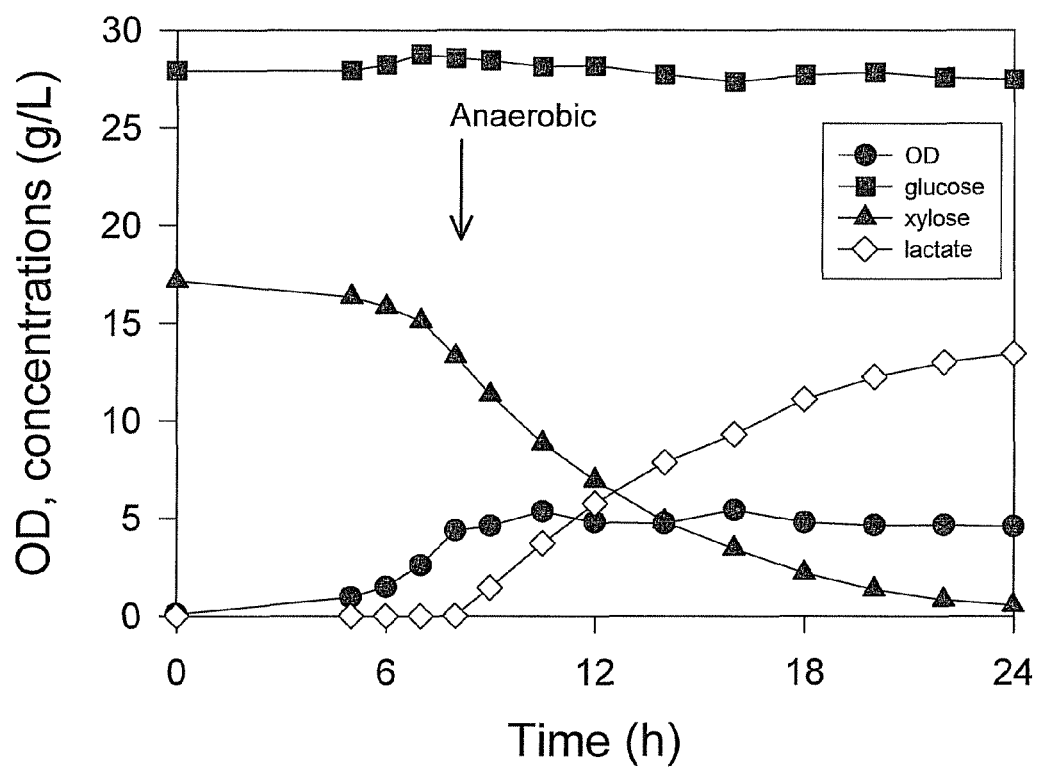
FIG. 11 shows batch aerobic-anaerobic process of *Escherichia coli* ALS1073 on a mixture of glucose (■) and xylose (▲). After 8 h of aerobic growth, the culture was switched to anaerobic conditions as indicated. The OD (●) and lactate concentration (◇) were measured over the course of the fermentation.

ALS1073 consumed 4 g/L xylose during the 8 h aerobic growth phase to an OD of 4.5 (FIG. 11). During the anaerobic phase, the remaining 13.3 g/L xylose was converted to 13 g/L lactate at a yield near 1.0 g/g. The conversion of xylose to lactate was completed in 14 h. The rate of xylose consumption during the anaerobic phase by ALS1073 appears to be much slower than the rate of glucose consumption by ALS1074 (shown in FIG. 10). However, the biomass concentration was appreciably different between the two experiments—the biomass concentration of ALS1073 after 8 h of growth on xylose was less than 40% of the biomass concentration using ALS1074 on glucose. The specific rate of xylose consumption was 0.92 g/g·h at the onset of the anaerobic phase, whereas the rate of xylose consumption was 0.49 g/g·h during the latter portion of the anaerobic phase. Less than 0.5 g/L succinate (0.023 g succinate/g xylose) and no acetate and ethanol were generated as by-products, and the glucose concentration remained unchanged during the entire process.

Figure 12:
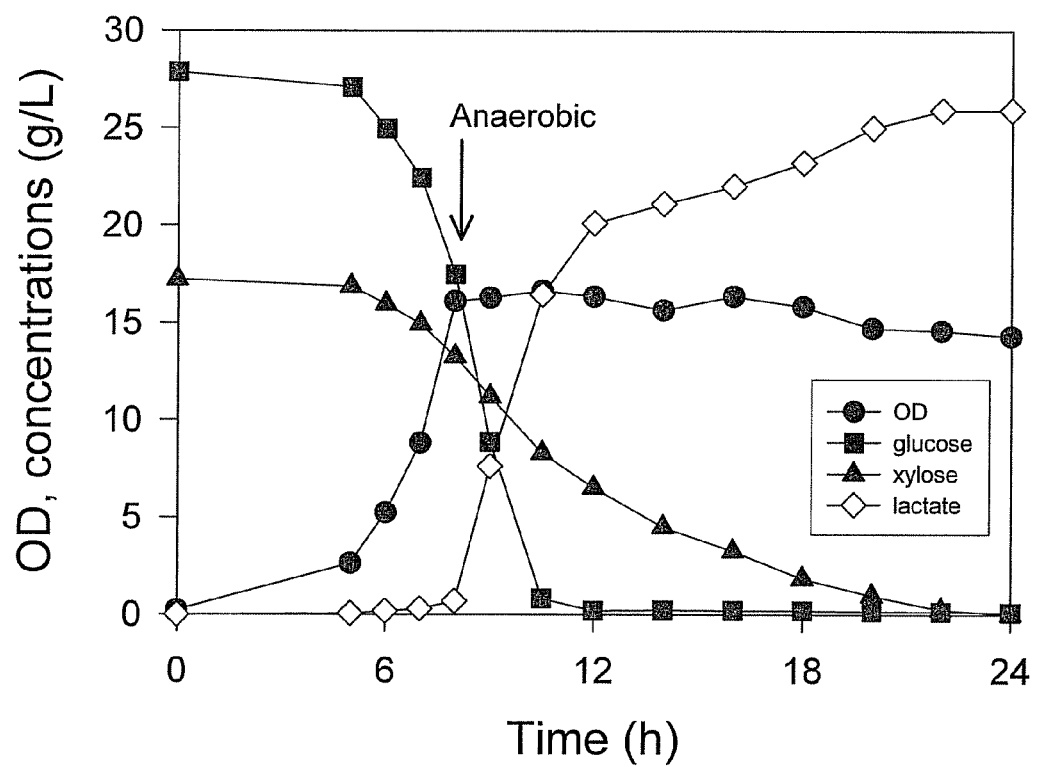
FIG. 12 shows batch aerobic-anaerobic process of two *Escherichia coli* strains ALS1073 and ALS1074 on a mixture of glucose (■) and xylose (▲). After 8 h of aerobic growth, the culture was switched to anaerobic conditions as indicated. The OD (●) and lactate concentration (◇) were measured over the course of the co-fermentation.

In a second experiment, both ALS1073 and ALS1074 were inoculated into a single bioreactor containing the same xylose-glucose defined medium B2X3G. In this two-strain co-fermentation, care was taken to ensure that each strain was inoculated at approximately the same cell density that was used in the two different one strain processes. After 8 h of growth the anaerobic phase was similarly initiated, and at this time the culture had consumed about 4 g/L xylose and 10 g/L glucose to achieve an OD of 16 (FIG. 12). During the anaerobic phase, the remaining glucose was consumed in less than 3 h, and the xylose was consumed in about 12 h. Assuming that the measured OD of 16 represents an OD of 11.5 for ALS1074 and an OD of 4.5 for ALS1073 (values observed in the previous single organism cases), then the specific rate of glucose consumption during the anaerobic phase was 1.6 g/g·h, and the rate of xylose consumption was initially 1.2 g/g·h. The 17.5 g/L glucose and 13.3 g/L xylose present at the onset of the anaerobic phase were converted to 25.9 g/L lactate, for a yield of 0.84 g lactate/g total sugar. The same minor by-products were also generated, with yields based on xylose+glucose of 0.063 g succinate/g, 0.008 g acetate/g, 0.014 g ethanol/g. Interestingly, the final by-product concentrations were approximately the sum of what was observed in the two single-substrate-consumption experiments. For example, the final succinate concentration when two strains converted two sugars was 1.94 g/L, which is approximately the sum of the concentrations observed in the xylose-only (0.30 g/L) and glucose-only (1.62 g/L) experiments. This experiment demonstrates that the two strains acted independently in the conversion of xylose and glucose to lactate.

Although the two-strain process as implemented (FIG. 12) performed exactly as each single strain process, the two-strain process exposed one important shortcoming. Under the conditions of the experiment, the volumetric rate of xylose consumption did not match the volumetric rate of glucose consumption. Specifically, because glucose exhaustion occurred in less than 3 h of anaerobic conditions but xylose consumption required over 12 hours, the process inefficiently consumed only one of two possible substrates for the final 10 h. The overall process was essentially limited by the volumetric rate of xylose consumption. To maximize overall productivity, the two consumption rates ideally would allow both glucose and xylose to become exhausted at about the same time. Moreover, these two consumption rates should be adjustable so that this optimal productivity occurs regardless of the initial concentrations of xylose and glucose.

The volumetric consumption rate (Q) is equal to the specific consumption rate (q) times the biomass concentration (X). So, for the xylose-selective strain $Q_{xylose}=q_{xylose}X_{xylose}$. One general method to increase Q is to increase q, for example using metabolic engineering approaches directed toward altering the pathways involving that substrate. Another general method to increase Q is to increase the biomass concentration of the strain. Because $q_{glucose}$ is about 30% greater than $q_{xylose}$ during the anaerobic phase for the particular two-strain bioprocess we conducted, a higher cell density for the xylose-selective strain $X_{xylose}$ is needed relative to $X_{glucose}$ in order to match the two values of Q. In a one-strain approach for the simultaneous consumption of xylose and glucose, only one biomass concentration exists, and the absence of this additional degree of flexibility prevents the matching of utilization rates for multiple substrates.

Figure 13:
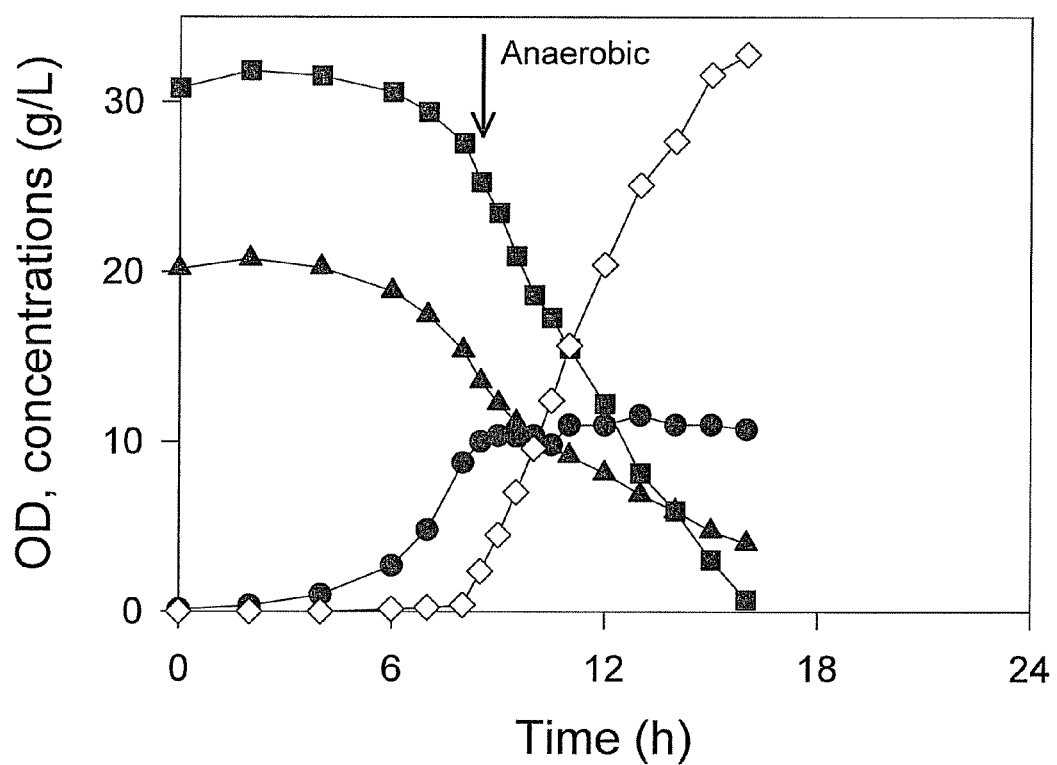
FIG. 13 shows batch aerobic-anaerobic process of two *Escherichia coli* strains ALS1073 and ALS1074 on a mixture of glucose (■) and xylose (▲). At the start of the process the bioreactor was inoculated with ALS1073, and after two hours the bioreactor was inoculated with ALS1074. After 8.5 h of aerobic growth, the culture was switched to anaerobic conditions as indicated. The OD (●) and lactate concentration (◇) were measured over the course of the co-fermentation.

To illustrate the flexibility in aligning consumption rates, we repeated the two-strain experiment using the same B2X3G medium. In this case, we increased the cell density of the xylose-consuming strain by providing this strain more time for growth prior to switching to the non-growth production phase. Specifically, using a nearly identical medium with 20 g/L xylose and 31 g/L glucose, at the start of the process (t=0) the bioreactor was only inoculated with the xylose-consuming strain ALS1073. Two hours after this inoculation, the bioreactor was inoculated with the glucose-consuming strain ALS1074, and at 8.5 h, anaerobic conditions commenced. Therefore, the xylose-consuming strain experienced 8.5 h of aerobic growth, while the glucose-consuming strain was allowed only 6.5 h of aerobic growth. At the time that anaerobic conditions commenced, the OD of the culture was approximately 10.5 with 27.6 g/L glucose and 15.4 g/L xylose (FIG. 13), and we estimate that about 60% of the biomass was ALS1073 while 40% of the biomass was ALS1074. In this experiment, the rates of glucose and xylose consumption were much more closely matched, and both sugars were consumed almost simultaneously. Thus, the two-sugar mixture was efficiently converted at a constant rate into 32 g/L lactate over the course of 8 h. We also observed about 2.5 g/L succinate and 0.5 g/L ethanol and acetate (yields based on xylose+glucose: 0.84 g lactate/g, 0.065 g succinate/g, 0.004 g acetate/g, 0.012 g ethanol/g). The small sacrifice made in the unnecessarily large glucose consumption rate was more than offset by the improvement in the xylose-consumption rate.

Figure 14:
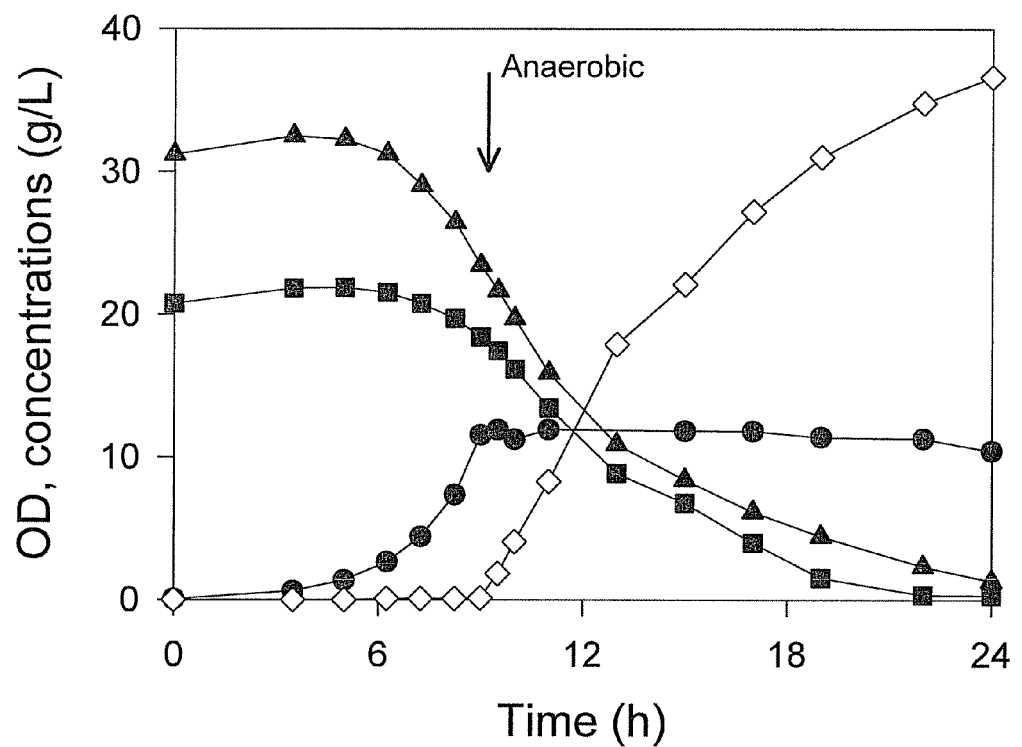
FIG. 14 shows batch aerobic-anaerobic process of two *Escherichia coli* strains ALS1073 and ALS1074 on a mixture of glucose (■) and xylose (▲). At the start of the process the bioreactor was inoculated with ALS1073, and after 3.1 hours the bioreactor was inoculated with ALS1074. After 9.1 h of aerobic growth, the culture was switched to anaerobic conditions as indicated. The OD (●) and lactate concentration (◇) were measured over the course of the co-fermentation.

This particular method can be used to tailor the volumetric consumption rates for other concentrations of xylose and glucose. To demonstrate this flexibility, we conducted a bioprocess using a medium with initially 33 g/L xylose and 22 g/L glucose (nominally B3X2G). Because this medium contains 50% more xylose than glucose, an even higher cell density of the xylose-selective strain ALS1073 relative to the glucose-selective strain ALS1074 is required compared to the previous process using B2X3G medium. Therefore, at the start of the process (t=0) the culture was inoculated with ALS1073, while the inoculation with ALS1074 occurred 3.1 h later. Anaerobic conditions commenced at 9.1 h; thus, ALS1073 experienced 9.1 h of growth while ALS1074 experienced 6 h of growth. At the onset of anaerobic conditions, the OD of the culture was approximately 12 with 19.5 g/L glucose and 20.4 g/L xylose (FIG. 14). Again, the rates of glucose and xylose consumption were closely matched, and the two-sugar mixture was efficiently converted into 37 g/L lactate with a lactate-sugar yield of 0.88 g/g. Other products generated during anaerobic conditions included 0.069 g succinate/g, 0.010 g acetate/g, 0.009 g ethanol/g.

Conclusions

The process described in this study demonstrates the simultaneous conversion of sugar mixtures into one particular product, lactate. In this case, two strains were used which are each selective in their consumption of the two carbon sources present, xylose and glucose. Excluding substrate consumption in a strain by gene deletions represents a new approach for the conversion of multiple substrates into a desired product. If additional carbon sources were present, then additional strains could be constructed to ensure each strain exclusively converted one substrate into the desired product. One advantage demonstrated is that not only can xylose and glucose be simultaneously converted to a product like lactate, but the conversion rates of each sugar can be individually modulated to optimize the overall process. In this study, this "alignment" of consumption rates was exacted by inoculating the culture at different times, thereby allowing each strain to reach a desired cell density prior to switching to a non-growth production phase. However, other means might be available to align consumption rates in other circumstances, for example, using differential inocula densities or introducing genetic modifications which affect growth rates. The multi-strain approach therefore offers a significant advantage over any one-strain approach to mixed sugar utilization. Presumably another advantage, not explored in this study, is that each strain can be independently engineered genetically to maximize one sugar-to-product conversion.

Example 12

Acetate Consumption by *Pseudomonas* Spp

We studied the exclusive consumption of acetate by *E. coli*; specifically we compared numerous *E. coli* strains to learn which strains had the highest rate of acetate consumption. We found that most *E. coli* strains have growth rates of about 0.25 $h^{-1}$ on acetate, whereas the fastest *E. coli* strain showed a growth rate of about 0.35 $h^{-1}$. Because we are interested in developing a strain that consumes acetate as quickly as possible, we also tested several *Pseudomonas* species.

Like *E. coli*, most *Pseudomonas* are prototrophic, do not require amino acids supplements, and grow very quickly on minimal defined media. We tested three different strains of *Pseudomonas* and two of them had growth rates of about 0.70 $h^{-1}$ on acetate. This growth rate is about 3 times faster than an average *E. coli* and twice as fast as the fastest *E. coli*. Clearly, a trait found in some *Pseudomonas* strains allows a significant improvement in acetate consumption compared to *E. coli*, and can be used to enhance the acetate selective cell used in the method of the invention.

Two general approaches can be used to capitalize on our observations of the high growth rate of *Pseudomonas* on acetate. One approach is to find the genes encoding the enzymes in *Pseudomonas* which are responsible for high growth rate and transfer them into an *E. coli* designed to consume acetate exclusively. To that end, additional *Pseudomonas* strains, including those that have been completely sequenced, will be evaluated for their ability to grow using acetate as a sole carbon source, and the fastest grower will be selected. Genomic DNA will be prepared and large fragments will be cloned into an expression vector to ensure the preservation of operons. Libraries will be transformed in MG1655, a wild-type *E. coli* strain, and fast growers on a minimal acetate medium will be selected. Optionally, the genes responsible for the enhanced growth on acetate can then be characterized.

A second approach is to knock out some or all the carbohydrate-consuming genes in *Pseudomonas*, so that this strain is becomes acetate-selective. To this end, we can knock out the genes responsible for glucose and xylose consumption in the *Pseudomonas* strain that has the fastest growth rate on acetate and has been completely sequenced. Because the genes responsible for glucose and xylose metabolism have been shown to be highly homologous in several bacteria, we will be able to construct the required knockouts in *Pseudomonas*.

Essentially, we either bring the *Pseudomonas* "fast genes" into the microbe that cannot consume anything else (e.g., an acetate-selective *E. coli*), or we make a fast-acetate-consumer (e.g., the *Pseudomonas* strains that grow quickly on acetate) unable to consume anything else. For the production of biofuels, either *Pseudomonas* or *E. coli* can be used interchangeably remove the acetate from ligocellulosic hydrolysates. For the production of some industrial high-value commodity biochemicals, such as pyruvic acid, where the end use is nutraceuticals, being able to implement the acetate removal using *E. coli* may be preferable.

Example 13

Furfural Consumption

We recently isolated about 20 bacterial strains, including strains that appear visually to be *Pseudomonas* spp., which consume furfural as the sole carbon source (furfural-selective strains). These strains are ideal candidates for use as inhibitor selective cells in the method of the invention, where the inhibitor is furfural.

The approach to capitalizing on these cells will be similar to the approach outlined for developing acetate-selective strains in Example 12. Specifically, we will isolate and transfer the gene(s) from the selected isolates which are responsible for its growth furfural into an *E. coli* strain which has been engineered not to be able to consume sugars. To this end, we will make DNA libraries of genes from selected isolates, clone them into an *E. coli* expression vector, transform *E. coli* and select clones that can grow on furfural. As in Example 12, no specific genetic information is necessary about the source strain.

Possibly the resulting inhibitor selective strain can be engineered to consume both acetate and furfural; alternatively, two different inhibitor selective cells, one that is selective for acetate, and another that is selective for furfural, can be created and used in the method of the invention. The acetate-selective strain would consume acetate exclusively (i.e., it does not have the furfural degradation genes), and the furfural-selective strain would consume only furfural by having an additional knockout in the acetate degradation genes acs and ackA.

Example 14

Selective Microbial Removal of Acetate from Sugar Mixtures

Acetic acid is an unavoidable constituent of the biomass hydrolysate generated from the acetylated hemicellulose and lignin. The removal of acetate from hydrolysate is necessary for improving the microbial production of biochemicals. In this study, acetate is selectively removed from mixtures of glucose and xylose by metabolically engineered *Escherichia coli* strain ALS1060 with mutations in the phosphotransferase system (PTS) genes of glucose (ptsG, manZ), glucokinase (glk) and xylose (xylA). In batch culture, ALS1060 consumed acetate exclusively at first, and began to consume the two sugars only at a very slow rate when the acetate in the medium was essentially exhausted. In order to eliminate all sugar consumption, we also examined effects of knockouts in the crr gene and glucose non-specific PTS genes malX, fruA, fruB, and bglF in ALS1060. The crr knockout showed the least sugar consumption, and a batch process with a strain having five knockouts (ptsG manZ glk xylA crr) showed less than 1 g/L of sugar consumption after 92 h.

Conversion of lignocellulosic biomass to fuels and chemicals by microbial fermentation is a promising alternative to petroleum-based processes (Zaldivar et al., 2001, Appl. Microbiol. Biotechnol. 56: 17-34). Lignocellulosic materials are inexpensive and readily available, and are largely carbohydrates in the form of cellulose and hemicellulose (Klinke et al., 2004, Appl. Microbiol. Biotechnol. 66:10-26). However, several challenges remain which limit the wide use of lignocellulosic biomass. One challenge is that biomass hydrolysates contain inhibitors such as acetic acid (acetate). Acetate is an unavoidable product of hemicellulose depolymerization since xylose is acetylated in lignocellulose (Timmel, 1967, Wood Sci. Technol. 1(1):45-70; Sarkanen and Ludwig, 1971, Lignins: occurrence, formation, structure and reactions. Wiley-Interscience, New York, pp 345-372; Fengel and Wegener, 1989, Wood Chemistry, ultrastructure, reactions. Walter de Gruyter, Berlin; Chesson et al., 1993, J. Sci. Food. Agric. 34(12):1330-1340; Torssell, 1997, Natural product chemistry: a mechanistic, biosynthetic and ecological approach. Apotekarsocieteten, Stockholm). Xylose conversion appears particularly sensitive to acetate, with a 0.15% concentration reducing by 50% the yield of ethanol using *E. coli* (Nelle et al., 2003, Enzyme. Microb. Technol. 33(6):786-792). Similarly, because its membrane is highly permeable to acetate, *S. cerevisiae* is particularly susceptible to acetate inhibition (Casal et al., 1998, Appl. Environ. Microbiol. 64(2):665-668). Acetate also exacerbates other inhibitory effects; for example, furfuryl alcohol and 2-furfural reduce ethanol yield by *E. coli* more in the presence of acetate (Zaldivar and Ingram, 1999, Biotechnol. Bioeng. 66:203-210; Zalivar et al., 1999, Biotechnol. Bioeng. 65:24-33; Zaldivar et al., 2000, Biotechnol. Bioeng. 68:524-530). Although the generation of some inhibitors might be reduced by judicious design of the hydrolysis process or by genetic improvements in the biomass itself, elimination of all acetate in a lignocellulosic hydrolysate does not currently seem feasible.

A wide variety of strategies have been proposed to ameliorate the effect of acetate on fermentation (Lasko et al., 2000, Appl. Microbiol. Biotechnol. 54(2):243-247). For example, ion exchange (Horvath et al., 2004, Appl. Biochem. Biotechnol. 114:525-538; Chandel et al., 2007, Biores. Technol. 98:1947-1950) or activated carbon (Benson et al., 2005, Appl. Biochem. Biotechnol. 124:923-934) can prepare reduce acetate concentration. Similarly, extraction with ethyl acetate reduces acetic acid (and furfural, vanillin and 4-hydroxybenzoic acid), leading to a 93% improvement in ethanol yield using *Pichia stipitis* (Wilson et al., 1989, Appl. Microbiol. Biotechnol. 31:592-596). These approaches involve an additional processing step which significantly affects overall process costs (Von Sivers et al., 1994, Biotechnol. Prog. 10:555-560). Preferably, an approach should not only leave the production microorganisms unaffected but remove acetate completely at very low cost.

We have previously reported a biological strategy for selectively removing components from a mixture (Eiteman et al., 2008, *J Biol Eng* 2:3). The approach involves the "design" of a single strain that will utilize only one component in a mixture. Since many organisms including *Escherichia coli* readily consume acetate when this compound is the sole carbon source (Holms 1986, Curr. Top Cell. Regul. 28:69-105), acetate might be removed from a mixture of xylose, glucose and acetate (for example) with a strain that is genetically prevented from consuming xylose and glucose. Glucose uptake primarily is mediated by glucosephosphotransferase [ptsG (gpt) encodes the EIICB$^{glc}$ component (Postma et al., 1993, Microbiol. Rev. 57(3):543-594)], mannosephosphotransferase (EC 2.7.1.69) [manZ (mpt) encodes the EII enzyme (Curtis et al., 1975, J. Bacteriol. 122(3):1189-1199)], and ATP-dependent glucokinase (EC 2.7.1.2) encoded by the glk gene (Curtis et al., 1975, J. Bacteriol. 122(3):1189-1199). Knocking out the ptsG, manZ and glk genes prevents *E. coli* from consuming glucose in a short batch process, while a xylA mutant is unable to consume xylose (Eiteman et al., 2008, *J Biol Eng* 2:3). Thus, a strain with the four knockouts (i.e., ptsG manZ glk xylA) might therefore prevent consumption of both sugars but allow normal acetate metabolism.

Other cellular processes could also be involved in glucose transport. Due to considerable sequence homology between EII proteins, genes corresponding to other carbohydrate PTS systems might also transfer glucose into the cell. For example, the malX gene of the maltose PTS system encodes a protein that binds to glucose and displays nearly 35% sequence identity to the protein encoded by ptsG (Reidl and Boos, 1991, J. Bacteriol. 173:4862-4876), and the EII$^{fru}$ protein of the fructose specific PTS system (expressed by the fruA gene) shows similarity with EII$glu$ (Prior and Kornberg, 1988, J. Gen. Microbiol. 134:2757-2768). The bgl operon in *E. coli* (consisting of 3 structural genes bglC, bglS, and bglB) encode components of the specific transport protein phospho-β-glucosidase (EII$^{bgl}$) (Schnetz et al., 1987, J. Bacteriol. 169: 2579-2590) and shows significant sequence homology to the carboxyl-terminal section of the EII$^{glu}$ protein (Bramley and Kornberg, 1987, Proc. Natl. Acad. Sci. USA 84:4777-4780). EIIIA*glu* is phosphorylated during PEP-phosphotransfer of glucose, and strains lacking the crr gene express nomial levels of all PTS proteins except for EIIA$^{glu}$ (Saier and Roseman, 1976, J Biol. Chem. 251:6598-605). Since none of these carbohydrate transport genes is known to be involved in acetate metabolism, knockouts of these genes could eliminate any residual glucose uptake without affecting acetate consumption.

Using a mixture of xylose, glucose and acetate as a model for biomass hydrolysate, we constructed an acetate-selective strain which does not consume xylose and glucose, and to demonstrate that this strain could effectively remove acetate from a mixture containing these sugars.

Materials and Methods

Bacterial Strains

The *Escherichia coli* strains studied are shown in the following table.

| Strain | Genotype |
|---|---|
| MG1655 | F-λ-rph-1 (wild type) |
| ALS1060 | MG1655 ΔptsG763::(FRT) ΔmanZ743::(FRT) Δglk-726::(FRT) ΔxylA748::(FRT) |
| ALS1072 | MG1655 ΔptsG763::(FRT) ΔmanZ743::(FRT) Δglk-726::(FRT) ΔxylA748::Kan |
| ALS1122 | ALS1060 Δcrr::(FRT) |
| ALS1123 | ALS1060 ΔfruA::(FRT) |
| ALS1124 | ALS1060 ΔfruB::(FRT) |
| ALS1125 | ALS1060 ΔbglF::(FRT) |
| ALS1127 MalX | |
| ALS1122-Kan | This is the strain with crr knockout and Kan cassette |

Shake Flask Growth Conditions

Basal medium (BA10) contained (per L): 13.3 g KH$_2$PO$_4$, 4.0 g (NH$_4$)$_2$HPO$_4$, 1.2 g MgSO$_4$.7H$_2$O, 13.0 mg Zn(CH$_3$COO)$_2$.2H$_2$O, 1.5 mg CuCl$_2$.2H$_2$O, 15.0 mg MnCl$_2$.4H$_2$O, 2.5 mg CoCl$_2$.6H$_2$O, 3.0 mg H$_3$BO$_3$, 2.5 mg Na$_2$MoO$_4$.2H$_2$O, 100 mg Fe(III)citrate, 8.4 mg Na$_2$EDTA.2H$_2$O, 1.7 g citric acid, 0.0045 g thiamine.HCl, and 10 g/L acetate using Na(CH$_3$COO).3H$_2$O. BA2 medium was identical except it contained 2 g/L acetate. Both BA2 and BA10 media were supplemented with xylose and/or glucose as described in the text. Acetate, xylose and glucose were autoclaved separately, sterily combined, and neutralized with NaOH to a pH of 7.0. Concentrations are reported as acetate without consideration of the counterion.

Growth characteristics of *E. coli* strains in BA2 medium with 2 g/L glucose are shown in the following table.

| Name of strain | ΔOD/Δt (AU/h) | ΔG/Δt (mg/L · h) |
|---|---|---|
| ALS1060 | 0.018 | 18.0 |
| ALS1122 | -0.003 | 8.4 |
| ALS1123 | 0.017 | 16.9 |
| ALS1124 | 0.016 | 20.3 |
| ALS1125 | 0.035 | 28.7 |
| ALS1127 (malX) | 0.023 | 21.4 |

Growth Conditions

For shake flask experiments, 50 mL BA2 medium contained 2 g/L glucose in 250 mL baffled shake flasks at 37° C. and 350 rpm (19 mm pitch).

For fermentation experiments, the selected strain was first grown (5 mL) in a 10 mL shaking test tube containing 5 g/L tryptone, 2.5 g/L yeast extract, 5 g/L NaCl and 2.5 g/L acetate, then transferred to a baffled 250 mL shake flask containing 50 mL BA10 incubated at 37° C. and 250 rpm (19 mm pitch). When the OD of the culture reached 2.0-2.5, the contents of the shake flask were transferred to a bioreactor.

Batch fermentations were carried out at 1.0 L using BA10 in a 2.5 L bioreactor (Bioflo 2000, New Brunswick Scientific Co. Edison, N.J., USA). Air was sparged into the fermenter at a flowrate of 1.0 L/min, and the agitation was 500 rpm to ensure no oxygen limitation. The pH was controlled at 7.0 using 20% (w/v) NaOH or 20% (v/v) H$_2$SO$_4$, and the temperature was controlled at 37° C.

Fed-batch experiments initially operated in batch mode and contained BA10 medium but with 5 g/L acetate. When the OD reached 3.0-3.5, sugar supplemented BA10 medium was fed at an exponentially increasing rate to achieve a constant growth rate of 0.07 h$^{-1}$. Concentrated NH$_4$OH was used for base control, and the feed solution contained 100 mg/L kanamycin.

Assays

The optical density measured at 600 nm absorbance (OD) (UV-650 spectrophotometer, Beckman Instruments, San Jose, Calif.) was used to monitor cell growth. Glucose, xylose, acetate, and other organic by-products were quantified as previously described (Eiteman and Chastain, 1997, Anal. Chim. Acta. 338:69-75).

Results

Batch Growth on Acetate

Figure 15:
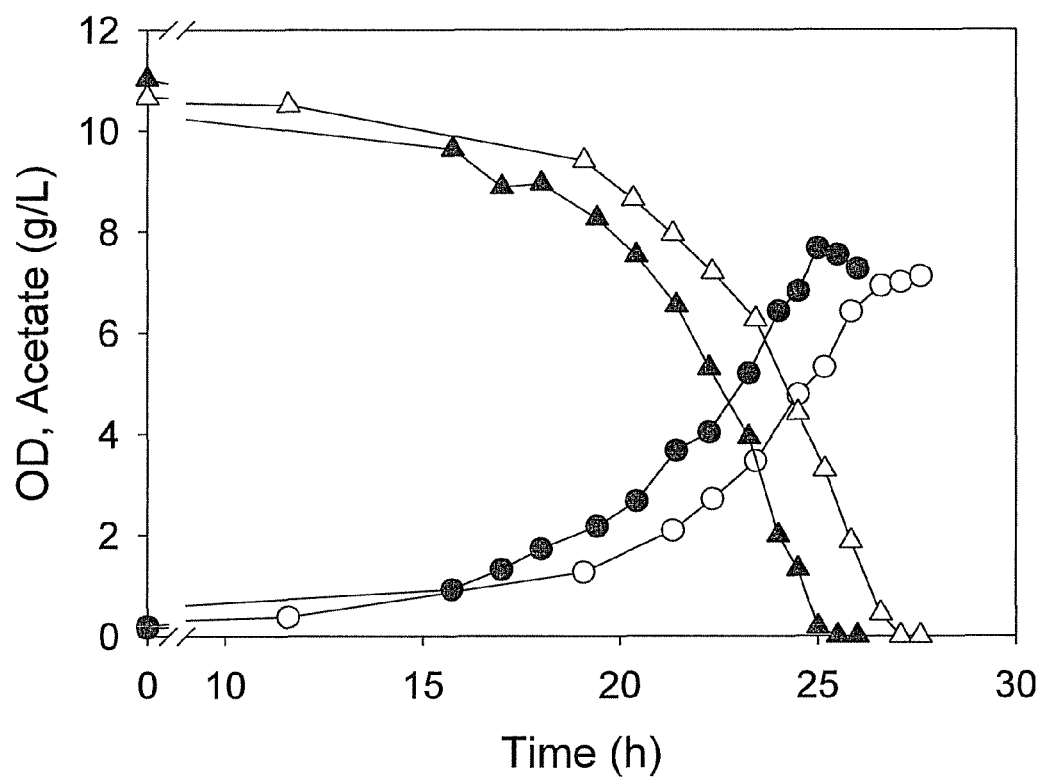
FIG. 15 shows aerobic batch culture of *E. coli* MG1655 (hollow symbols) and ALS1060 (solid symbols) on BA10 medium which contains acetate (▲, ▵) as the sole carbon source. The OD (●, ○) was measured over the course of the processes.

*Escherichia coli* MG1655 is a common wild-type strain (Jensen 1993, J. Bacteriol. 175:3401-3407) which should consume acetate as the sole carbon source. We first sought to verify this expectation in aerobic batch growth, and FIG. 15 shows the results in BA10 medium (i.e., initial concentration of 10 g/L acetate). MG1655 foimed approximately 2.5 g/L cells (OD=7.1) at a specific growth rate of 0.23 h$^{-1}$.

*E. coli* ALS1060 (see Example 2) has four knockouts of genes coding for proteins involved in the utilization of xylose and glucose: ptsG encodes the Enzyme IICB$^{Glc}$ of the phosphotransferase system (PTS) for carbohydrate transport (Postma et al., 1993, Microbiol. Rev. 57(3):543-594), manZ encodes the IID$^{Man}$ domain of the mannose PTS permease (Huber, 1996, Eur. J. Biochem. 239(3):810-817), glk encodes glucokinase (Curtis and Epstein 1975, J. Bacteriol. 122(3): 1189-1199) while xylA encodes xylose isomerase. These four mutations should prevent the utilization of either xylose or glucose by ALS1060. In order to determine whether these mutations had any effect on the growth on acetate, we similarly grew ALS1060 in the same medium (FIG. 15). Like MG1655, ALS1060 formed 2.5 g/L cells (OD=7.7), and attained a specific growth rate of 0.22 h$^{-1}$.

Extended Batch Growth on Acetate in the Presence of Sugars

Figure 16:
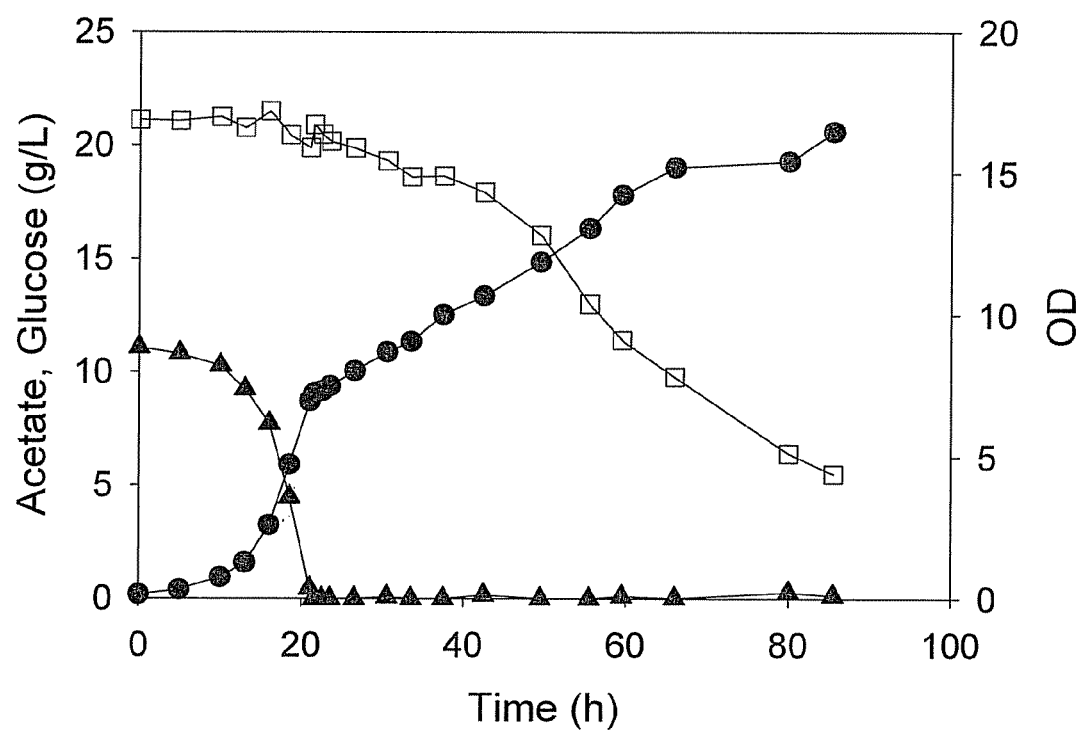
FIG. 16 shows aerobic batch culture of *E. coli* ALS1060 on BA10 medium with 20 g/L glucose. Glucose (□), acetate (▲) and the OD (●) were measured over the course of the process.

Our next objective was to determine whether acetate could be exclusively consumed from a mixture of sugars. Since ALS1060 contains knockouts involved in the consumption of xylose or glucose, the growth of this strain in a medium containing xylose, glucose and acetate is expected to identical to growth in the medium containing acetate alone. In order to test this prediction, we grew ALS1060 in batch culture over an extended period of time in BA10 medium in the presence of either 20 g/L glucose, 10 g/L xylose or in a mixture of 10 g/L xylose and 20 g/L glucose Batch culture using ALS1060 in BA10 medium containing 20 g/L glucose did result in exclusive acetate consumption during the first 20 h of the process (FIG. 16). Moreover, during growth on acetate the specific growth rate was 0.21 h$^{-1}$, identical to the growth rate observed in medium without acetate (FIG. 15). Interestingly, slow glucose consumption commenced about the time acetate was nearly exhausted (FIG. 16), and the specific growth rate of ALS1060 after acetate was exhausted was found to be 0.014 h$^{-1}$.

Figure 17:
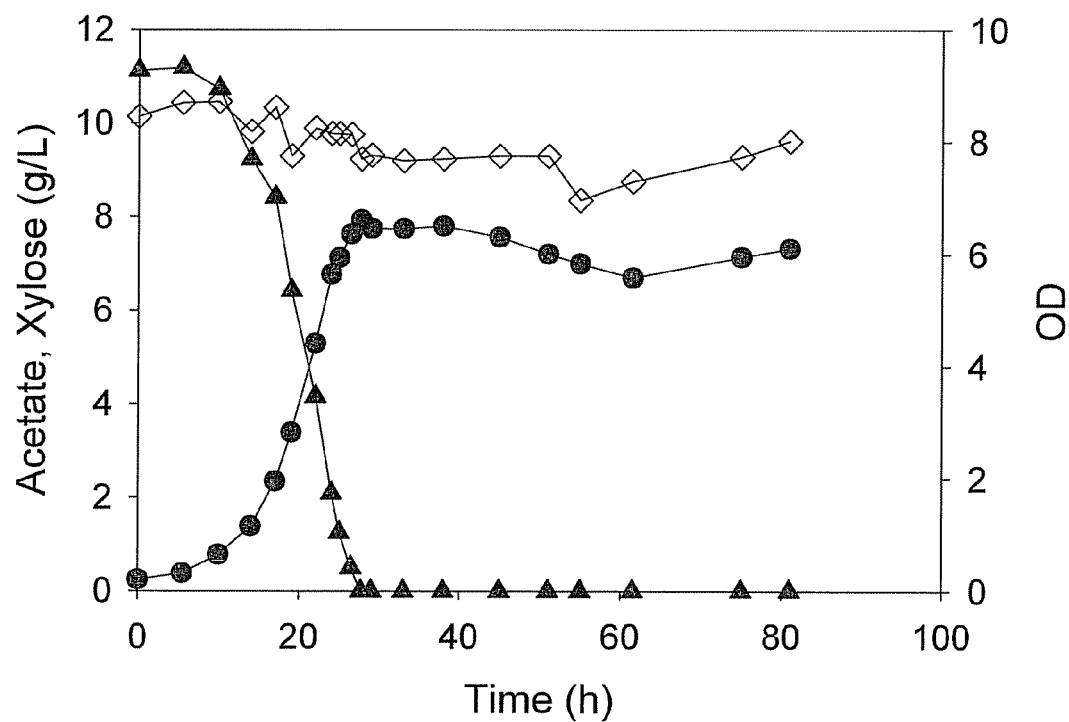
FIG. 17 shows aerobic batch culture of *E. coli* ALS1060 on BA10 medium with 10 g/L xylose. Xylose (◇), acetate (▲) and the OD (●) were measured over the course of the process.

During batch culture using BA10 medium containing 10 g/L xylose ALS1060 consumed exclusively acetate, and the concentration of xylose remained unaltered throughout the process (FIG. 17).

Figure 18:
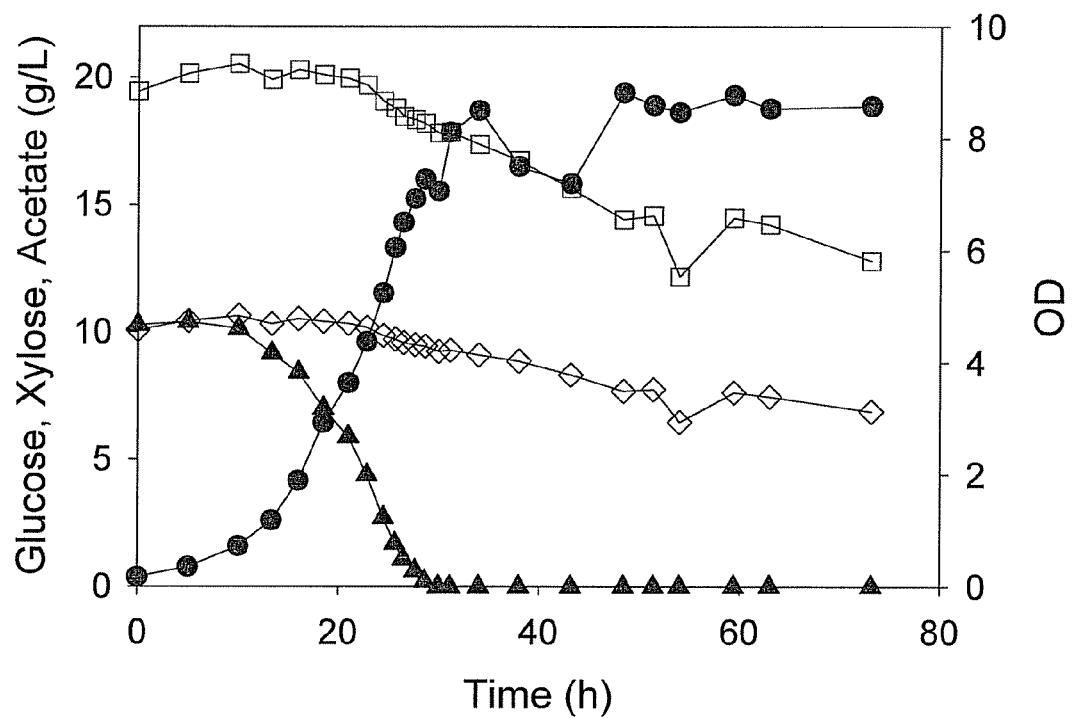
FIG. 18 shows aerobic batch culture of *E. coli* ALS1060 on BA10 medium with 20 g/L glucose and 10 g/L xylose. Glucose (□), xylose (◇), acetate (▲), and the OD (●) were measured over the course of the process.

In order to study how the presence of both sugars influenced acetate utilization, ALS1060 was inoculated into BA10 medium with 20 g/L glucose and 10 g/L xylose. In this case, ALS1060 consumed the acetate in 30 h, during which time less than 2 g/L glucose and 0.6 g/L xylose was consumed. Over the next 40 h, however, 7 g/L glucose and 3 g/L xylose were slowly consumed (FIG. 18).

The extended batch fermentations confirmed that ALS1060 could consume glucose and xylose in the absence of acetate. Further more it became clear that the inability of ALS1060 to consume xylose in the absence of glucose indicates that glucose is necessary for the consumption of xylose.

Comparison of Knockouts to Prevent Glucose Consumption

Because ALS1060 grew in the presence of glucose albeit slowly, E. coli must have another means to transport and utilize glucose. Mutations in the ptsG, manZ, and glk genes are insufficient to prevent glucose consumption. With the goal of completely eliminating glucose consumption, we next examined growth on BA2 with 2 g/L glucose of strains having mutations additionally in one of several other genes which encoding non-specific PTS proteins: malX encoding a protein of the maltose-specific PTS (ALS1127MalX), fruA or fruB encoding proteins of the fructose-specific PTS (ALS1123 and ALS1124, respectively); the bgl operon involved in the PTS of β-glucosides (ALS1125), and crr which encodes the EIIA$^{glu}$ (ALS1122). To compare growth and glucose consumption, two parameters were measured: the rate of glucose uptake for approximately 30 h beyond the time that acetate was exhausted ($\Delta G/\Delta t$), and the change in the optical density for approximately 30 h beyond the time that acetate was exhausted ($\Delta OD/\Delta T$). Compared to ALS1060, only ALS1122 (with the crr mutation) showed a significantly reduced rate of glucose consumption (8.4 mg/L·h). This strain also showed essentially no change in the optical density over the 30 h period, in contrast to the other strains.

Extended Batch Growth of ALS1122-Kan on Acetate in the Presence of Sugars

Figure 19:
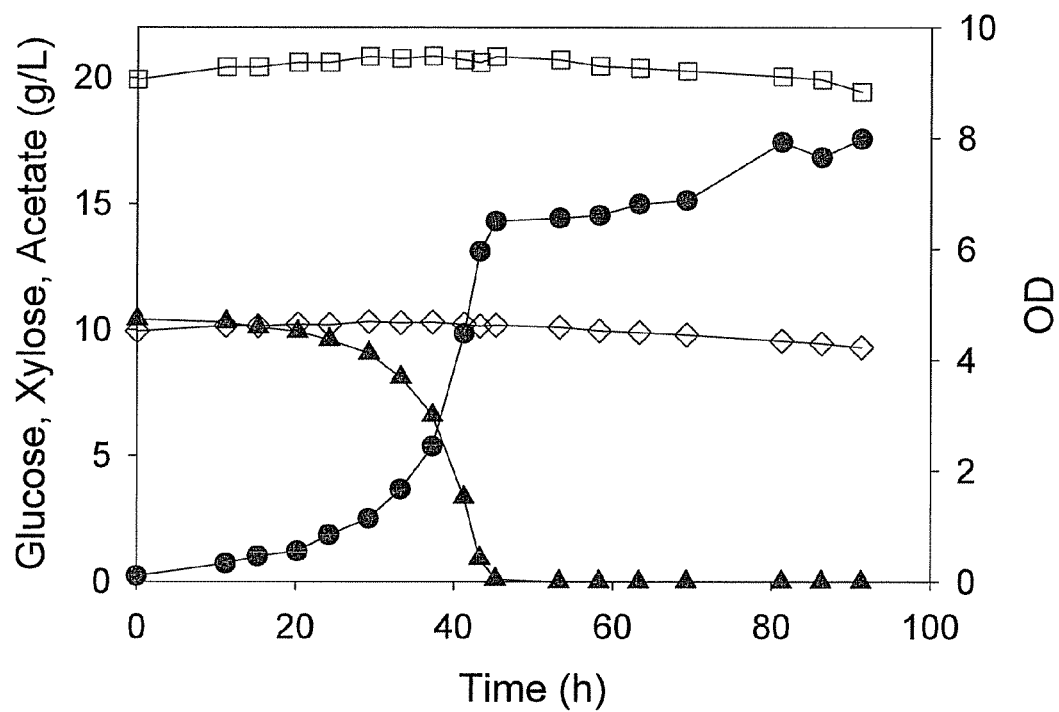
FIG. 19 shows aerobic batch culture of *E. coli* ALS1122-Kan on BA10 medium with 20 g/L glucose and 10 g/L xylose. Glucose (□), xylose (◇), acetate (▲), and the OD (●) were measured over the course of the process.

We next grew the strain containing the five knockouts (ptsG manZ glk xylA crr) and which additionally had drug resistance to kanamycin ("ALS1122-Kan") in BA10 medium with 20 g/L glucose and 10 g/L xylose. The results are shown in FIG. 19. In this case, less than 1 g/L glucose or xylose was consumed even after 92 h, even though the acetate had been completely consumed after 45 h.

Example 15

Arabinose-Selective and Xylose-Selective W Strains

E. coli is able to use each of the five principal monosaccharides found in lignocellulosic hydrolysate. We examined the wild-type W strain on each of these five carbon sources, and the specific growth rates were found to be 1.00 h$^{-1}$ (glucose), 0.84 h$^{-1}$ (xylose), 0.94 h$^{-1}$ (arabinose), 0.66 h$^{-1}$ (galactose) and 0.46 h$^{-1}$ (mannose). We selected W to generate substrate-selective strains because this strain generally grew fastest on these five carbohydrates.

Figure 20:
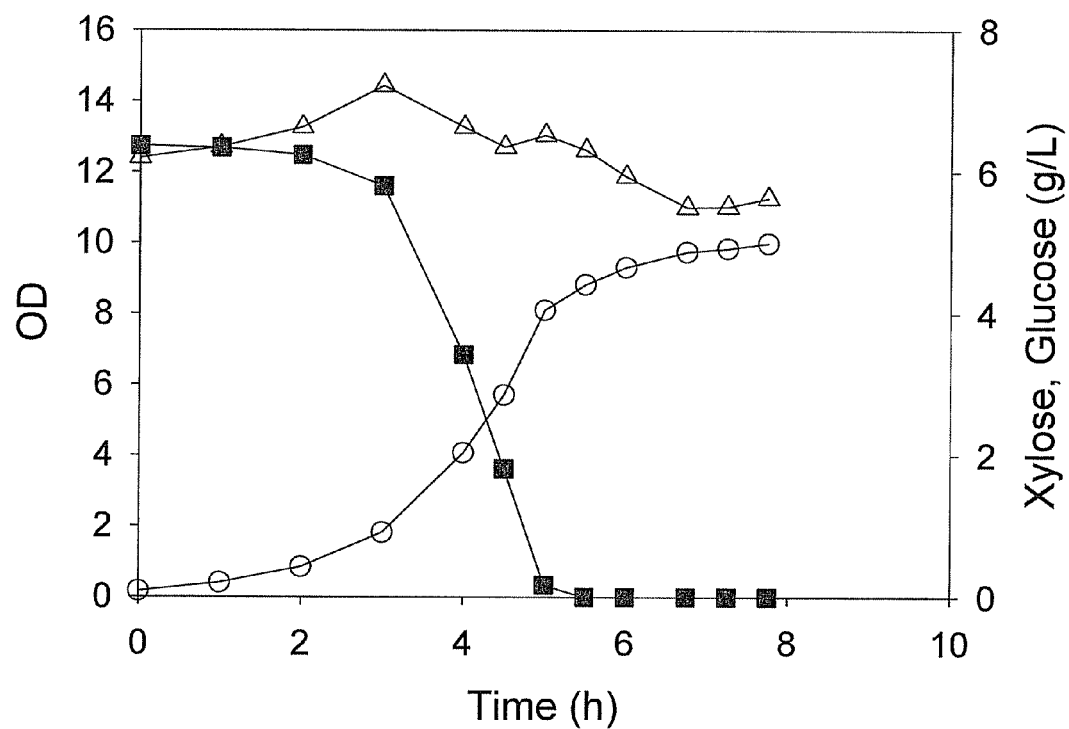
FIG. 20 shows growth and substrate consumption of *E. coli* KD777 on a mixture of xylose (■) and glucose (Δ). The OD (○) was measured over the course of the processes.

KD777 is wild-type W strain of E. coli with knockouts in the ptsG, manZ and glk genes, a set of genes which has been described as preventing growth on glucose (Curtis and Epstein, 1975 J Bacteria 122:1189). In a controlled batch process KD777 consumed 7 g/L xylose completely in 5.5 h with a maximum specific growth rate of 0.81 h$^{-1}$, essentially the same growth rate observed when W was grown in this medium. In the presence of both xylose and glucose, xylose was again completely consumed in about 5.5 h, during which time only 0.3 g/L glucose was consumed (FIG. 20). In the presence of glucose the maximum growth rate during xylose consumption was 0.78 h$^{-1}$.

Figure 21:
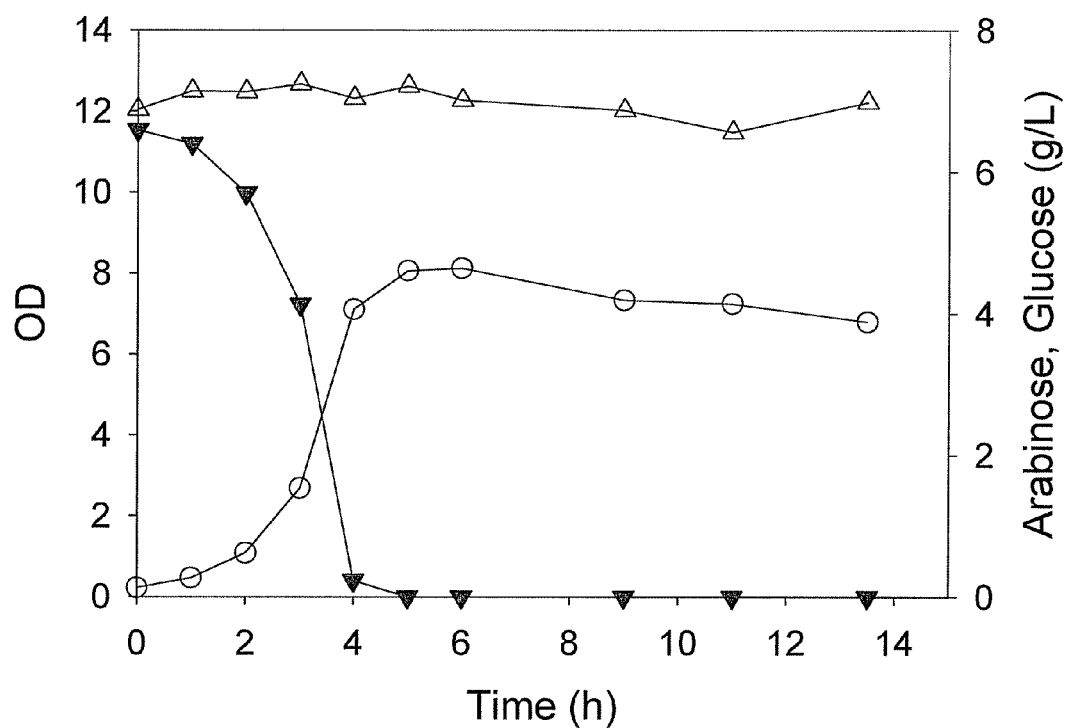
FIG. 21 shows growth and substrate consumption of *E. coli* KD777 on a mixture of arabinose (▼) and glucose (Δ). The OD (○) was measured over the course of the processes.

In a controlled batch process KD777 consumed 7 g/L arabinose completely in less than 5 h with a maximum specific growth rate of 0.84 h$^{-1}$. In a medium containing both arabinose and glucose, arabinose was consumed in 5 h at a mean growth rate of 0.81 h$^{-1}$, and glucose was not consumed during the first 14 h of the process (FIG. 21). Thus, arabinose has been consumed without any consumption of glucose, and additional mutations would permit this strain to accumulate a desired product from arabinose without affecting glucose.

Additional crr Knockout

Figure 22:
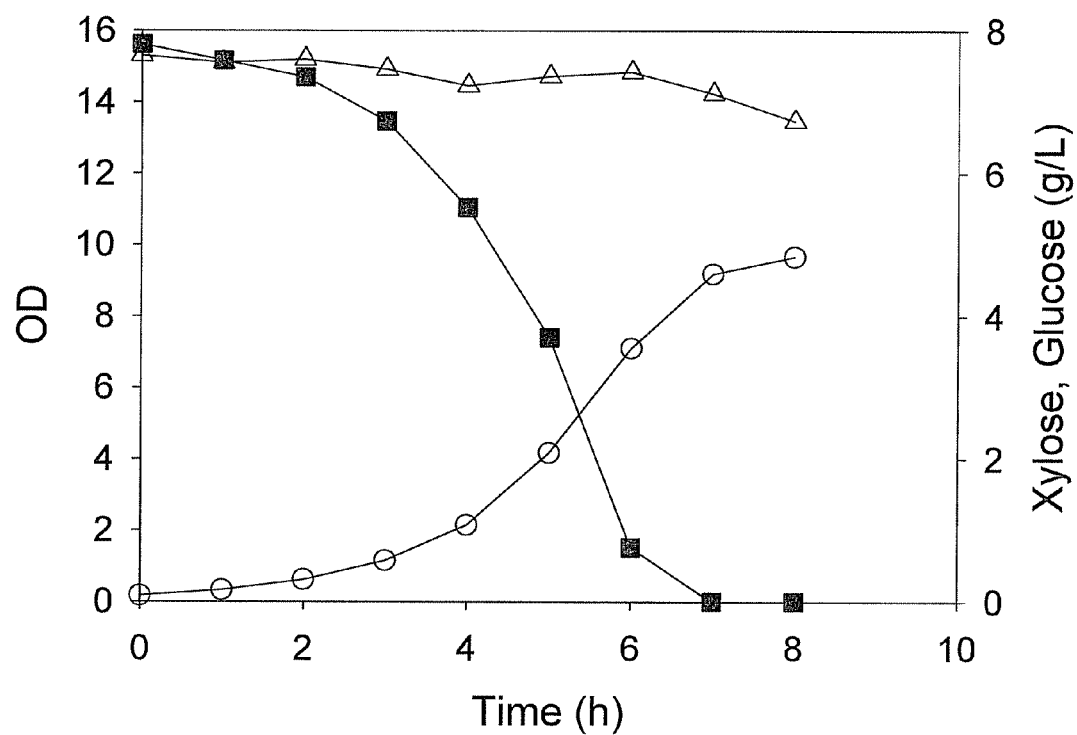
FIG. 22 shows growth and substrate consumption of *E. coli* KD915 on a mixture of xylose (■) and glucose (Δ). The OD (○) was measured over the course of the processes.
Figure 23:
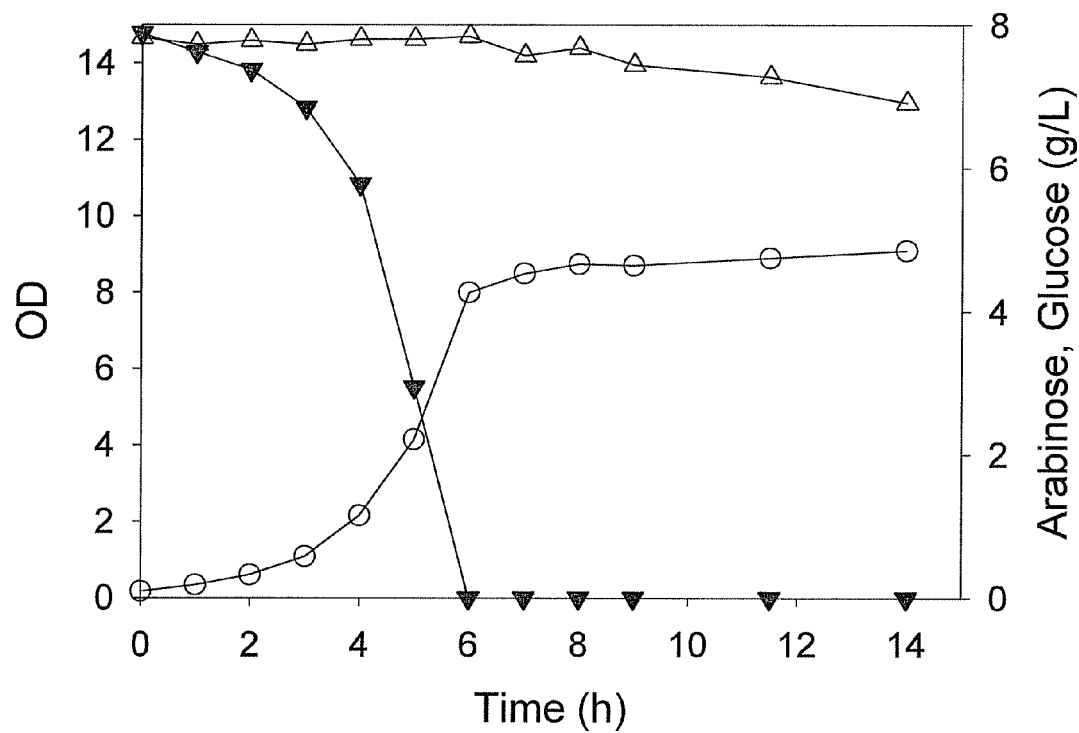
FIG. 23 shows growth and substrate consumption of *E. coli* KD915 on a mixture of arabinose (▼) and glucose (Δ). The OD (○) was measured over the course of the processes.
Figure 24:
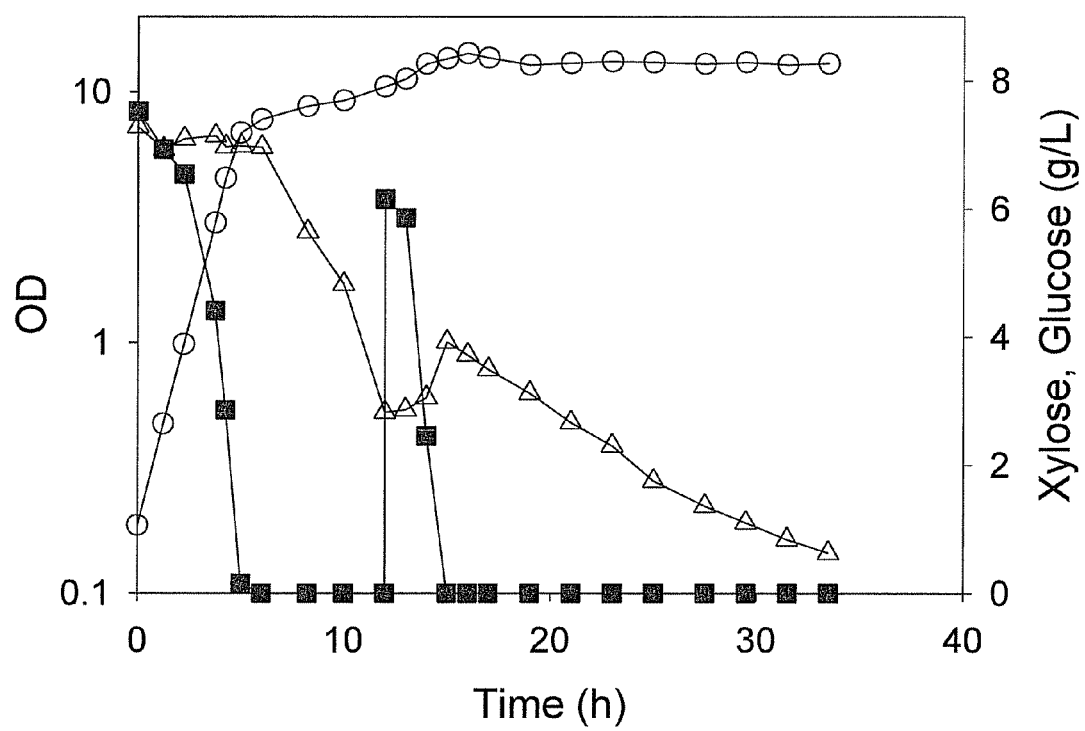
FIG. 24 shows growth and substrate consumption of *E. coli* KD777 on a mixture of xylose\ and glucose. Xylose was reintroduced into the medium after the initial xylose had been exhausted. OD: ○; xylose: ■; glucose: Δ.
Figure 25:
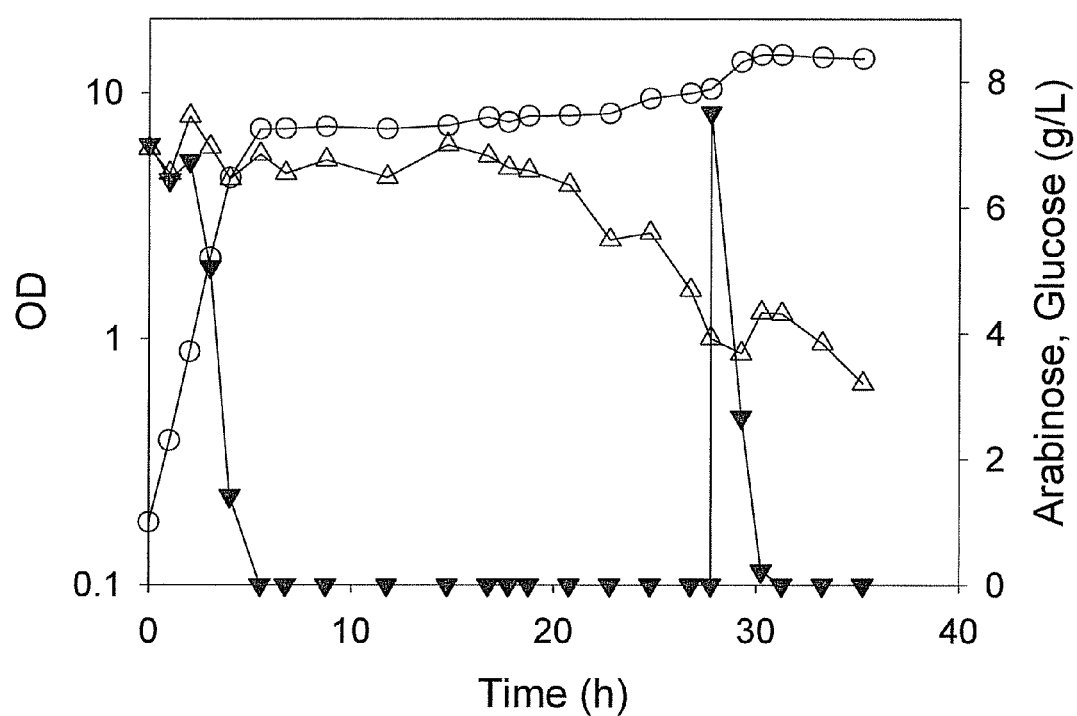
FIG. 25 shows growth and substrate consumption of *E. coli* KD777 on a mixture of arabinose and glucose. Arabinose was reintroduced into the medium after the initial arabinose had been exhausted. OD: ○; arabinose: ▼; glucose: Δ.

KD915 contains the ptsG, glk and manZ knockouts like KD777, but additionally has a knockout in the crr gene. The crr gene encodes for the Enzyme IIA component of the phosphotransferase system for glucose uptake. When KD915 consumed xylose as the sole carbon source, this strain attained a specific growth rate of 0.65 h$^{-1}$, about 20% lower than observed for KD777. In the presence of both xylose and glucose, xylose was consumed at a growth rate of 0.62 h$^{-1}$ (FIG. 22). Similarly, 7 g/L arabinose as the sole carbon source was consumed by KD915 with a specific growth rate of 0.64 h$^{-1}$, about 20% lower than KD777. In a medium containing both arabinose and glucose, arabinose was consumed at a mean growth rate of 0.64 h$^{-1}$, and glucose was consumed only slowly only after arabinose was depleted (FIG. 23).

Example 16

Ethanol Production in Sugar Mixtures

ALS1074 (MG1655 xylA pflB) contains a knockout of the xylA gene and therefore is expected in a mixture of glucose and xylose to be glucose-selective; i.e., the strain will consume glucose but not xylose. ALS1073 (MG1655 ptsG manZ glk pflB) contains three knockouts in glucose uptake and is therefore expected in a mixture of glucose and xylose to be xylose-selective; i.e., the strain will consume xylose but not glucose. These two strains were transformed with plasmid pTrc99A-pdc.adhB containing the pyruvate decarboxylase (pdc) and alcohol dehydrogenase (adhB) genes from Zymomonas mobilis. The presence of these two enzymes has been previously shown to endow E. coli with the ability to accumulate significant ethanol (Ingram and Conway 1988 Appl. Env. Microbiol. 54(2):397-404). ALS1073 and ALS1074 were individually and simultaneously grown in a medium containing nominally 15 g/L glucose and 10 g/L xylose. Specifically, 50 mL of medium was used in a 250 mL shake flask operating at a temperature of 37 C and an agitation of 250 rpm. The cultures were induced with 1 mM IPTG 8 h after inoculation. Anaerobic conditions were simulated 12 h after inoculation by reducing the agitation to 75 rpm. For each of the three experiments performed in duplicate (ALS1073 alone, ALS1074 alone, and ALS1073 and ALS1074 together), a sample was taken at the beginning of the experiment, and again at the end. The results are shown in the following table.

|  |  | ALS1074 alone | | ALS1073 alone | | ALS1073 + ALS1074 | |
| --- | --- | --- | --- | --- | --- | --- | --- |
|  |  | Exp 1 | Exp 2 | Exp 1 | Exp 2 | Exp 1 | Exp 2 |
| Xylose (g/L) | Start | 9.8 | 10.0 | 9.2 | 8.9 | 8.6 | 8.8 |
|  | End | 9.7 | 9.9 | 2.2 | 1.5 | 0.1 | 0 |
| Glucose (g/L) | Start | 13.1 | 13.5 | 14.0 | 13.6 | 12.8 | 13.1 |
|  | End | 0.4 | 0.2 | 13.3 | 13.5 | 0.3 | 0.2 |
| Ethanol (g/L) |  | 2.8 | 2.9 | 2.2 | 2.4 | 5.7 | 5.8 |
| Optical Density |  | 9.0 | 7.6 | 2.0 | 2.2 | 8.7 | 9.1 |

For ALS1074, essentially all of the glucose was consumed and none of the xylose, resulting in an accumulation of about 2.8 g/L ethanol. For ALS1073, essentially all of the xylose was consumed but none of the glucose, resulting in an accumulation of an average of 2.3 g/L ethanol. When both ALS1073 and ALS1074 were used together on this sugar mixture, both sugars were consumed with about 5.7 g/L ethanol generated. The results demonstrate that the two-strain approach, in which each strain is designed to be selective for one sugar but the strains otherwise are identical, can effectively generate ethanol.

Example 17

Batch Growth of KD777 with Additional Pentose

Figure 7:
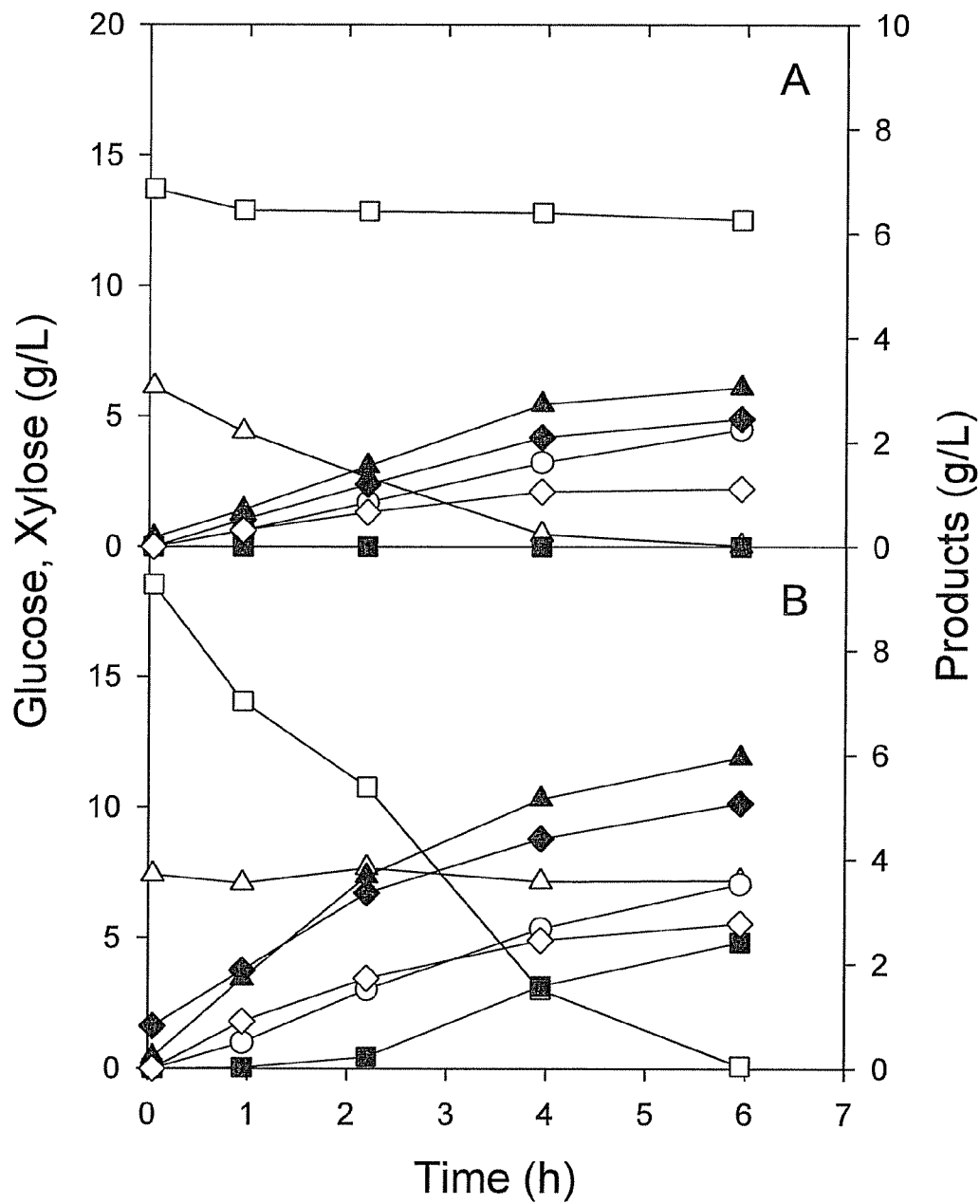
FIG. 7 shows batch anaerobic fermentation of single *Escherichia coli* strains on a mixture of glucose (□) and xylose (Δ). After 7 h of aerobic growth, xylose (for ZSC113) or glucose (for ALS1008) was added and anaerobic conditions commenced. The concentrations of formate (▲), lactate (■), succinate (○), acetate (♦) and ethanol (◇) were measured over the course of the anaerobic phase previously inoculated with A) ZSC113 only and B) ALS1008 only.

Results with batch growth of KD777 in xylose-glucose or arabinose-glucose mixtures suggested that the onset of glucose consumption did not occur until the pentose was depleted. We sought to verify whether the presence of pentose effectively hindered glucose metabolism in this strain by providing the culture with additional pentose after the initial quantity of pentose had been exhausted. For the case of a xylose-glucose mixture, we repeated the previous experiment, but added xylose to a concentration of about 7 g/L six hours after xylose was depleted, when the glucose concentration was approximately half its initial concentration (FIG. 7). The additional xylose was consumed within 3 h, and during the initial part of that interval the glucose concentration remained fixed. At the time when the xylose was just being depleted the glucose concentration increased from about 3 g/L to 4 g/L. After that additional dose of xylose had been exhausted, glucose consumption resumed and at a rate slower than the rate observed prior to the xylose addition.

For the case of an arabinose-glucose mixture, approximately 7 g/L arabinose was added about 20 h after arabinose was depleted, when the glucose concentration had reached approximately half its initial concentration (FIG. 8). This additional arabinose was consumed in two hours, and during that time the glucose concentration at first remained the same and then increased from about 3.5 g/L to 4.2 g/L. After that additional does of arabinose had been exhausted, glucose consumption resumed at approximately the same rate observed prior to the arabinose addition.

Without intending to be bound by theory, these observations may indicate that glucose is leaking into the cell through the xylose transport/metabolic pathway, and that it may be difficult in these particular cells to eliminate glucose uptake completely. Operationally, this is not a problem if fed-batch processing is used. If a continuous culture was run, it may be advantageous to keep the xylose concentration higher than a threshold value at which glucose begins to leak through the glucose-deficient strains. It may be prudent to maintain xylose metabolism in the continuous process, as opposed to a batch process, because over the course of a long time interval, the population of the cultures in the continuous culture could otherwise change in a suboptimal way.

Example 18

Sugar-Selective Cells Engineered to Accumulate Pyruvate

Earlier we demonstrated that 1.0 M (90 g/L) pyruvic acid (henceforth called pyruvate) can accumulate in less than 40 h with 70% mass yield from glucose in *E. coli* containing knockouts in the aceEF, pps, ldhA, poxB, pflB, arcA, and atpFH genes (Zhu et al., 2008. *Appl. Environ. Microbia* 74:6649). Pyruvate is a key precursor to numerous biochemical products including isobutanol (Atsumi et al., 2008. *Nature* 451:84-90), and in order to enhance accumulation of this precursor, one or more of these additional mutations can be introduced into in various sugar-specific strains of *E. coli*. The optimal xylose-to-pyruvate construct may not be identical to the optimal glucose-to-pyruvate construct, because the two mutations that reduce the biomass generation from glucose (arcA and atpFH) may be detrimental when pentoses such as xylose are the source for pyruvate production, since pentoses do not provide the cell with as much ATP as glucose. Arabinose- and xylose-specific strains which lack the arcA and atpFH mutations can also be constructed.

Example 19

Sugar-Selective Cells Engineered to Accumulate Succinate

Succinic acid (henceforth called succinate) and its derivatives are widely used as specialty chemicals in foods, pharmaceuticals, and cosmetics (Guettler et al. 1998), and it can serve as a starting material for many commercially important products (Zeikus et al. 1999). Moreover, succinate is listed among the U.S. Dept. of Energy's top 30 commodity chemicals from biomass (U.S. DOE 2004). During the anaerobic production of succinate, organisms fix the greenhouse gas $CO_2$ via carboxylation reactions and convert $C_3$ to $C_4$ metabolites. Through previous work, we have demonstrated that 0.8 M succinate (100 g/L) can accumulate in 72 h with 110% mass yield from glucose in *E. coli* containing knockouts in the pflB, ldhA and ptsG genes and harboring the pyruvate carboxylase (pyc) gene (see U.S. Pat. No. 7,749,740; Gokarn et al., Appl. Microbiol. Biotechnol., 56, 188-195 (2001); and Vemuri et al., Appl. Environ. Microbiol. 68(4):1715-27 (2002)).

A process for generating succinate is quite different than a process for pyruvate, and that has important consequences for the substrate-selective approach. Pyruvate is a growth-associated product, and thus the focus of the process is to insure that the individual strains are growing on their respective substrate. The process to generate succinate involves its accumulation as a non-growth associated product, and therefore the focus is insuring that the production phase is aligned so that each of the substrates are converted into the product succinate in proportion to each carbohydrate's availability. See Vemuri et al., J. Ind. Microbiol. Biotechnol., 28(6), 325-332 (2002); Vemuri et al., Appl. Env. Microbiol., 68(4), 1715-1727 (2002); and Challener, *Specialty Chemicals Magazine* 6:42-44 (2009)).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference.

The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for producing a biochemical comprising:
contacting an organic material comprising a mixture of sugars, with a plurality of sugar-selective cells comprising at least first and second sugar-selective *Escherichia coli* cells, wherein the first sugar-selective cell selectively metabolizes a first sugar that cannot be metabolized by the second sugar-selective cell, and the second sugar-selective cell selectively metabolizes a second sugar that cannot be metabolized by the first sugar-selective cell, wherein the first and second sugars are independently selected from the group consisting of glucose, xylose, arabinose, and galactose, and wherein at least one of the sugar-selective cells can metabolize only one sugar independently selected form the group consisting of glucose, xylose, arabinose, and galactose, to yield a co-culture of sugar-selective cells, under conditions to allow the plurality of sugar-selective cells to produce the biochemical.

2. The method of claim 1 wherein the plurality of sugar-selective cells comprises at least one hexose-selective cell and at least one pentose-selective cell.

3. The method of claim 2 wherein the hexose-selective cell comprises a glucose-selective cell, and wherein the pentose-selective cell comprises a xylose-selective cell.

4. The method of claim 1 wherein each of the first and second sugar-selective cells cannot metabolize at least two sugars independently selected from the group consisting of glucose, xylose, arabinose, and galactose.

5. The method of claim 1 wherein each of the first and the second sugar-selective cells cannot metabolize at least three sugars independently selected from the group consisting of glucose, xylose, arabinose, and galactose.

6. The method of claim 1 wherein each of the first and the second sugar-selective cells can metabolize only one sugar independently selected from the group consisting of glucose, xylose, arabinose, and galactose.

7. The method of claim 1 wherein the plurality of sugar-selective cells comprises:
a first *E. coli* cell comprising a modification or deletion of at least one gene involved in glucose metabolism so as to inhibit or prevent the first *E. coli* cell from consuming glucose; and
a second *E. coli* cell comprising a modification or deletion of at least one gene involved in xylose metabolism so as to inhibit or prevent the second *E. coli* cell from consuming xylose.

8. The method of claim 1 wherein the biochemical is ethanol, and wherein at least one of the plurality of sugar-selective cells has been genetically engineered for enhanced ethanol production.

9. The method of claim 8 wherein at least one of the plurality of sugar-selective cells has been genetically engineered to express or overexpress an alcohol dehydrogenase enzyme and/or a pyruvate decarboxylase enzyme.

10. The method of claim 1 wherein the biochemical is selected from the group consisting of ethanol, butanol, succinate, lactate, fumarate, formate, and pyruvate.

11. The method of claim 1 further comprising hydrolyzing a lignocellulosic biomass to produce the organic material.

12. The method of claim 1 further comprising purifying the biochemical.

13. A method for producing succinate comprising:
concurrently contacting an organic material comprising a mixture of sugars with a plurality of sugar-selective *Escherichia coli* cells under conditions to allow the plurality of sugar-selective cells to produce succinate, wherein at least one sugar-selective cell comprises knockouts of a gene selected from the group consisting of ldh, pfl, and ptsG, or any combination thereof.

14. The method of claim 13 wherein the plurality of sugar-selective cells comprises at least one hexose-selective cell and at least one pentose-selective cell.

15. The method of claim 13 wherein the plurality of sugar-selective cells comprises first and second sugar-selective cells, wherein the first sugar-selective cell metabolizes a first sugar that cannot be metabolized by the second sugar-selective cell, and the second sugar-selective cell metabolizes a second sugar that cannot be metabolized by the first sugar-selective cell, and wherein the first and second sugars are independently selected from the group consisting of glucose, xylose, arabinose, and galactose.

16. The method of claim 13 wherein at least one of the plurality of sugar-selective cells cannot metabolize at least two sugars independently selected from the group consisting of glucose, xylose, arabinose, and galactose.

* * * * *